United States Patent
Drezek et al.

(10) Patent No.: US 11,104,964 B2
(45) Date of Patent: Aug. 31, 2021

(54) UNIVERSAL MICROBIAL DIAGNOSTICS USING RANDOM DNA PROBES

(71) Applicant: WILLIAM MARSH RICE UNIVERSITY, Houston, TX (US)

(72) Inventors: Rebekah A. Drezek, Spring, TX (US); Richard G. Baraniuk, Houston, TX (US); Amirali Aghazadeh, Houston, TX (US); Mona Sheikh, Redwood City, CA (US); Adam Y. Lin, Chicago, IL (US); Allen L. Chen, Silver Spring, MD (US); Pallavi Bugga, Houston, TX (US)

(73) Assignee: William Marsh Rice University, Houston, TX (US)

( * ) Notice: Subject to any disclaimer, the term of this patent is extended or adjusted under 35 U.S.C. 154(b) by 462 days.

(21) Appl. No.: 15/944,586

(22) Filed: Apr. 3, 2018

(65) Prior Publication Data

US 2018/0355411 A1  Dec. 13, 2018

Related U.S. Application Data

(60) Provisional application No. 62/480,808, filed on Apr. 3, 2017.

(51) Int. Cl.
*C12Q 1/689* (2018.01)
*C12Q 1/6816* (2018.01)

(52) U.S. Cl.
CPC .......... *C12Q 1/689* (2013.01); *C12Q 1/6816* (2013.01)

(58) Field of Classification Search
CPC ..................................................... C12Q 1/689
See application file for complete search history.

(56) References Cited

PUBLICATIONS

Aghazadeh, Amirali, et al. "Insense: Incoherent sensor selection for sparse signals." *Signal Processing* 150 (2018): 57-65.
Aghazadeh, Amirali, et al. "Universal microbial diagnostics using random DNA probes." *Science Advances* 2.9 (2016): e1600025.
Aghazadeh, Universal Microbial Diagnostics using Random DNA Probes, (Rice University, 2014). [this is the attached 2014 thesis].
Amini, Arash, and Farokh Marvasti. "Deterministic construction of binary, bipolar, and ternary compressed sensing matrices." *IEEE Transactions on Information Theory* 57.4 (2011): 2360-2370.
Attouch, Hedy, Jérôme Bolte, and Benar Fux Svaiter. "Convergence of descent methods for semi-algebraic and tame problems: proximal algorithms, forward-backward splitting, and regularized Gauss-Seidel methods." *Mathematical Programming* 137.1-2 (2013); 91-129.
Baraniuk, Richard G. "Compressive sensing" IEEE Signal Processing Magazine. (2007): 118-124.
Baraniuk, Richard G. "More is less: signal processing and the data deluge." *Science* 331.6018 (2011): 717-719.

(Continued)

*Primary Examiner* — Diana B Johannsen
(74) *Attorney, Agent, or Firm* — Parker Highlander PLLC

(57) ABSTRACT

The present disclosure is directed to compositions and methods present a universal microbial diagnostic (UMD) platform to screen for microbial organisms in a sample using a small number of random DNA probes that are agnostic to the target DNA sequences. The UMD platform can be used to direct and monitor appropriate treatments, thus minimizing the risk of antibiotic resistance, and enhancing patient care.

18 Claims, 17 Drawing Sheets
(16 of 17 Drawing Sheet(s) Filed in Color)
Specification includes a Sequence Listing.

(56) References Cited

PUBLICATIONS

Bauer, Michael, and Konrad Reinhart. "Molecular diagnostics of sepsis—Where are we today?." *International Journal of Medical Microbiology* 300.6 (2010): 411-413.
Bruckstein, Alfred M., Michael Elad, and Michael Zibulevsky. "On the uniqueness of nonnegative sparse solutions to underdetermined systems of equations." *IEEE Transactions on Information Theory* 54.11 (2008): 4813-4820.
Cai, T. Tony, and Lie Wang. "Orthogonal matching pursuit for sparse signal recovery with noise." Institute of Electrical and Electronics Engineers, 2011.
Candès, Emmanuel J. "Compressive sampling." *Proceedings of the International Congress of Mathematicians.* vol. 3. 2006.
Candès, Emmanuel J., and Michael B. Wakin. "An introduction to compressive sampling [a sensing/sampling paradigm that goes against the common knowledge in data acquisition]." *IEEE Signal Processing Magazine* 25.2 (2008): 21-30.
Candes, Emmanuel J., Justin K. Romberg, and Terence Tao. "Stable signal recovery from incomplete and inaccurate measurements." *Communications on Pure and Applied Mathematics: A Journal Issued by the Courant Institute of Mathematical Sciences* 59.8 (2006): 1207-1223.
Chakravorty, Soumitesh, et al. "Rapid universal identification of bacterial pathogens from clinical cultures by using a novel sloppy molecular beacon melting temperature signature technique." *Journal of Clinical Microbiology* 48.1 (2010): 258-267.
Chen, Scott Shaobing, David L. Donoho, and Michael A. Saunders. "Atomic decomposition by basis pursuit." *SIAM Review* 43.1 (2001): 129-159.
Chen, Yunmei, and Xiaojing Ye. "Projection onto a simplex." *arXiv preprint* arXiv:1101.6081 (2011).
Chepuri, Sundeep Prabhakar, and Geert Leus. "Sparsity-promoting sensor selection for non-linear measurement models." *IEEE Transactions on Signal Processing* 63.3 (2015): 684-698.
Condat, Laurent. "Fast projection onto the simplex and the l1Ball," *Mathematical Programming* 158.1-2 (2016): 575-585.
Dai, Wei, et al. "Compressive sensing DNA microarrays," *EURASIP Journal on Bioinformatics and Systems Biology* 2009.1 (2008): 162824.
Das, Abhimanyu, and David Kempe. "Algorithms for subset selection in linear regression." *Proceedings of the Fortieth Annual ACM Symposium on Theory of Computing.* ACM, 2008.
Das, Abhimanyu and David Kempe. "Submodular meets spectral: Greedy algorithms for subset selection, sparse approximation and dictionary selection." *arXiv preprint* arXiv:1102.3975 (2011).
Davenport, Mark A., et al. "Signal Processing With Compressive Measurements." *J. Sel. Topics Signal Processing* 4.2 (2010): 445-460.
Donoho, D. "Compressed sensing, IEEE T. Inform. Theory, 52, 1289-1306." (2006).
Donoho, David L. and Jared Tanner. "Sparse nonnegative solution of underdetermined linear equations by linear programming." *Proceedings of the National Academy of Sciences* 102.27 (2005): 9446-9451.
Donoho, David L., and Xiaoming Huo. "Uncertainty principles and ideal atomic decomposition." *IEEE Transactions on Information Theory* 47.7 (2001): 2845-2862.
Donoho, David L., Arian Maleki, and Andrea Montanari, "Message-passing algorithms for compressed sensing." *Proceedings of the National Academy of Sciences* 106.45 (2009): 18914-18919.
Donoho, David L., Michael Elad, and Vladimir N. Temlyakov. "Stable recovery of sparse overcomplete representations in the presence of noise." *IEEE Transactions on Information Theory* 52.1 (2006): 6-18.
Duarte-Carvajalino, Julio Martin, and Guillermo Sapiro. "Learning to sense sparse signals: Simultaneous sensing matrix and sparsifying dictionary optimization." *IEEE Transactions on Image Processing* 18.7 (2009): 1395-1408.

Elad, Michael. "Optimized projections for compressed sensing." *IEEE Transactions on Signal Processing* 55.12 (2007): 5695-5702.
Ford, Ian, D. M. Titterington, and Christos P. Kitsos. "Recent advances in nonlinear experimental design." *Technometrics* 31.1 (1989): 49-60x.
Golovin, Daniel, Matthew Faulkner, and Andreas Krause. "Offline distributed sensor selection." *Proceedings of the 9th ACM/IEEE International Conference on Information Processing in Sensor Networks,* ACM, 2010.
Gribonval, Rémi, and Pierre Vandergheynst "On the exponential convergence of matching pursuits in quasi-incoherent dictionaries." *IEEE Transactions on Information Theory* 52.1 (2006): 255-261.
Herzet, Cédric, et al. "Exact recovery conditions for sparse representations with partial support information." *IEEE Transactions on Information Theory* 59.11 (2013): 7509-7524.
Jeričević, Željko, and Željko Kušter. "Non-linear optimization of parameters in Michaelis-Menten kinetics." *Croatica chemica acta* 78.4 (2005): 519-523.
Joshi, Siddharth, and Stephen Boyd. "Sensor selection via convex optimization," *IEEE Transactions on Signal Processing* 57.2 (2009): 451-462.
Klompas, Michael, Deborah S. Yokoe, and Robert A. Weinstein, "Automated surveillance of health care-associated infections," *Clinical Infectious Diseases* 48.9 (2009): 1268-1275.
Krause, Andreas, Ajit Singh, and Carlos Guestrin. "Near-optimal sensor placements in Gaussian processes: Theory, efficient algorithms and empirical studies." *Journal of Machine Learning Research* Feb. 9, 2008: 235-284.
Ma, Zhao, et al. "Engineering novel molecular beacon constructs to study intracellular RNA dynamics and localization." *Genomics, Proteomics & Bioinformatics* 15.5 (2017): 279-286.
Mohtashemi, Mojdeh, et al. "Open-target sparse sensing of biological agents using DNA microarray." *BMC Bioinformatics* 12.1 (2011): 314.
Needell, Deanna, and Roman Vershynin. "Signal recovery from incomplete and inaccurate measurements via regularized orthogonal matching pursuit." *arXiv preprint* arXiv: 0712.1360(2007).
Needell, Deanna, and Roman Vershynin. "Uniform uncertainty principle and signal recovery via regularized orthogonal matching pursuit." *Foundations of Computational Mathematics* 9.3 (2009): 317-334.
Nesterov, Yu. "Gradient methods for minimizing composite functions." *Mathematical Programming* 140.1 (20113): 125-161.
Ranieri, Juri, Amina Chebira, and Martin Vetterli. "Near-optimal sensor placement for linear inverse problems." *IEEE Transactions on Signal Processing* 62.5 (2014): 1135-1146.
Ranieri, Juri, et al. "EigenMaps: Algorithms for optimal thermal maps extraction and sensor placement on multicore processors," *Proceedings of the 49th Annual Design Automation Conference.* ACM, 2012.
SantaLucia Jr, John, and Donald Hicks. "The thermodynamics of DNA structural motifs." *Annu. Rev. Biophys. Biomol. Struct.* 33 (2004): 415-440.
Sen, Debarshi, et al. "Sparsity-based approaches for damage detection in plates." *Mechanical Systems and Signal Processing* 117 (2019): 333-346.
Shamaiah, Manohar, Siddhartha Banerjee, and Haris Vikalo. "Greedy sensor selection: Leveraging submodularity." *49th IEEE Conference on Decision and Control (CDC).* IEEE, 2010.
Sheikh, Mona A. *Genomic Detection Using Sparsity-inspired Tools.* Diss. Rice University, 2011.
Strohmer, Thomas, and Robert W. Heath Jr. "Grassmannian frames with applications to coding and communication." *Applied and Computational Harmonic Analysis* 14.3 (2003): 257-275.
Tibshirani, Robert. "Regression shrinkage and selection via the lasso." *Journal of the Royal Statistical Society: Series B (Methodological)* 58.1 (1996): 267-288.
Tropp, Joel A. "Greed is good: Algorithmic results for sparse approximation." *IEEE Transactions on Information Theory* v50.10 (2004): 2231-2242.
Tropp, Joel A., and Anna C. Gilbert. "Signal recovery from random measurements via orthogonal matching pursuit," *IEEE Transactions on Information Theory* 53.12 (2007): 4655-4666.

(56) References Cited

PUBLICATIONS

Tropp, Joel A., et al. "Designing structured tight frames via an alternating projection method." *IEEE Transactions on Information Theory* 51.1 (2005): 188-209.

Wang, Hanbiao, et al. "Entropy-based sensor selection heuristic for target localization." *Proceedings of the 3rd International Symposium on Information Processing in Sensor Networks.* ACM, 2004.

Wang, Juexiao Sherry, and David Yu Zhang. "Simulation-guided DNA probe design for consistently ultraspecific hybridization," *Nature Chemistry* 7.7 (2015): 545.

Wang, Weiran, and Miguel A. Carreira-Perpinán. "Projection onto the probability simplex: An efficient algorithm with a simple proof, and an application." *arXiv preprint* arXiv:1309.1541 (2013).

Zhang, David Yu, Sherry Xi Chen, and Peng Yin. "Optimizing the specificity of nucleic acid hybridization." *Nature Chemistry* 4.3 (2.

Zhou, Xiao-Qing, Yong Xia, and Shun Weng. "L1 regularization approach to structural damage detection using frequency data." *Structural Health Monitoring* 14.6 (2015): 571-582.

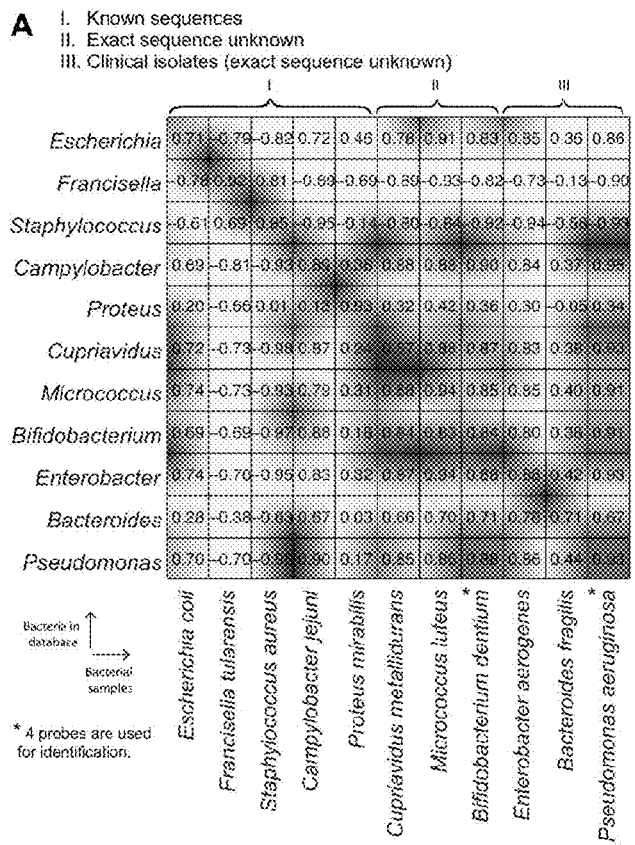
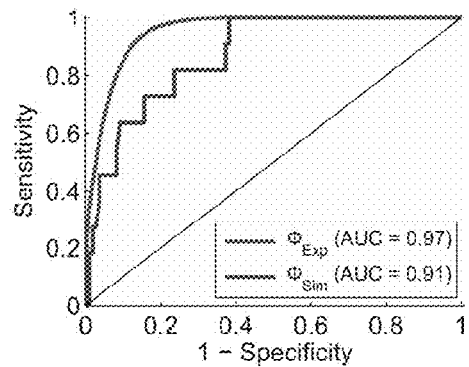
FIGS. 9A-B
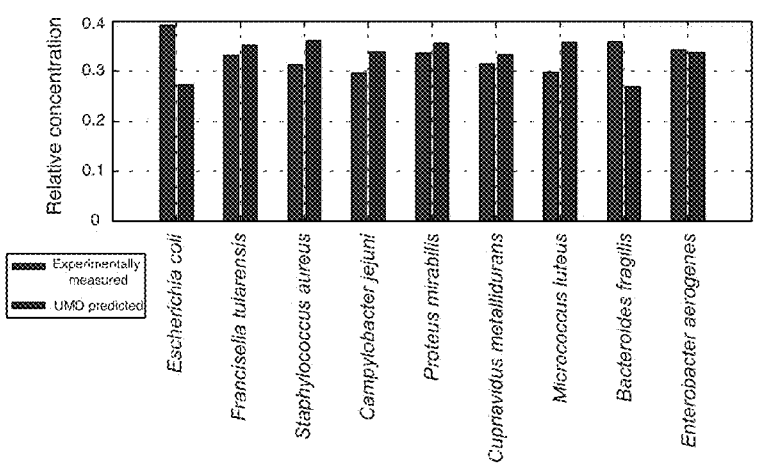
FIG. 10

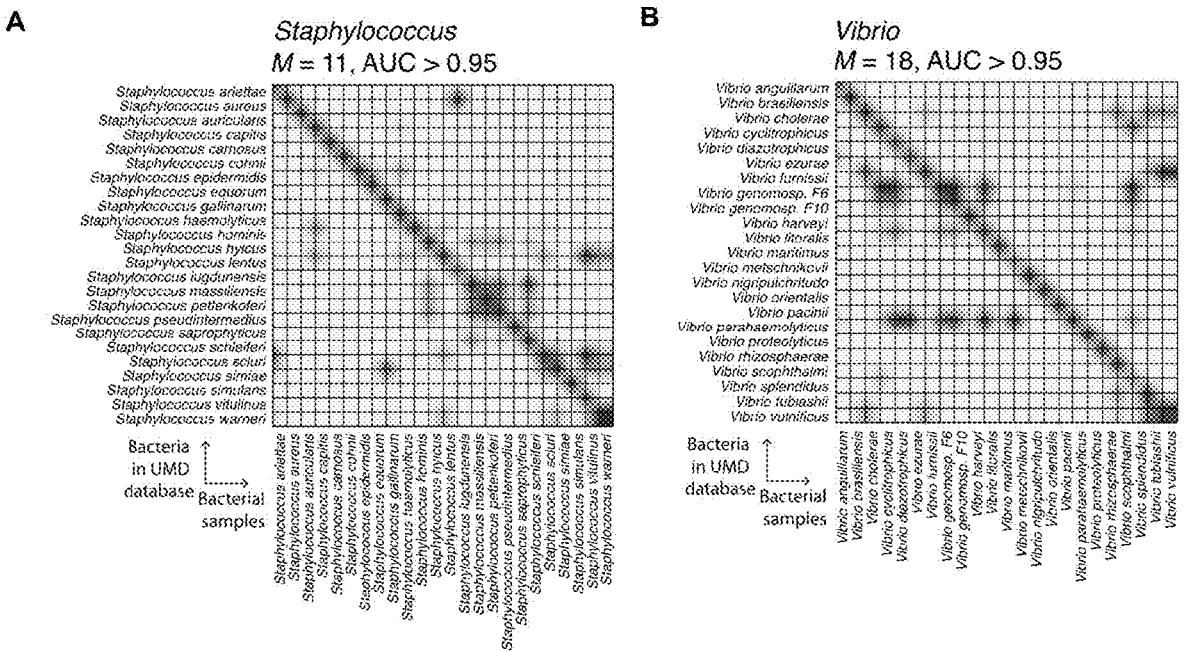
FIGS. 11A-B
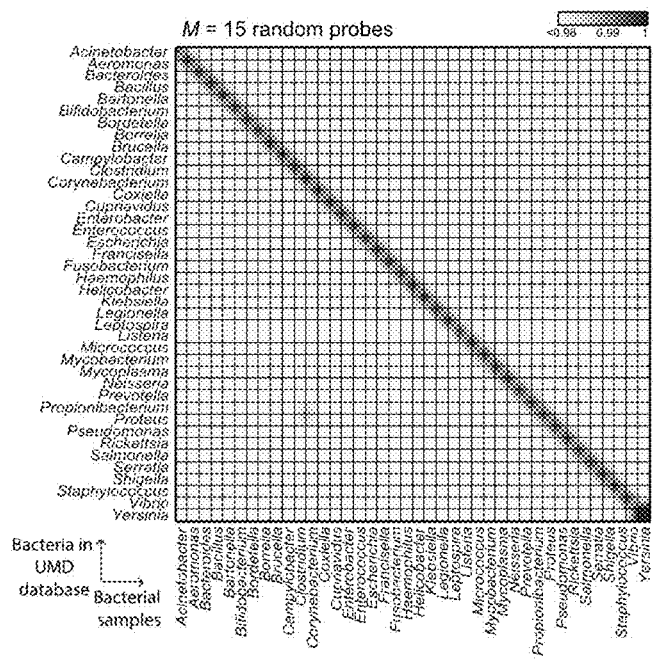
FIG. 12

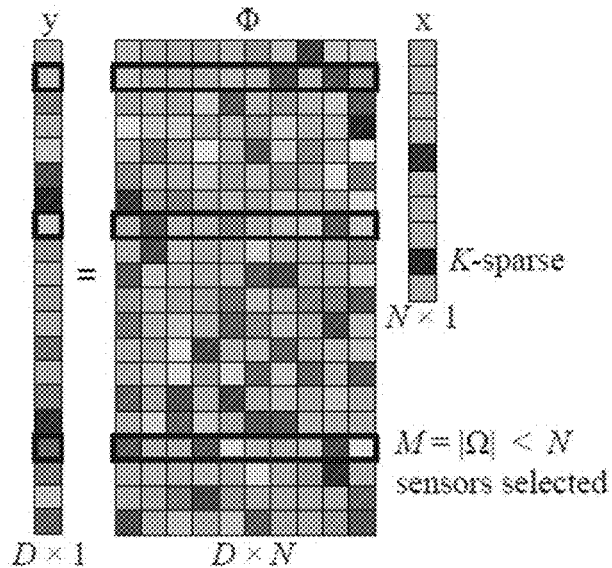

Algorithm 1: Insense

Input: $\Phi$
Output: $Z = \text{diag}(z)$
Initialization:
$z \leftarrow z_0$;
$G \leftarrow \Phi^T Z \Phi$;
while *stopping criterion = false* do
    1. $k \leftarrow k + 1$;
    2. update $\nabla_z f(z^k)$ based on equation (8);
    3. $\gamma_k \leftarrow \text{line search}(f, \nabla_z f(z^k), z^k)$;
    4. $z^k \leftarrow z^k - \gamma^k \nabla_z f(z^k)$ {gradient step};
    5. $z^{k+1} \leftarrow P_{SBS}(z^k)$ {SBS projection step};
end

FIG. 16

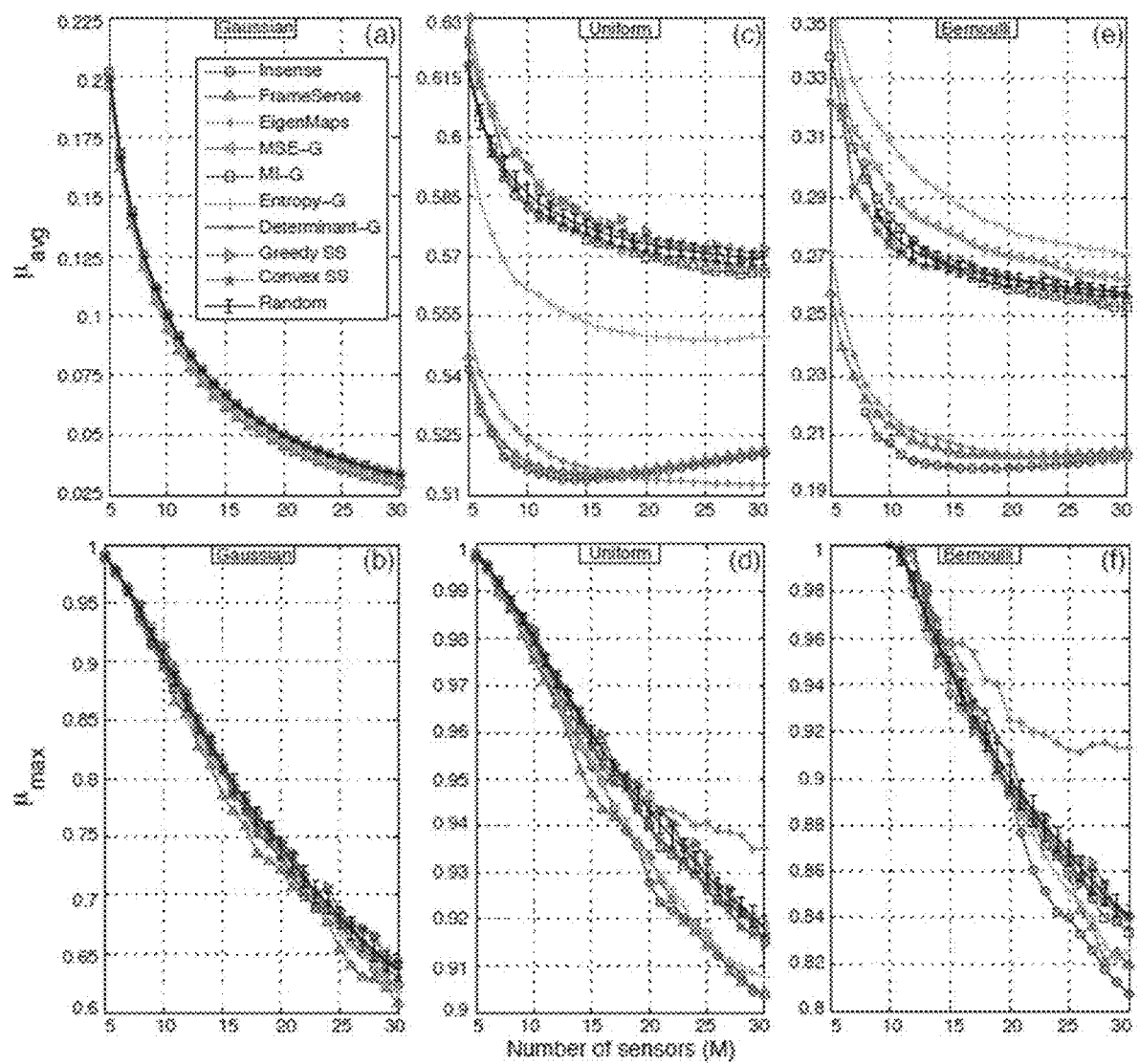
FIGS. 17A-F

UNIVERSAL MICROBIAL DIAGNOSTICS USING RANDOM DNA PROBES

The present application claims the priority benefit of U.S. provisional application No. 62/480,808, filed Apr. 3, 2017, the entire contents of which is incorporated herein by reference.

GOVERNMENT SUPPORT CLAUSE

This invention was made with government support under grant no. CCF-0728867 awarded by the National Science Foundation, grant no. DGE-0940902 awarded by the National Science Foundation, and grant no. T32EB009379 awarded by the National Institutes of Health. The government has certain rights in the invention.

BACKGROUND

1. Field of the Disclosure

The present disclosure relates generally to the fields of medicine, infectious disease, and microbiology. More particular, the disclosure relates to compositions and methods for the detection and analysis of bacterial infections.

2. Background

The accurate, efficient, and rapid identification of microbial organisms such as bacteria and viruses is of mounting importance in the fields of health care, environmental monitoring, defense, and beyond (Klompas & Yokoe, 2009; Pinto, 2013 and Dorst et al., 2010). Sepsis from bacterial infection is currently the 11$^{th}$ leading cause of death in the United States, and the mortality rate of bloodstream infections is high (14-50%) (Martin et al., 2003; Hoyer & Xu, 2012 and Mylotte & Tayara, 2000).

Conventional strategies for microbial detection are based on microbe-specific genomic or proteomic markers and protocols. Polymerase chain reaction (PCR)-based approaches rely on the binding of specific capture probes with unique genomic identifiers, such as the 16S ribosomal DNA subunit in bacteria. While these methods show promise as highly specific tools for microbial identification (Dark et al., 2009 and Pechorsky et al., 2009), they have limitations in clinical, industrial, and defense settings (Sontakke et al., 2009 and Sibley et al., 2012). In the case of an epidemic, the detection of a newly mutated species using current PCR methods would require entirely new capture probes to be manufactured, introducing additional costs and delays. For bacterial detection, blood cultures typically require 48 to 72 hours to produce reliable results (Riedel & Carroll, 2010; Paolucci et al., 2010; Bauer & Reinhart, 2010 and Peters et al., 2004). During this waiting period, administration of broad-spectrum antibiotics breeds further threats of bacterial resistance and missed coverage (Centers for Disease Control and Prevention Antibiotic Resistance threats in the United States, 2013). DNA microarrays also require many target-specific probes to detect multiple pathogens and lie dormant against unknown organisms. Whole genome sequencing (WGS), currently the most complete and accurate technique, is not yet conducive to point-of-care diagnostics; it requires millions of expensive sequencing reads to assemble or align with genomic identifiers. It follows that there is a critical need for a new means of microbial detection: a universal (i.e., works for bacteria outside of the target library), inexpensive (i.e., requires minimal resources for acquisition such as DNA probes and sequencing reads, etc.), and rapid sensing platform capable of identifying known and novel species with high phylogenetic power.

SUMMARY

Thus, in accordance with the present disclosure, there is provided a method of detecting a bacterial infection in a subject comprising (a) providing a set of probes comprising SEQ ID NOS: 1, 2, 3, 4 and 5, and optionally having SEQ ID NOS: 6, 7, 8, 9 and 10, respectively, hybridized thereto; (b) providing a first sample from said subject; (c) obtaining hybridization information for each of probes SEQ ID NOS: 1, 2, 3, 4 and 5 with one or more bacterial genomes in said sample; and (d) identifying the presence of one or more bacterial genomes in said sample based on a predetermined hybridization pattern for said set of probes with a given bacterial genome. The first sample is a body fluid, such as blood, sputum, tears, saliva, mucous or serum, urine, exudate, transudate, tissue scrapings or feces. The method may further comprise treating said subject for a bacterial infection. The subject may be a human or non-human mammal.

Detection may comprise detecting more than one bacterial genome, such as multiple bacterial genomes from the same species, or multiple bacterial genomes are from different species. The multiple different bacterial species may be from 2, 3, 4, 5, 6, 7, 8, 9, 10, 15, 20, 30, 40, 50, 60, 70, 80, 90 or 100 different bacterial species. Each of the probes may be comprised within a molecular beacon, such as a molecular beacon that comprises a 38 nucleotide loop sequence and a four nucleotide-long stem sequence. The probes may each comprises a label, such as a FRET label, or dual FRET labels. In one embodiment, obtaining hybridization information may comprise measuring FRET from dual labels on said each of said probes. The bacterium or bacterial genomes may be from pathogenic bacteria, from gram-negative bacteria, gram-positive bacteria or gram-indeterminate bacteria. The bacterial genomes may be from a mixture of gram-indeterminate bacteria with (a) gram-negative bacteria, (b) gram-positive bacteria, or (c) gram-negative and gram-positive bacteria. The bacterium or bacterial genomes may be from *Escherichia coli, Pseudomona aeruginosa* and/or *Staphylococcus aureus*.

Step (c) may comprise obtaining quantitative hybridization information, and optionally the method may further comprise quantitating the number of bacterial genomes in said sample, and optionally may even further comprise performing steps (a)-(d) on a second sample from said subject. The second sample may have been obtained at a second point in time as compared to said first sample, and the number of bacterial genomes in said first and second samples is compared. The anti-bacterial therapy may have been administered between obtaining of said first and second samples, and said method assesses therapeutic efficacy.

In another embodiment, there is provided a method of classifying a bacterial infection in a subject comprising (a) providing a set of probes comprising SEQ ID NOS: 1, 2, 3, 4 and 5, and optionally having SEQ ID NOS: 6, 7, 8, 9 and 10, respectively, hybridized thereto; (b) providing a first sample from said subject with a bacterial infection or suspected to have a bacterial infection; (c) obtaining hybridization information for each of probes SEQ ID NOS: 1, 2, 3, 4 and 5 with one or more bacterial genomes in said sample; and (d) classifying the bacterial infection by identifying the presence of one or more bacterial genomes in said sample based on a predetermined hybridization pattern for said set of probes with a given bacterial genome.

A further embodiment comprise a method of treating a bacterial infection in a subject comprising (a) providing a set of probes comprising SEQ ID NOS: 1, 2, 3, 4 and 5, and optionally having SEQ ID NOS: 6, 7, 8, 9 and 10, respectively, hybridized thereto; (b) providing a first sample from said subject; (c) obtaining hybridization information for each of probes SEQ ID NOS: 1, 2, 3, 4 and 5 with one or more bacterial genomes in said sample; (d) identifying the presence of one or more bacterial genomes in said sample based on a predetermined hybridization pattern for said set of probes with a given bacterial genome; and (e) treating said subject based on the identification of one or more bacterial genomes in step (d).

An additional embodiment comprises a kit comprising a set of probes comprising SEQ ID NOS: 1, 2, 3, 4 and 5, and optionally having SEQ ID NOS: 6, 7, 8, 9 and 10, respectively, hybridized thereto. Each of said probes may be comprised within a molecular beacon, such as a molecular beacon that comprises a 38 nucleotide loop sequence and a four nucleotide-long stem sequence. One or more or all of said probes may contain labels, such as Forster Resonance Energy Transfer labels, such as dual FRET labels. The kit may further comprise bacterial genomes or fragments thereof to serve a positive controls. The kit may further comprise one or more buffers, solvents or diluents. The kit may further comprise one or more containers for rehydrating a lyophilized reagent. The kit may further comprise one or more positive or negative control probes.

In one embodiment, provided herein are methods of selecting a set of M random DNA probes, the method comprising: (a) generating a sensing matrix comprising the hybridization affinity of D random DNA probes to N bacterial species; and (b) determining the set of M random DNA probes having a smallest average coherence among the bacterial species. In some aspects, the M random DNA probes is a subset of the D random DNA probes. In some aspects, M is smaller than D. In some aspects, D is 100 and N is 42. In some aspects, the set of M random DNA probes comprises at least fifteen probes, wherein an average Basis Pursuit recovery performance in detecting bacterial species in a sample comprising at least three organisms is greater than 90%. In some aspects, the set of M random DNA probes comprises Molecular Beacons. In some aspects, the set of M random DNA probes comprises toehold probes.

In one embodiment, methods are provided for detecting a bacterial infection in a subject comprising: (a) providing a set of M random DNA probes selected according to the method of claim 36; (b) providing a first sample from said subject; (c) obtaining hybridization information for each of the M random DNA probes with one or more bacterial genomes in said sample; and (d) identifying the presence of one or more bacterial genomes in said sample based on said hybridization information. In some aspects, the hybridization information is obtained by single molecule FISH.

In some aspects, the identifying in step (d) comprises comparing the hybridization information obtained in step (c) with a predetermined hybridization pattern for the set of M random DNA probes with a given bacterial genome. In some aspects, the identifying in step (d) comprises performing compression sensing on the hybridization information obtained in step (c).

In some aspects, said first sample is a body fluid. In some aspects, said first sample is blood, sputum, tears, saliva, mucous or serum, urine, exudate, transudate, tissue scrapings or feces. In some aspects, detection comprises detecting more than one bacterial genome. In certain aspects, the more than one bacterial genomes are from the same species. In certain aspects, the more than one bacterial genomes are from different species. In certain aspects, the more than one different bacterial species are from 2, 3, 4, 5, 6, 7, 8, 9, 10, 15, 20, 30, 40, 50, 60, 70, 80, 90 or 100 different bacterial species.

In some aspects, each of said probes are comprised within a molecular beacon. In some aspects, each of said probes are comprised within a toehold probe. In certain aspects, said molecular beacon comprises a 38 nucleotide loop sequence and a four nucleotide-long stem sequence. In some aspects, each of said probes carries a label. In certain aspects, said probe is a Forster Resonance Energy Transfer label. In certain aspects, obtaining hybridization information comprises measuring FRET from dual labels on said each of said molecular beacons.

In some aspects, said bacterial genomes are from pathogenic bacteria. In some aspects, said bacterial genomes are from gram-negative bacteria. In some aspects, said bacterial genomes are from gram-positive bacteria. In some aspects, said bacterial genomes are from gram-indeterminate bacteria. In some aspects, said bacterial genomes are from a mixture of gram-indeterminate bacteria with (a) gram-negative bacteria, (b) gram-positive bacteria, or (c) gram-negative and gram-positive bacteria. In some aspects, said bacterial genomes are from *Escherichia coli, Pseudomona aeruginosa* and/or *Staphylococcus aureus*.

In some aspects, step (c) comprises obtaining quantitative hybridization information. In some aspects, the method further comprises quantitating the number of bacterial genomes in said sample. In some aspects, the method further comprises performing steps (a)-(d) on a second sample from said subject. In certain aspects, said second sample was obtained at a second point in time as compared to said first sample, and the number of bacterial genomes in said first and second samples is compared. In certain aspects, an anti-bacterial therapy is administered between obtaining of said first and second samples, and said method assesses therapeutic efficacy.

In some aspects, the method further comprises treating said subject for a bacterial infection. In some aspects, said subject is a human or non-human mammal.

In one embodiment, provided herein are kits comprising a set of probes comprising M random DNA probes selected according to a method of the present embodiments. In some aspects, each of said probes are comprised within a molecular beacon. In some aspects, each of said probes are comprised within a toehold probe. In certain aspects, said molecular beacon comprises a 38 nucleotide loop sequence and a four nucleotide-long stem sequence. In some aspects, one or more of said probes contain dual Forster Resonance Energy Transfer labels. In some aspects, the kits further comprise bacterial genomes or fragments thereof to serve a positive controls. In some aspects, the kits further comprise one or more buffers, solvents or diluents. In some aspects, the kits further comprise one or more containers for rehydrating a lyophilized reagent. In some aspects, the kits further comprise one or more positive or negative control probes.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

(FIG. 1A) Genomic DNA is extracted from a bacterial sample and thermal cycled with M random DNA probes. The genome probe binding is quantified, producing a probe-binding vector y; in this study the random probes are in the form of molecular beacons (MBs), and the DNA-probe binding is quantified by the ratio of open/hybridized to closed/non-hybridized MBs. (FIG. 1B) The hybridization binding level of each probe to a potentially large reference database of N bacterial genomes (B1, B2, . . . , BN) is predicted using a thermodynamic model and stored in an M×N hybridization affinity matrix $\Phi$. (FIG. 1C) Assuming K bacterial species comprises the sample, the probe-binding vector y is a sparse linear combination of the corresponding K columns of the matrix $\Phi$ weighted by the bacterial concentrations x, i.e., $y=\Phi x+n$, where the vector n accounts for noise and modeling errors. When K is small enough and M is large enough, $\Phi$ can be effectively inverted using techniques from compressive sensing, yielding the estimate for the microbial makeup of the sample x; in this illustration the K=2 bacteria labeled B2 and B7 are present in the sample.

(FIG. 2A) DNA sequence structure of five test random DNA probes. The sequence of Random Probe 1 is SEQ ID NO: 1; the sequence of Random Probe 2 is SEQ ID NO: 2; the sequence of Random Probe 3 is SEQ ID NO: 3; the sequence of Random Probe 4 is SEQ ID NO: 4; the sequence of Random Probe 5 is SEQ ID NO: 5. (FIG. 2B) Both strands of the bacterial genome (blue lines) are first thermodynamically aligned with the probe sequence. The sequence of the bacteria is segmented into fragments of roughly equal length (~100-200 nts), each containing a significant hybridization affinity with the probe. Then, all of the bacterial fragments and probe sequences along with the experimental conditions are fed into the DNA software (SantaLucia & Hicks, 2004) to predict all stable probe-bacteria complexes and concentrations. These concentrations, in aggregate, determine the concentration of opened molecular beacons, which is defined as the hybridization affinity of the probes to the bacterial genome. (FIG. 2C) Example of a predicted probe-bacteria fragment binding with many base pair mismatches. The sequence of the bacterial fragment is SEQ ID NO: 11. The sequence of the probe is SEQ ID NO: 1.

(FIG. 3A) Experimentally measured FRET ratios to quantify hybridization between bacterial DNA and probes 1, 2, 3, 4, and 5. (FIG. 3B) Hybridization affinity between DNA samples and probes, converted from FRET ratio through the probe characteristic curve fit equations (Table 1 and FIG. 6). (FIG. 3C) Heat map of normalized inner products between the experimentally obtained hybridization affinity and predicted hybridization affinities (by thermodynamic model) for nine DNA samples as a measure of the similarity of the probe measurements to the bacteria in the dataset. DNA samples are clustered into three groups: I. Exact sequence known, II. Exact sequence unknown, and III. Clinical isolates (whose exact sequence unknown). UMD correctly recovers the diagonally highlighted bacterium (with inner product>0.9). (FIG. 3D) The average receiver operating characteristic (ROC) curve of UMD in detecting nine bacteria, assuming the independence of the different experiments. Each point on the curve corresponds to a threshold value between [−1, 1]. UMD achieves high values of the area under the curve (AUC>0.9). (FIG. 3E) Correlation of measured and simulated hybridization affinities and the normalized root-mean-square error (NRMSE) of the prediction (straight line corresponds to maximum correlation). All experiments were performed in triplicate, and the results shown here average over the trials with the error bars representing the standard error of the mean (s.e.m.).

(FIG. 4A) The ROC curve in detecting single bacterium (K=1) with different noise levels. $\sigma_0=2.4\times10^{-8}$ M denotes the variance of the additive white Gaussian noise (AWGN) used in the simulation. This value is obtained from the experiments in FIG. 3A by calculating the propagated variance of measured FRET ratios. UMD performs more accurately with lower noise variance. The detection is almost perfect (AUC>0.95) under noise variance $\sigma=\sigma_0/5$. (FIG. 4B) The average ROC curve in detecting single bacterium using different number of random probes M and fixed noise variance $\sigma=\sigma_0$. The detection performance universally improves over all the 40 species by increasing the number of random probes. With 15 random probes, UMD achieves almost perfect detection performance (AUC>0.95). (FIG. 4C) The percentage of simulated trials, where K bacteria present in the samples were recovered correctly with zero false positives, among all possible $$\binom{40}{K}$$

bacteria mixtures (blue and red curves corresponding to K=2 and K=3 bacteria, respectively). Simulations were repeated 1000 times with randomly selected MBs, and error bars represent standard deviation (SD). (FIGS. 4D-E) Confusion matrices illustrating the detection result of UMD using M=3 and M=10 probes selected by the greedy probe selection (GPS) algorithm.

FIGS. 9A-B. Detection performance of 11 bacterial samples using five random probes. (FIG. 9A) The heat map and raw values of inner product of the experimentally obtained hybridization affinity and predicted hybridization affinity (by thermodynamic model) for eleven DNA samples as a measure of the similarity of the probe measurements. For detection of the two strains marked with asterisk (*), only four random probes (Probes 1, 2, 3, and 5) were utilized. (FIG. 9B) The average receiver operating characteristic (ROC) curve of UMD in detecting eleven bacteria, assuming the independence of different test trials. Each point on the curve corresponds to a threshold value between [−1, 1]. UMD achieves high values of the area under the curve using experimentally obtained Φexp (red line) and simulated Φsim using the DNA software.

FIG. 10. Comparison of the predicted concentrations of bacterial DNA with the experimentally measured values. Concentration of bacterial samples are estimated by compressive sensing recovery algorithm.

FIGS. 11A-B. Performance of UMD in species-level recovery of 24 strains of *Staphylococcus* and 23 strains of *Vibrio*. (FIG. 11A) UMD's confusion matrix in identifying 24 strains of *Staphylococcus*. With M=11 random probes, UMD identifies all the species of *Staphylococcus* genera with AUC>0.95. (FIG. 11B) UMD's confusion matrix in identifying 23 strains of *Vibrio*. With M=18 random probes, UMD identifies all the species of *Vibrio* with AUC>0.95.

FIG. 12. Performance of UMD in identifying pathogens in genus-level using 15 GPS probes. Using 15 GPS-selected probes, the difference between inner product values for various species is increased (when compared to detection results using M=3 probes in FIG. 4D and M=10 probes in FIG. 4E), leading to better robustness against noise and lower false positives (AUC=0.9971).

FIG. 15. Schematic of the sensor selection problem for sparse signals. Here, M=3 sensors indexed by $\Omega$={2, 8, 17} are selected from D=20 available sensors to recover a K=2-sparse vector $x \in \mathbb{R}^N$, N=10, from the linear system $y_\Omega = \Phi_\Omega x$.

FIG. 16. Workflow of the Insense algorithm.

FIGS. 17A-F. Comparison of Insense against the baseline algorithms in minimizing the average coherence $\mu_{avg}$ and maximum coherence $\mu_{max}$ of the selected sensing matrix $\Phi_\Omega$ from random sensing matrices with independent Gaussian (FIGS. 17A&B), Uniform (FIGS. 17C&D), and Bernoulli (FIGS. 17E&F) entries (D=N=100). Results are averaged over 20 trials with different random matrices.

DESCRIPTION OF ILLUSTRATIVE EMBODIMENTS

As discussed above, rapid diagnostics for microbial infections are urgently needed, not simply for the delivery of early and effective therapy, but for the avoidance of antibiotic resistance. In this disclosure, the inventors report on the design and validation of a new microbial diagnostic platform that satisfies the above desiderata. In common with microarrays and PCR-based techniques, the inventors' Universal Microbial Diagnostics (UMD) platform exposes a microbial sample (which may contain more than one genus/species) to a collection of DNA probes. In sharp contrast to conventional methods, however, the probes are randomly generated (and hence target-agnostic) permutations of nucleotides (nts) that freely hybridize to different spots and to different extents on different bacterial genomes. By measuring the degree to which the sample hybridizes with the collection of random probes, the inventors set up a statistical inverse problem to detect the presence and estimate the concentrations of the various bacteria in the sample. Using signal recovery techniques from the recently developed theory of compressive sensing (Donoho, 2006; Baraniuk, 2007), the inventors show that it is possible to stably solve this inverse problem even when the number of probes is significantly smaller than the size of the library of possible bacteria of interest. Due to the random structure of the probes, and the variabilities that bacterial organisms exhibit in their genomes, UMD is universal, inexpensive, rapid, and phylogenetically informative (random probes bind to arbitrary spots on the genome). Moreover, due to the universal nature of its probe design, UMD can classify not only known organisms but also novel mutants with their closest known relatives.

Furthermore, the inventor's Incoherent Sensor Selection (Insense) algorithm is used to design the optimal probe sequences by optimizing the average squared coherence of the columns of the selected sensors (rows) via a computationally efficient relaxation (Aghazadeh et al., 2017, which is incorporated by reference herein in its entirety). Insense provides superior performance than existing state-of-the-art sensor selection algorithms, especially in the real-world problems of microbial diagnostics.

These and other aspects of the disclosure are set out below.

I. UNIVERSAL MICROBIAL DETECTION

In Universal Microbial Detection, or "UMD," (see FIG. 1A), the genomic DNA of an infectious sample is extracted and exposed to a small number M of DNA probes, which hybridize to the genomic DNA at various locations; this hybridization is experimentally quantified, producing a probe-binding (or hybridization) vector y whose entries correspond to the hybridization binding level of each probe with the microbial sample.

Figure 1:
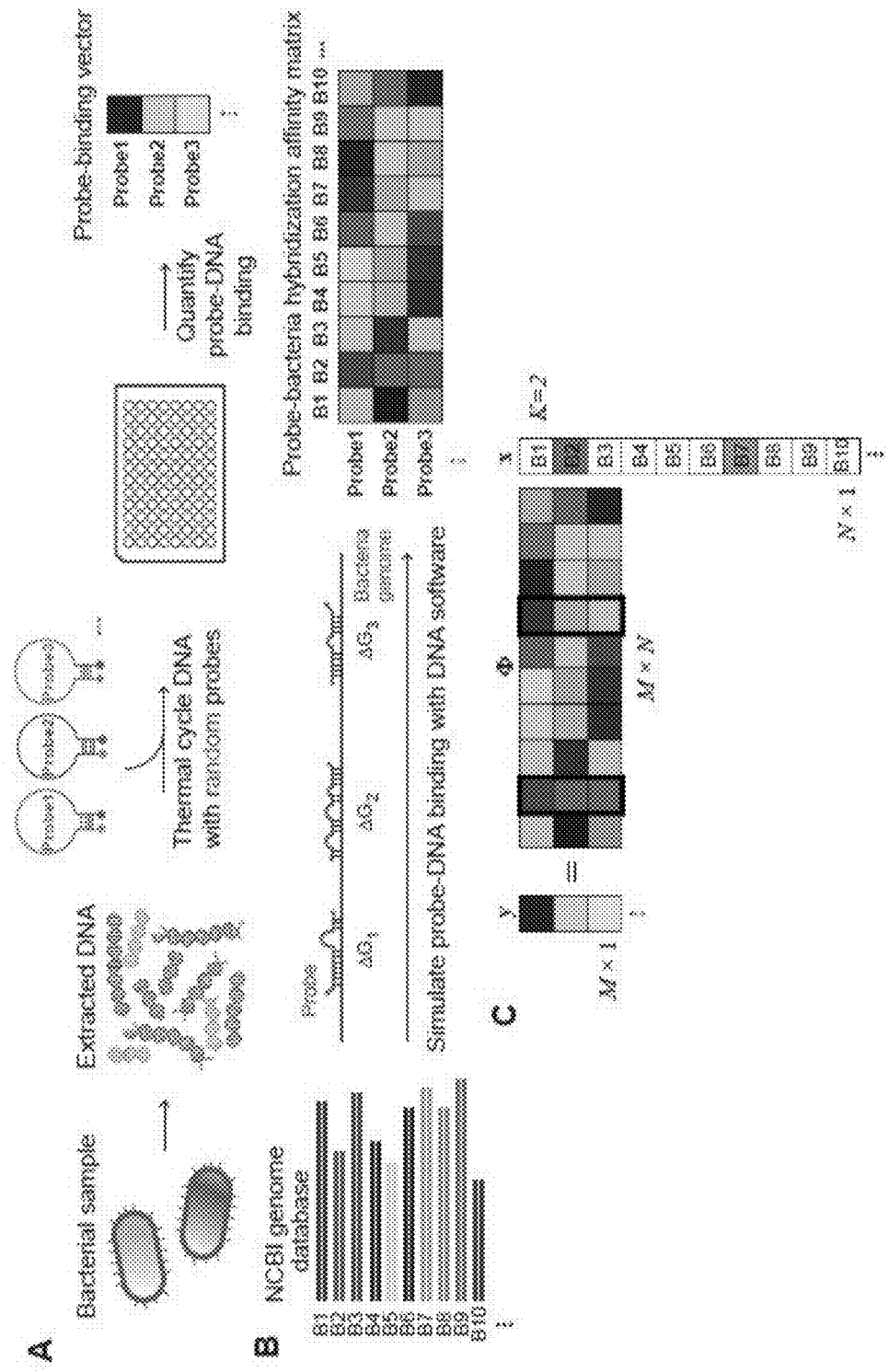
FIGS. 1A-C. Schematic of Universal Microbial Diagnostics (UMD) platform.

A priori, the hybridization binding level of each probe to a reference database of N bacterial genomes is obtained and stored in an M×N hybridization affinity matrix (FIG. 1B). The hybridization affinity matrix can be measured either experimentally in vitro or predicted computationally in silico. To speed up the probe design and prove the concept of UMD, here the inventors predict the affinity matrix using a thermodynamic model in silico. To compute the entry $\varphi_{ij}$ in the matrix $\Phi$, the hybridization binding level of probe i to genome j, the inventors first perform a rapid thermodynamic alignment of the sequence of the probe to the sequence of the genome using the alignment model described in (SantaLucia & Hicks, 2004). Next, the inventors extract sequence fragments from the genome sequence, which contain a significant hybridization affinity with the probe sequence. The fragment-probe mixture is then fed into a thermodynamics-based hybridization model (SantaLucia & Hicks, 2004). This model predicts all possible stable probe-bacteria fragment bindings along with their resulting concentrations for a given set of experimental conditions (FIGS. 2B-C). The overall hybridization affinity $\varphi_{ij}$ is computed by summing the concentrations of all predicted and stable probe-fragment bindings for a unit concentration of bacterial genome.

Due to an excess concentration of probes as compared to sample DNA, the probe-binding vector y can be closely approximated as a linear combination of the predicted hybridization affinities of the species in the reference genome database (the columns of the matrix) weighted by their concentrations x; i.e., y=Φx+n, where the vector n accounts for noise and modeling errors (FIG. 1C) (see Example 1).

Two key capabilities of the UMD platform are to (i) detect the presence and (ii) estimate the concentrations x of a potentially large number N of reference microbial genomes in an infectious sample given only a small number M of probe-binding measurements y. Simply inverting the matrix is impossible in this case, since it has many more columns than rows. Fortunately, it is reasonable to assume that only a small number K of microbial genomes will be present in a given sample, in which case the concentration vector x is sparse, with K nonzero and N−K zero (or close to zero) entries; when K<M, one can hope to invert to estimate the K nonzero concentrations. More rigorously (see the Supplementary Materials for details), when the columns of Φ are sufficiently incoherent (close to orthogonal) and when M=cK log(N/K), where c is a small constant, the inventors can apply the theory of compressive sensing (Donoho, 2006 and Baraniuk, 2007) to recover the concentrations x from the measurements y via a sparse optimization of the form $$\min_x \|x\|_0, \text{ subject to } \|y - \Phi x\|_2 < \sigma.$$

Figure 2:
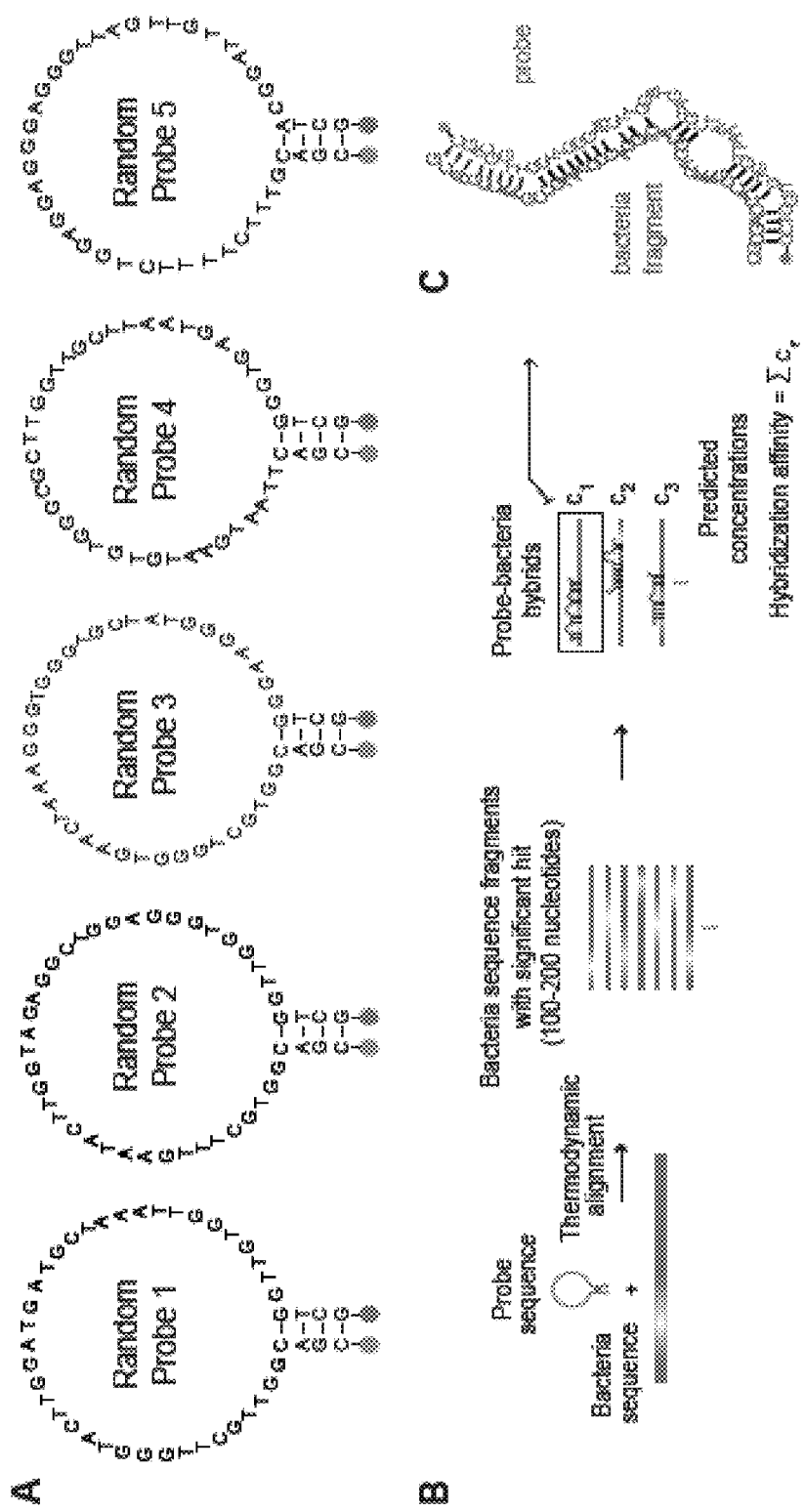
FIGS. 2A-C. Random probe design and hybridization affinity computation process.
Figure 3:
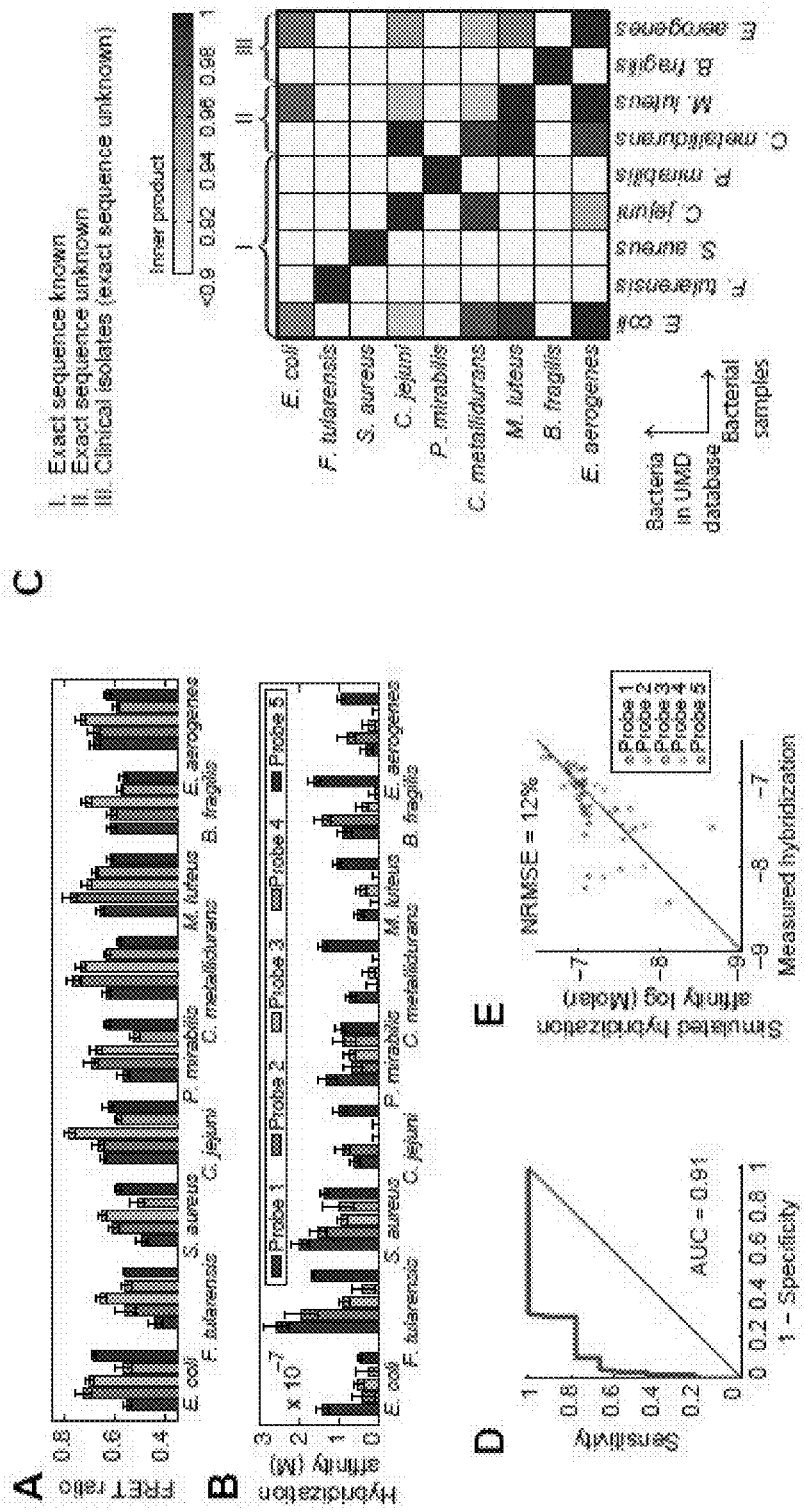
FIGS. 3A-E. Binding patterns of five random probes correctly identifies the bacteria present in nine diverse bacterial samples.
Figure 4:
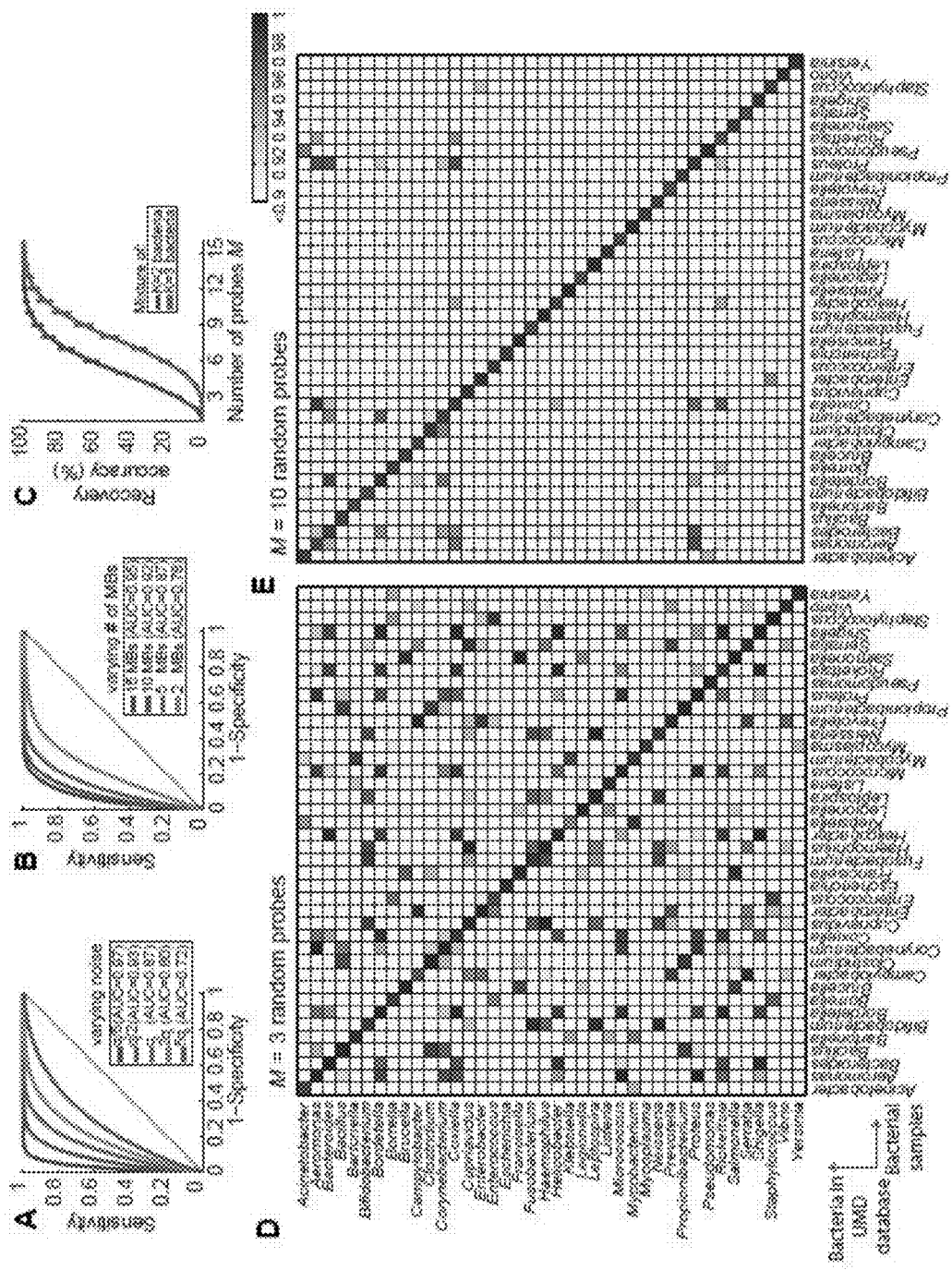
FIGS. 4A-E. Performance of UMD platform in genus-level recovery of 40 species listed as the most common human infectious genera by Centers for Disease Control and Prevention (CDC) with different number of random probes M and noise variance $\sigma$.

Here, $\|x\|_0$ counts the number of non-zero values in the vector x, and σ bounds the energy of the noise vector n. Since M=cK log(N/K) scales logarithmically with N, the UMD platform has the potential to identify and estimate the concentrations of a large number N of potential microbial genomes using only a small number M of measurement probes. To ensure that the columns of Φ are incoherent, the inventors use DNA probes whose sequences are generated via a random permutation of nucleotides (FIG. 2A). The inventors have demonstrated that a small fixed set of randomly selected probes induce sufficiently incoherent hybridization patterns across the columns of Φ and enable us to screen for a group of pathogenic organisms in vitro (FIG. 3). In addition, the inventors showcased the average performance of several sets of randomly selected probes in universal pathogenic detection in silico (FIG. 4).

This universal sensing strategy can take on any physical embodiment (e.g., quantitative real-time PCR, DNA microarray, or WGS) for the detection of any DNA sequence (bacterial, viral, or fungal). To test and validate the concept, the inventors recovered pathogenic bacteria using random probes in the form of mismatch-tolerant Sloppy Molecular Beacons (Sloppy MBs) (Chakravorty et al., 2010). In a conventional MB (Tyagi & Kramer, 1996) for bacterial detection, the loop sequence is designed to target specific regions (e.g., 16S rDNA) within a single bacterium (Dark et al., 2009) or multiple bacteria (Chakravorty et al., 2010).

In the MB probes for UMD, the loop sequence is selected as a random sequence (FIG. 2A, FIG. 5, and Example 1) of length 38 nts, and the 4 nt-long stem sequence is consistent across all probes, although other choices might be utilized (different design tradeoffs are discussed elsewhere (Sheikh, 2010)). The unusually long loop and short stem enable the random probes to form hybrids with several base pair mismatches across the entire bacterial genome and compensate for the lower signal intensity in the absence of DNA amplification methods such as PCR (FIG. 2C).

II. INCOHERENT SENSOR SELECTION (INSENSE)

The accelerating demand for capturing signals at high resolution is driving acquisition systems to employ an increasingly large number of sensing units. However, factors like manufacturing costs, physical limitations, and energy constraints typically define a budget on the total number of sensors that can be implemented in a given system. This budget constraint motivates the design of "sensor selection" algorithms (Joshi & Boyd, 2009) that intelligently select a subset of sensors from a pool of available sensors in order to lower the sensing cost with only a small deterioration in acquisition performance.

The inventors extend the classical sensor selection setup, where D available sensors obtain linear measurements of a signal $x \in \mathbb{R}^N$ according to $y=\Phi x$ with each row of $\Phi \in \mathbb{R}^{D \times N}$ corresponding to one sensor. In this setup, the sensor selection problem is one of finding a subset $\Omega$ of sensors (i.e., rows of $\Phi$) of size $|\Omega|=M$ such that the signal x can be recovered from its M linear measurements $$y_\Omega = \Phi_\Omega x \quad (1)$$

with minimal reconstruction error. Here, $\Phi_\Omega \in \mathbb{R}^{M \times N}$ is called the sensing matrix; it contains the rows of $\Phi$ indexed by $\Omega$.

The lion's share of current sensor selection algorithms (Joshi & Boyd, 2009; Shamaiah et al., 2010; Ranieri et al., 2014) select sensors that best recover an arbitrary signal x from M>N measurements. In this case, (1) is overdetermined. Given a subset of sensors $\Omega$, the signal x is recovered simply by inverting the sensing matrix while computing $\Phi^\dagger_\Omega y_\Omega$, where $\Phi_\Omega^\dagger$ is the pseudoinverse of $\Phi_\Omega$.

Such approaches do not exploit the fact that many real-world signals are (near) sparse in some basis (Candes & Wakin, 2008). It is now well-known that (near) sparse signals can be accurately recovered from a number of linear measurements M«N using sparse recovery/compressive sensing (CS) techniques (Donoho, 2006; Baraniuk, 2007; Candes, 2006). Conventional sensor selection algorithms are not designed to exploit low-dimensional signal structure. Indeed, they typically fail to select the appropriate sensors for sparse signals in this underdetermined setting (M<N).

The inventors developed a new sensor selection framework that finds the optimal subset of sensors that best recovers a (near) sparse signal x from M<N linear measurements (see FIG. 15). In contrast to the conventional sensor selection setting, here the sensing equation (1) is underdetermined, and it cannot be simply inverted in closed form.

A key challenge in sensor selection in the underdetermined setting is that one must replace the cost function that has been so useful in the classical, overdetermined setting, namely the estimation error $\|x-\hat{x}\|_2^2$ (or the covariance of the estimation error in the presence of noise). In the overdetermined setting, this error can be obtained in closed form simply by inverting equation (1). In the underdetermined setting, this error has no closed form expression. Indeed, recovery of a sparse vector x from $y_\Omega$ requires a computational scheme (Tibshirani, 1996; Donoho et al., 2009).

Fortunately, the sparse recovery theory tells us that one can reliably recover a sufficiently sparse vector x from its linear measurements $y_\Omega$ when the columns of the sensing matrix $\Phi_\psi$ are sufficiently incoherent (Tropp, 2004; Donoho et al., 2006; Herzet et al., 2013). Define the coherence between the columns $\phi_i$ and $\phi_j$ in the sensing matrix $\Phi_\psi$ as $$\mu_{ij}(\Phi_\Omega) = \frac{|\langle \phi_i, \phi_j \rangle|}{\|\phi_i\| \|\phi_j\|}.$$

If the values of $\mu_{ij}(\Phi_\psi)$ for all pairs of columns (i, j) are bounded by a certain threshold, then sparse recovery algorithms such as Basis Pursuit (BP) (Tropp, 2004; Candes et al., 2006; Gribonval & Vandergheynst, 2006) can recover the sparse signal x exactly. This theory suggests a new cost function for sensor selection. To select the sensors ψ that reliably recover a sparse vector, one can minimize the average squared coherence:

$$\mu_{avg}^2(\Phi_\Omega) = \frac{1}{\binom{N}{2}} \sum_{1 \le i < j \le N} \mu_{ij}^2(\Phi_\Omega). \quad (2)$$

The challenge now becomes formulating an optimization algorithm that selects the subset of the rows of (Φ) (the sensors) whose columns have the smallest average squared coherence.

The inventors are the first to propose and study the sparse-signal sensor selection problem. Below it is demonstrated that the standard cost functions used in overdetermined sensor selection algorithms are not suitable for the underdetermined case. To solve this problem, the inventors developed a new sensor selection algorithm that optimizes the new cost function (2); call it the "Incoherent Sensor Selection" (Insense) algorithm. Insense employs an efficient optimization technique to find a subset of sensors with smallest average coherence among the columns of the selected sensing matrix $\Phi_\Omega$. The optimization technique— projection onto the convex set defined by a scaled-boxed simplex (SBS) constraint—is of independent interest. The codes for the Insense algorithm are available on the world wide web at github.com/amirmohan/Insense.git, which are incorporates be reference herein in their entirety.

The inventors also demonstrate the superior performance of Insense over conventional sensor selection algorithms using an exhaustive set of experimental evaluations that include real-world datasets from microbial diagnostics and six performance metrics: average mutual coherence, maximum mutual coherence, sparse recovery performance, frame potential, condition number, and running time. For the kinds of redundant, coherent, or structured $\Phi$ that are common in real-world applications, Insense finds the best subset of sensors in terms of sparse recovery performance by a wide margin. Indeed, in these cases, many conventional sensor selection algorithms fail completely.

A. Conventional Sensor Selection Algorithms

Existing sensor selection algorithms mainly study the sensor selection problem in the overdetermined regime (when M≥N) (Joshi & Boyd, 2009; Shamaiah et al., 2010; Ranieri et al., 2014; Ranieri et al., 2012).

In the overdetermined regime, robust signal recovery can be obtained using the solution to the least squares (LS) problem in the sensing model (1), which motivates as a cost function the mean squared error (MSE) (Das & Kempe, 2008; Golovin et al., 2010; Das & Kempe, 2011) or a proxy of the MSE (Steinberg & Hunter, 1984; Krause et al., 2008; Wang et al., 2004) of the LS solution.

For instance, Joshi & Boyd (2009) employ a convex optimization-based algorithm to minimize the log-volume of the confidence ellipsoid around the LS solution of x. Shamaiah et al. (2010) develop a greedy algorithm that outperforms the convex approach in terms of MSE. FrameSense (Ranieri et al., 2014) minimize the frame potential (FP) of the selected matrix:

$$FP(\Phi_\Omega) = \sum_{\forall (i,j) \in \Omega, i<j} |\langle \phi^i, \phi^j \rangle|^2, \quad (3)$$

where $\phi^i$ represents the $i^{th}$ row of $\Phi$. Several additional sensor selection algorithms that assume a non-linear observation model (Ford et al., 1989; Chepuri & Leus, 2015) also operate only in the overdetermined regime.

B. Connections to Compressive Sensing

The inventor's model for sensor selection has strong connections to, and enables powerful extensions of, the CS problem, in which a (near) sparse signal is recovered from a small number of randomized linear measurements (Donoho, 2006; Baraniuk, 2007; Candes, 2006). First, note that CS theory typically employs random sensing matrices; for instance it has been shown that many ensembles of random matrices, including partial Fourier, Bernoulli, and Gaussian matrices, result in sensing matrices with guaranteed sparse recovery (Needell & Vershynin, 2009; Needell & Vershynin, 2010). Recently, there have been efforts to design sensing matrices that outperform random matrices for certain recovery tasks (Amini & Marvasti, 2011; Strohmer & Heath, 2003; Tropp et al., 2005; Elad, 2007; Duarte-Carvajalino & Sapiro, 2009). For instance, Grassmannian matrices (Strohmer & Heath, 2003) attain the smallest possible mutual coherence and hence can lead to better performance in some applications.

However, many real-world applications do not involve random or Grassmannian sensing matrices; rather the sensing matrix is dictated by physical constraints that are specific and unique to each application. For example, in the sparse microbial diagnostic problem (Aghazadeh et al., 2016, which is incorporated herein by reference in its entirety), the entries of the sensing matrix $\Phi$ are determined by the hybridization affinity of random DNA probes to microbial genomes and do not necessarily follow a random distribution. A key outcome of this work is a new approach to construct practical and realizable sensing matrices using underdetermined sensor selection (via Insense).

C. Problem Statement

Consider a set of D sensors taking nonadaptive, linear measurements of a K-sparse (i.e., with K non-zero elements) vector $x \in \mathbb{R}^N$ following the linear system y=$\Phi$x, where $\Phi \in \mathbb{R}^{D \times N}$ is a given sensing matrix. The aim is to select a subset $\Omega$ of sensors of size $|\Omega|$=M≪D, such that the sparse vector x can be recovered from the resulting M<N linear measurements $y_\Omega = \Phi_\Omega x$ with minimal reconstruction error. Here, $\Phi_\Omega$ contains the rows of $\Phi$ indexed by $\Omega$, and $y_\Omega$ contains the entries of y indexed by $\Omega$. This model for the sensor selection problem can be adapted to more general scenarios. For example, if the signal is sparse in a basis $\Psi$, then simply consider $\Phi = \Theta \Psi$ as the new sensing matrix, where $\Theta$ is the original sensing matrix.

In order to find a subset $\Omega$ of sensors (rows of $\Phi$) that best recovers a sparse signal x from $y_\Omega$ (or find one of the solutions if many solutions exist), the aim is to select a submatrix $\Phi_\Omega \in \mathbb{R}^{M \times N}$ that attains the lowest average squared coherence:

$$\mu_{avg}^2(\Phi_\Omega) = \frac{1}{\binom{N}{2}} \sum_{1 \le i < j \le N} \frac{|\langle \phi_i, \phi_j \rangle|^2}{\|\phi_i\|^2 \|\phi_j\|^2}, \quad (4)$$

where $\phi_i$ denotes the $i^{th}$ column of $\Phi_\Omega$. The term $\mu_{avg}$ averages the off-diagonal entries of $\Phi_\Omega^T \Phi_\Omega$ (indexed by $1 \le i \le j \le N$) after column normalization. Other measures of coherence (e.g., max coherence $$\mu_{max}(\Phi_\Omega) = \max_{i<j} \mu_{ij})$$

can also be employed by slightly modifying the optimization procedure developed below. The inventors choose to work with average coherence due to its simplicity and the fact that their experiments show that its performance is comparable to max coherence.

Define the diagonal selector matrix Z=diag(z) with z=[Z1, Z2, Z3, . . . , ZD]$^T$ and $z_i \in \{0, 1\}$, where $z_i$=1 indicates that the $i^{th}$ row (sensor) in $\Phi$ is selected and $z_i$=0 otherwise. This enables us to formulate the sensor selection problem as the following optimization problem:

$$\underset{z \in \{0,1\}^D}{\text{minimize}} \sum_{1 \le i < j \le N} \frac{G_{ij}^2}{G_{ii} G_{jj}}, \quad (5)$$

$$\text{s.t.} \quad G = \Phi^T Z \Phi, \quad 1^T z = M,$$

where 1 is the all-ones vector. This Boolean optimization problem is combinatorial, since one needs to search over $$\binom{D}{M}$$

combinations of sensors to find the optimal set $\Omega$.

To overcome this complexity, the inventors relax the Boolean constraint on $z_i$ to the box constraint $z_i \in [0, 1]$ to arrive at the following problem:

$$\underset{z \in [0,1]^D}{\text{minimize}} \sum_{1 \le i \le j \le N} \frac{|G_{ij}|^2}{G_{ii}G_{jj}}, \qquad (6)$$

$$\text{s.t.} \quad G = \Phi^T Z \Phi, \, 1^T z = M,$$

which supports an efficient gradient-projection algorithm to find an approximate solution. This algorithm is developed next.

D. The Insense Algorithm

The steps that Insense takes to solve the problem (6) are outlined below. The objective of (6) is slightly modified to:

$$f_\epsilon(z) = \sum_{1 \le i \le j \le N} \frac{G_{ij}^2 + \epsilon_1}{G_{ii}G_{jj} + \epsilon_2} \text{ where } G = \Phi^T Z \Phi, \qquad (7)$$

where the small positive constants $\epsilon_2 < \epsilon_1 \ll 1$ make the objective well-defined and bounded over $z \in [0, 1]^D$.

The objective function (7) is smooth and differentiable but non-convex; the box constraints on z are linear. The objective is minimized using the iterative gradient-projection algorithm outlined in Alg. 1 (FIG. 16). The gradient $\nabla_z f \in \mathbb{R}^D$ can be computed using the multidimensional chain rule of derivatives (Petersen & Pedersen, 2008) as:

The N×N upper triangular matrix $\nabla_G f$ is the gradient of f in terms of the (auxiliary) variable G at the point $G = \Phi^T Z \Phi$, given by:

$$(\nabla_G f)_{ij} = \begin{cases} \frac{2G_{ij}}{G_{ii}G_{jj} + \epsilon_2}, & i < j \\ -\sum_{\forall l \ne i} \frac{G_{il}(G_{il}^2 + \epsilon_1)}{(G_{ii}G_{ll} + \epsilon_2)^2}, & i = j \\ 0, & \text{elsewhere.} \end{cases} \qquad (8)$$

The Insense algorithm (Alg. 1; FIG. 16) proceeds as follows. First, the variables G and z are initialized. Next, the following update is performed in iteration k:

$$z^{k+1} = P_{SBS}(z^k - \gamma^k \nabla f(z^k)),$$

where $P_{SBS}$ denotes the projection onto the convex set defined by the scaled boxed-simplex (SBS) constraints $1^T z = M$ and $z \in [0, 1]^D$. For certain bounded step size rules (e.g., $\gamma^k \le 1/L$, where L is the Lipschitz constant of $\nabla_z f$), the sequence $\{z^k\}$ generated by (9) converges to a critical point of the nonconvex problem (Attouch et al., 2013; Nesterov, 2007). In this implementation, the inventors use a backtracking line search to determine $\gamma^k$ in each step (Nesterov, 2007).

E. The SBS projection

This section details the inventor's approach to solving the SBS projection problem:

$$\underset{z}{\text{minimize}} \, \frac{1}{2} \|z - y\|_2^2, \qquad (10)$$

$$\text{subject to} \sum_i z_i = M \text{ and } z_i \in [0, 1] \, \forall \, i = 1, \ldots, D.$$

For M>1, the SBS projection problem is significantly different from the (scaled-)simplex constraint ($\Sigma_i z_i = M$) projection problem that has been studied in the literature (Chen & Ye, 2011; Wang & Carreira-Perpinan, 2013; Condat, 2014), due to the additional box constraints $z_i \in [0, 1]$.

The Lagrangian of the problem (10) can be written as:

$$f(z, \lambda, \alpha, \beta) = \frac{1}{2}\|z - y\|_2^2 + \lambda\left(\sum_i z_i - M\right) + \sum_i \alpha_i(-z_i) + \sum_i \beta_i(z_i - 1),$$

where $\lambda, \alpha, \beta$ are Lagrange multipliers for the equality and inequality constraints, respectively. The Karush-Kuhn-Tucker (KKT) conditions are given by:

$$z_i - y_i + \lambda - \alpha_i + \beta_i = 0, \, \forall \, i, \, \sum_i z_i - M = 0,$$

$$\alpha_i(-z_i) = 0, \, \beta_i(z_i - 1) = 0, \, \alpha_i, \beta_i \ge 0, \, 0 \le z_i \le 1, \, \forall \, i.$$

According to the complimentary slackness condition for the box constraint $z_i \in [0, 1]$, there are the following three cases for $x_i$:

(a) $z_i = 0$: $\beta_i = 0$, $\alpha_i = y_i + \lambda > 0$,
(b) $z_i = 1$: $\alpha_i = 0$, $\beta_i = 1 - y_i - \lambda > 0$,
(c) $z_i \in [0, 1]$: $a_i = \beta_i = 0$, $z_i = y_i + \lambda$.

Therefore, the value of $\lambda$ holds the key to the proximal problem (10). However, finding $\lambda$ is not an easy task, since it is not known which entries of z will fall on the boundary of the box constraint (and are equal to either 0 or 1).

Similarly, the entries in z that are equal to 1 can be found by negating z and y in (10). Let p=−y and assume that its entries are sorted in ascending order; a procedure similar to that above shows that the entries in z that are equal to 1 correspond to the first $K_1$ entries in p, where $K_i$ is the largest integer K such that $\Sigma_i \max(\min(p_i - p_K - 1, 0), -1) \ge -M$.

Knowing which entries in z are equal to 0 and 1, the value of $\lambda$ can be solved for by working with the entries with values in (0, 1). Using case (c) above and denoting the index set of these entries by $\zeta$ one has:

$$\lambda = \frac{M - K_1 - \sum_{i \in \zeta} y_i}{|\zeta|},$$

and the solution to (10) is given by $z_i = \max(\min(y_i + \lambda, 1), 0)$. as a space between the peptidoglycan and the outer cell membrane called the periplasmic space. Gram-negative bacterial generally do not have teichoic acids or lipoteichoic acids in their outer coating. Generally, Gram-negative bacteria also release some endotoxin and contain prions which act as molecular transport units for specific compounds. Most bacteria are Gram-negative. Some non-limiting examples of Gram-negative bacteria include *Bordetella*,

*Borrelia, Burcelia, Campylobacteria, Escherichia, Francisella, Haemophilus, Helicobacter, Legionella, Leptospira, Neisseria, Pseudomonas, Rickettsia, Salmonella, Shigella, Treponema, Vibrio,* and *Yersinia.*

C. Gram-Indeterminate Bacteria

In some aspects of the present disclosure, the compounds disclosed herein may be used to detect a bacterial infection by a Gram-indeterminate bacteria. Gram-indeterminate bacteria do not full stain or partially stain when exposed to crystal violet. Without being bound by theory, a Gram-indeteriminate bacteria may exhibit some of the properties of the Gram-positive and Gram-negative bacteria. A non-limiting example of a Gram-indeterminate bacteria include *Mycobacterium tuberculosis* or *Mycobacterium leprae.*

D. Staphylococcus Aureus

*Staphylococcus aureus* is a gram-positive, round-shaped bacterium that is a member of the Firmicutes, and is frequently found in the nose, respiratory tract, and on the skin. It is often positive for catalase and nitrate reduction and is a facultative anaerobe that can grow without the need for oxygen. Although *S. aureus* is not always pathogenic, it is a common cause of skin infections such as a skin abscess, respiratory infections such as sinusitis, and food poisoning. Pathogenic strains often promote infections by producing virulence factors such as potent protein toxins, and the expression of cell-surface proteins that bind and inactivate antibodies. The emergence of antibiotic-resistant strains of *S. aureus* such as methicillin-resistant *S. aureus* (MRSA) is a worldwide problem in clinical medicine. Despite much research and development there is no approved vaccine for *S. aureus.*

An estimated 20% of the human population are long-term carriers of *S. aureus* which can be found as part of the normal skin flora, in the nostrils, and as a normal inhabitant of the lower reproductive tract of women *S. aureus* can cause a range of illnesses, from minor skin infections, such as acne, impetigo, boils, cellulitis, folliculitis, carbuncles, scalded skin syndrome, and abscesses, to life-threatening diseases such as pneumonia, meningitis, osteomyelitis, endocarditis, toxic shock syndrome, bacteremia, and sepsis. It is still one of the five most common causes of hospital-acquired infections and is often the cause of wound infections following surgery. Each year, around 500,000 patients in hospitals of the United States contract a staphylococcal infection, chiefly by *S. aureus.*

*S. aureus* is a facultative anaerobic, gram-positive coccal (round) bacterium also known as "golden staph" and "oro staphira." *S. aureus* is non-motile and does not form spores. In medical literature, the bacterium is often referred to as *S. aureus, Staph aureus,* or *Staph A. S. aureus* appears as staphylococci (grape-like clusters) when viewed through a microscope, and has large, round, golden-yellow colonies, often with hemolysis, when grown on blood agar plates. *S. aureus* reproduces asexually by binary fission. Complete separation of the daughter cells is mediated by *S. aureus* autolysin, and in its absence or targeted inhibition, the daughter cells remain attached to one another and appear as clusters.

*S. aureus* is catalase-positive (meaning it can produce the enzyme catalase). Catalase converts hydrogen peroxide ($H_2O_2$) to water and oxygen. Catalase-activity tests are sometimes used to distinguish staphylococci from enterococci and streptococci. Previously, *S. aureus* was differentiated from other staphylococci by the coagulase test. However, not all *S. aureus* strains are coagulase-positive and incorrect species identification can impact effective treatment and control measures.

1. Role in Disease

While *S. aureus* usually acts as a commensal bacterium, asymptomatically colonizing about 30% of the human population, it can sometimes cause disease. In particular, *S. aureus* is one of the most common causes of bacteremia and infective endocarditis. Additionally, it can cause various skin and soft tissue infections, particularly when skin or mucosal barriers have been breached.

*S. aureus* infections can spread through contact with pus from an infected wound, skin-to-skin contact with an infected person, and contact with objects used by an infected person such as towels, sheets, clothing, or athletic equipment. Joint replacements put a person at particular risk of septic arthritis, staphylococcal endocarditis (infection of the heart valves), and pneumonia.

Skin infections are the most common form of *S. aureus* infection. This can manifest in various ways, including small benign boils, folliculitis, impetigo, cellulitis, and more severe, invasive soft-tissue infections.

*S. aureus* is extremely prevalent in persons with atopic dermatitis. It is mostly found in fertile, active places, including the armpits, hair, and scalp. Large pimples that appear in those areas may exacerbate the infection if lacerated. This can lead to staphylococcal scalded skin syndrome, a severe form of which can be seen in neonates.

The presence of *S. aureus* in persons with atopic dermatitis is not an indication to treat with oral antibiotics, as evidence has not shown this to give benefit to the patient. The relationship between *S. aureus* and atopic dermatitis is unclear.

*S. aureus* is also responsible for food poisoning. It is capable of generating toxins that produce food poisoning in the human body. Its incubation period lasts one to six hours, with the illness itself lasting anywhere from thirty minutes to three days.

*S. aureus* is the bacterium that is commonly responsible for all major bone and joint infections. This manifests in one of three forms: osteomyelitis, septic arthritis and infection from a replacement joint surgery.

*S. aureus* is a leading cause of bloodstream infections throughout much of the industrialized world. Infection is generally associated with breakages in the skin or mucosal membranes due to surgery, injury, or use of intravascular devices such as catheters, hemodialysis machines, or injected drugs. Once the bacteria have entered the bloodstream, they can infect various organs, causing infective endocarditis, septic arthritis, and osteomyelitis. This disease is particularly prevalent and severe in the very young and very old.

Without antibiotic treatment, *S. aureus* bacteremia has a case fatality rate around 80%. With antibiotic treatment, case fatality rates range from 15% to 50% depending on the age and health of the patient, as well as the antibiotic resistance of the *S. aureus* strain.

2. Diagnosis

Depending upon the type of infection present, an appropriate specimen is obtained accordingly and sent to the laboratory for definitive identification by using biochemical or enzyme-based tests. A Gram stain is first performed to guide the way, which should show typical gram-positive bacteria, cocci, in clusters. Second, the isolate is cultured on mannitol salt agar, which is a selective medium with 7-9% NaCl that allows *S. aureus* to grow, producing yellow-colored colonies as a result of mannitol fermentation and subsequent drop in the medium's pH.

Furthermore, for differentiation on the species level, catalase (positive for all *Staphylococcus* species), coagulase (fibrin clot formation, positive for *S. aureus*), DNAse (zone of clearance on DNase agar), lipase (a yellow color and rancid odor smell), and phosphatase (a pink color) tests are all done. For staphylococcal food poisoning, phage typing can be performed to determine whether the staphylococci recovered from the food were the source of infection.

Diagnostic microbiology laboratories and reference laboratories are key for identifying outbreaks and new strains of *S. aureus*. Recent genetic advances have enabled reliable and rapid techniques for the identification and characterization of clinical isolates of *S. aureus* in real time. These tools support infection control strategies to limit bacterial spread and ensure the appropriate use of antibiotics. Quantitative PCR is increasingly being used to identify outbreaks of infection.

When observing the evolution of *S. aureus* and its ability to adapt to each modified antibiotic, two basic methods known as "band-based" or "sequence-based" are employed. Keeping these two methods in mind, other methods such as multilocus sequence typing (MLST), pulsed-field gel electrophoresis (PFGE), bacteriophage typing, spa locus typing, and SCCmec typing are often conducted more than others. With these methods, it can be determined where strains of MRSA originated and also where they are currently.

With MLST, this technique of typing uses fragments of several housekeeping genes known as aroE, glpF, gmk, pta, tip, and yqiL. These sequences are then assigned a number which give to a string of several numbers that serve as the allelic profile. Although this is a common method, a limitation about this method is the maintenance of the microarray which detects newly allelic profiles, making it a costly and time-consuming experiment.

With PFGE, a method which is still very much used dating back to its first success in 1980s, remains capable of helping differentiate MRSA isolates. To accomplish this, the technique uses multiple gel electrophoresis, along with a voltage gradient to display clear resolutions of molecules. The *S. aureus* fragments then transition down the gel, producing specific band patters that are later compared with other isolates in hopes of identifying related strains. Limitations of the method include practical difficulties with uniform band patterns and PFGE sensitivity as a whole.

Spa locus typing is also considered a popular technique that uses a single locus zone in a polymorphic region of *S. aureus* to distinguish any form of mutations. Although this technique is often inexpensive and less time-consuming, the chance of losing discriminatory power makes it hard to differentiate between MLST CCs exemplifies a crucial limitation.

3. Treatment

The treatment of choice for *S. aureus* infection is penicillin, though nearly all human strains are now resistant to this antimicrobial agent. An antibiotic derived from some *Penicillium* fungal species, penicillin inhibits the formation of peptidoglycan cross-linkages that provide the rigidity and strength in a bacterial cell wall. The four-membered β-lactam ring of penicillin is bound to enzyme DD-transpeptidase, an enzyme that when functional, cross-links chains of peptidoglycan that form bacterial cell walls. The binding of β-lactam to DD-transpeptidase inhibits the enzyme's functionality and it can no longer catalyze the formation of the cross-links. As a result, cell wall formation and degradation are imbalanced, thus resulting in cell death. In most countries, however, penicillin resistance is extremely common, and first-line therapy is most commonly a penicillinase-resistant β-lactam antibiotic (for example, oxacillin or flucloxacillin, both of which have the same mechanism of action as penicillin). Combination therapy with gentamicin may be used to treat serious infections, such as endocarditis, but its use is controversial because of the high risk of damage to the kidneys. Honey and propolis produced by the South American bee *Tetragonisca angustula* has also been found to have antibacterial activity towards *S. aureus*. The duration of treatment depends on the site of infection and on severity.

Antibiotic resistance in *S. aureus* was uncommon when penicillin was first introduced in 1943, but by 1950, 40% of hospital *S. aureus* isolates were penicillin-resistant; by 1960, this had risen to 80%. Today, MRSA is one of a number of greatly feared strains of *S. aureus* which have become resistant to most β-lactam antibiotics. For this reason, vancomycin, a glycopeptide antibiotic, is commonly used to combat MRSA. Vancomycin inhibits the synthesis of peptidoglycan, but unlike β-lactam antibiotics, glycopeptide antibiotics target and bind to amino acids in the cell wall, preventing peptidoglycan cross-linkages from forming. MRSA strains are most often found associated with institutions such as hospitals, but are becoming increasingly prevalent in community-acquired infections. A recent study by the Translational Genomics Research Institute showed that nearly half (47%) of the meat and poultry in U.S. grocery stores were contaminated with *S. aureus*, with more than half (52%) of those bacteria resistant to antibiotics. This resistance is commonly caused by the widespread use of antibiotics in the husbandry of livestock, including prevention or treatment of an infection, as well as promoting growth.

Researchers from ETH Zurich have created the endolysin Staphefekt SA.100, which is active against *S. aureus*, including MRSA. Minor skin infections can be treated with triple antibiotic ointment.

E. *E. Coli*

*Escherichia coli* is a gram-negative, facultatively anaerobic, rod-shaped, coliform bacterium of the genus *Escherichia* that is commonly found in the lower intestine of warm-blooded organisms (endotherms). Most *E. coli* strains are harmless, but some serotypes can cause serious food poisoning in their hosts, and are occasionally responsible for product recalls due to food contamination. The harmless strains are part of the normal flora of the gut, and can benefit their hosts by producing vitamin $K_2$, and preventing colonization of the intestine with pathogenic bacteria. *E. coli* is expelled into the environment within fecal matter. The bacterium grows massively in fresh fecal matter under aerobic conditions for 3 days, but its numbers decline slowly afterwards.

*E. coli* and other facultative anaerobes constitute about 0.1% of gut flora, and fecal-oral transmission is the major route through which pathogenic strains of the bacterium cause disease. Cells are able to survive outside the body for a limited amount of time, which makes them potential indicator organisms to test environmental samples for fecal contamination. A growing body of research, though, has examined environmentally persistent *E. coli* which can survive for extended periods outside of a host.

The bacterium can be grown and cultured easily and inexpensively in a laboratory setting, and has been intensively investigated for over 60 years. *E. coli* is a chemoheterotroph whose chemically defined medium must include a source of carbon and energy. *E. coli* is the most widely studied prokaryotic model organism, and an important species in the fields of biotechnology and microbiology, where it has served as the host organism for the majority of work with recombinant DNA. Under favorable conditions, it takes only 20 minutes to reproduce.

*E. coli* and related bacteria possess the ability to transfer DNA via bacterial conjugation or transduction, which allows genetic material to spread horizontally through an existing population. The process of transduction, which uses the bacterial virus called a bacteriophage, is where the spread of the gene encoding for the Shiga toxin from the *Shigella* bacteria to *E. coli* helped produce *E. coli* O157:H7, the Shiga toxin-producing strain of *E. coli*.

*E. coli* encompasses an enormous population of bacteria that exhibit a very high degree of both genetic and phenotypic diversity. Genome sequencing of a large number of isolates of *E. coli* and related bacteria shows that a taxonomic reclassification would be desirable. However, this has not been done, largely due to its medical importance, and *E. coli* remains one of the most diverse bacterial species: only 20% of the genes in a typical *E. coli* genome is shared among all strains. In fact, from the evolutionary point of view, the members of genus *Shigella* (*S. dysenteriae, S. flexneri, S. boydii*, and *S. sonnei*) should be classified as *E. coli* strains, a phenomenon termed taxa in disguise. Similarly, other strains of *E. coli* (e.g., the K-12 strain commonly used in recombinant DNA work) are sufficiently different that they would merit reclassification.

1. Serotypes

A common subdivision system of *E. coli*, but not based on evolutionary relatedness, is by serotype, which is based on major surface antigens (O antigen: part of lipopolysaccharide layer; H: flagellin; K antigen: capsule), e.g., O157:H7). It is, however, common to cite only the serogroup, i.e., the O-antigen. At present, about 190 serogroups are known. The common laboratory strain has a mutation that prevents the formation of an O-antigen and is thus not typeable.

2. Genome Plasticity and Evolution

Like all lifeforms, new strains of *E. coli* evolve through the natural biological processes of mutation, gene duplication, and horizontal gene transfer; in particular, 18% of the genome of the laboratory strain MG1655 was horizontally acquired since the divergence from *Salmonella*. *E. coli* K-12 and *E. coli* B strains are the most frequently used varieties for laboratory purposes. Some strains develop traits that can be harmful to a host animal. These virulent strains typically cause a bout of diarrhea that is often self-limiting in healthy adults but is frequently lethal to children in the developing world. More virulent strains, such as O157:H7, cause serious illness or death in the elderly, the very young, or the immunocompromised.

The genera *Escherichia* and *Salmonella* diverged around 102 million years ago (credibility interval: 57-176 mya) which coincides with the divergence of their hosts: the former being found in mammals and the latter in birds and reptiles. This was followed by a split of an *Escherichia* ancestor into five species (*E. albertii, E. coli, E. fergusonii, E. hermannii*, and *E. vulneris*). The last *E. coli* ancestor split between 20 and 30 million years ago.

*E. coli* belongs to a group of bacteria informally known as coliforms that are found in the gastrointestinal tract of warm-blooded animals. *E. coli* normally colonizes an infant's gastrointestinal tract within 40 hours of birth, arriving with food or water or from the individuals handling the child. In the bowel, *E. coli* adheres to the mucus of the large intestine. It is the primary facultative anaerobe of the human gastrointestinal tract. As long as these bacteria do not acquire genetic elements encoding for virulence factors, they remain benign commensals.

3. Role in Disease

Most *E. coli* strains do not cause disease, but virulent strains can cause gastroenteritis, urinary tract infections, and neonatal meningitis. It can also be characterized by severe abdominal cramps, diarrhea that typically turns bloody within 24 hours, and sometimes fever. In rarer cases, virulent strains are also responsible for bowel necrosis (tissue death) and perforation without progressing to hemolytic-uremic syndrome, peritonitis, mastitis, septicemia, and gram-negative pneumonia.

There is one strain, *E. coli* #0157:H7, that produces the Shiga toxin (classified as a bioterrorism agent). This toxin causes premature destruction of the red blood cells, which then clog the body's filtering system, the kidneys, causing hemolytic-uremic syndrome (HUS). This in turn causes strokes due to small clots of blood which lodge in capillaries in the brain. This causes the body parts controlled by this region of the brain not to work properly. In addition, this strain causes the buildup of fluid (since the kidneys do not work), leading to edema around the lungs and legs and arms. This increase in fluid buildup especially around the lungs impedes the functioning of the heart, causing an increase in blood pressure.

Uropathogenic *E. coli* (UPEC) is one of the main causes of urinary tract infections. It is part of the normal flora in the gut and can be introduced in many ways. In particular for females, the direction of wiping after defecation (wiping back to front) can lead to fecal contamination of the urogenital orifices. Anal intercourse can also introduce this bacterium into the male urethra, and in switching from anal to vaginal intercourse, the male can also introduce UPEC to the female urogenital system. For more information, see the databases at the end of the article or UPEC pathogenicity.

In May 2011, one *E. coli* strain, O104:H4, was the subject of a bacterial outbreak that began in Germany. Certain strains of *E. coli* are a major cause of foodborne illness. The outbreak started when several people in Germany were infected with enterohemorrhagic *E. coli* (EHEC) bacteria, leading to hemolytic-uremic syndrome (HUS), a medical emergency that requires urgent treatment. The outbreak did not only concern Germany, but also 11 other countries, including regions in North America.

4. Treatment

The mainstay of treatment is the assessment of dehydration and replacement of fluid and electrolytes. Administration of antibiotics has been shown to shorten the course of illness and duration of excretion of enterotoxigenic *E. coli* (ETEC) in adults in endemic areas and in traveler's diarrhoea, though the rate of resistance to commonly used antibiotics is increasing and they are generally not recommended. The antibiotic used depends upon susceptibility patterns in the particular geographical region. Currently, the antibiotics of choice are fluoroquinolones or azithromycin, with an emerging role for rifaximin. Oral rifaximin, a semisynthetic rifamycin derivative, is an effective and well-tolerated antibacterial for the management of adults with non-invasive traveller's diarrhoea. Rifaximin was significantly more effective than placebo and no less effective than ciprofloxacin in reducing the duration of diarrhea. While rifaximin is effective in patients with *E. coli*-predominant traveler's diarrhea, it appears ineffective in patients infected with inflammatory or invasive enteropathogens.

5. Prevention

ETEC is the type of *E. coli* that most vaccine development efforts are focused on. Antibodies against the LT and major CFs of ETEC provide protection against LT-producing ETEC expressing homologous CFs. Oral inactivated vaccines consisting of toxin antigen and whole cells, i.e., the licensed recombinant cholera B subunit (rCTB)-WC cholera vaccine Dukoral have been developed. There are currently no licensed vaccines for ETEC, though several are in various stages of development. In different trials, the rCTB-WC cholera vaccine provided high (85-100%) short-term protection. An oral ETEC vaccine candidate consisting of rCTB and formalin inactivated *E. coli* bacteria expressing major CFs has been shown in clinical trials to be safe, immunogenic, and effective against severe diarrhea in American travelers but not against ETEC diarrhoea in young children in Egypt. A modified ETEC vaccine consisting of recombinant *E. coli* strains over expressing the major CFs and a more LT-like hybrid toxoid called LCTBA, are undergoing clinical testing.

Other proven prevention methods for *E. coli* transmission include handwashing and improved sanitation and drinking water, as transmission occurs through fecal contamination of food and water supplies.

Causes and risk factors include working around livestock, consuming unpasteurized dairy product, eating undercooked meat, and drinking impure water.

F. Pseudomonas Aeruginosa

*Pseudomonas aeruginosa* is a common Gram-negative, rod-shaped bacterium that can cause disease in plants and animals, including humans. A species of considerable medical importance, *P. aeruginosa* is a multidrug resistant pathogen recognized for its ubiquity, its intrinsically advanced antibiotic resistance mechanisms, and its association with serious illnesses—especially hospital-acquired infections such as ventilator-associated pneumonia and various sepsis syndromes.

The organism is considered opportunistic insofar as serious infection often occurs during existing diseases or conditions—most notably cystic fibrosis and traumatic burns. It is also found generally in the immunocompromised but can infect the immunocompetent as in hot tub folliculitis. Treatment of *P. aeruginosa* infections can be difficult due to its natural resistance to antibiotics. When more advanced antibiotic drug regimens are needed adverse effects may result.

It is citrate, catalase, and oxidase positive. It is found in soil, water, skin flora, and most man-made environments throughout the world. It thrives not only in normal atmospheres, but also in low-oxygen atmospheres, thus has colonized many natural and artificial environments. It uses a wide range of organic material for food; in animals, its versatility enables the organism to infect damaged tissues or those with reduced immunity. The symptoms of such infections are generalized inflammation and sepsis. If such colonizations occur in critical body organs, such as the lungs, the urinary tract, and kidneys, the results can be fatal. Because it thrives on moist surfaces, this bacterium is also found on and in medical equipment, including catheters, causing cross-infections in hospitals and clinics. It is implicated in hot-tub rash. It is also able to decompose hydrocarbons and has been used to break down tarballs and oil from oil spills. *P. aeruginosa* is not extremely virulent in comparison with other major pathogenic bacterial species—for example *Staphylococcus aureus* and *Streptococcus pyogenes*—though *P. aeruginosa* is capable of extensive colonization, and can aggregate into enduring biofilms. *P. aeruginosa* does not fare especially well under suboptimal atmospheric conditions.

*P. aeruginosa* is commonly found in the exoskeletons and droppings of the domestic cockroaches—including the American cockroach and the German cockroach—which are found to be pervasive in households, as well as in hospital settings. The importance of the American cockroach (and other pests) as potential reservoirs or vectors of *P. aeruginosa* continues to be studied.

1. Pathogenesis

An opportunistic, nosocomial pathogen of immunocompromised individuals, *P. aeruginosa* typically infects the airway, burns, and wounds, and also causes other blood infections. Specific forms of infection include pneumonia, septic shock, skin and soft tissue infection, gastrointestinal tract infections and urinary tract infections. It is the most common cause of infections of burn injuries and of the outer ear (otitis externa), and is the most frequent colonizer of medical devices (e.g., catheters). *Pseudomonas* can be spread by equipment that gets contaminated and is not properly cleaned or on the hands of healthcare workers. *Pseudomonas* can, in rare circumstances, cause community-acquired pneumonias, as well as ventilator-associated pneumonias, being one of the most common agents isolated in several studies. Pyocyanin is a virulence factor of the bacteria and has been known to cause death in *C. elegans* by oxidative stress. However, salicylic acid can inhibit pyocyanin production. One in ten hospital-acquired infections is from *Pseudomonas*. Cystic fibrosis patients are also predisposed to *P. aeruginosa* infection of the lungs. *P. aeruginosa* may also be a common cause of "hot-tub rash" (dermatitis), caused by lack of proper, periodic attention to water quality. Since these bacteria like moist environments, such as hot tubs and swimming pools, they can cause skin rash or swimmer's ear. *Pseudomonas* is also a common cause of postoperative infection in radial keratotomy surgery patients. The organism is also associated with the skin lesion ecthyma gangrenosum. *P. aeruginosa* is frequently associated with osteomyelitis involving puncture wounds of the foot, believed to result from direct inoculation with *P. aeruginosa* via the foam padding found in tennis shoes, with diabetic patients at a higher risk.

2. Toxins

*P. aeruginosa* uses the virulence factor exotoxin A to inactivate eukaryotic elongation factor 2 via ADP-ribosylation in the host cell, much as the diphtheria toxin does. Without elongation factor 2, eukaryotic cells cannot synthesize proteins and necrotise. The release of intracellular contents induces an immunologic response in immunocompetent patients. In addition *P. aeruginosa* uses an exoenzyme, ExoU, which degrades the plasma membrane of eukaryotic cells, leading to lysis. Increasingly, it is becoming recognized that the iron-acquiring siderophore, pyoverdine, also functions as a toxin by removing iron from mitochondria, inflicting damage on this organelle.

3. Biofilms and Treatment Resistance

Biofilms of *P. aeruginosa* can cause chronic opportunistic infections, which are a serious problem for medical care in industrialized societies, especially for immunocompromised patients and the elderly. They often cannot be treated effectively with traditional antibiotic therapy. Biofilms seem to protect these bacteria from adverse environmental factors. *P. aeruginosa* can cause nosocomial infections and is considered a model organism for the study of antibiotic-resistant bacteria. Researchers consider it important to learn more about the molecular mechanisms that cause the switch from planktonic growth to a biofilm phenotype and about the role of QS in treatment-resistant bacteria such as *P. aeruginosa*. This should contribute to better clinical management of chronically infected patients, and should lead to the development of new drugs. Many genes and factors affect biofilm formation in *P. aeruginosa*. One of the main gene operons responsible for the initiation and maintaining the biofilm is the PSL operon. This 15-gene operon is responsible for the cell-cell and cell-surface interactions required for cell communication. It is also responsible for the sequestering of the extracellular polymeric substance matrix. This matrix is composed of nucleic acids, amino acids, carbohydrates, and various ions. This matrix is one of the main resistance mechanisms in the biofilms of P. aeruginosa.

Cyclic di-GMP is a major contributor to biofilm adherent properties. This signaling molecule in high quantities makes superadherent biofilms. When suppressed, the biofilms are less adherent and easier to treat. Polysaccharide synthesis locus (PSL) and cdi-GMP form a negative feedback loop. PSL stimulates cdi-GMP production, while high cd-GMP turns on the operon and increases activity of the operon.

Recent studies have shown that the dispersed cells from P. aeruginosa biofilms have lower c-di-GMP levels and different physiologies from those of planktonic and biofilm cells. Such dispersed cells are found to be highly virulent against macrophages and C. elegans, but highly sensitive towards iron stress, as compared with planktonic cells.

Recently, scientists have been examining the possible genetic basis for P. aeruginosa resistance to antibiotics such as tobramycin. One locus identified as being an important genetic determinant of the resistance in this species is ndvB, which encodes periplasmic glucans that may interact with antibiotics and cause them to become sequestered into the periplasm. These results suggest a genetic basis exists behind bacterial antibiotic resistance, rather than the biofilm simply acting as a diffusion barrier to the antibiotic.

4. Traditional Diagnosis

Depending on the nature of infection, an appropriate specimen is collected and sent to a bacteriology laboratory for identification. As with most bacteriological specimens, a Gram stain is performed, which may show Gram-negative rods and/or white blood cells. P. aeruginosa produces colonies with a characteristic "grape-like" or "fresh-tortilla" odor on bacteriological media. In mixed cultures, it can be isolated as clear colonies on MacConkey agar (as it does not ferment lactose) which will test positive for oxidase. Confirmatory tests include production of the blue-green pigment pyocyanin on cetrimide agar and growth at 42° C. A TSI slant is often used to distinguish nonfermenting Pseudomonas species from enteric pathogens in fecal specimens.

When P. aeruginosa is isolated from a normally sterile site (blood, bone, deep collections), it is generally considered dangerous, and almost always requires treatment. However, P. aeruginosa is frequently isolated from nonsterile sites (mouth swabs, sputum, etc.), and, under these circumstances, it may represent colonization and not infection. The isolation of P. aeruginosa from nonsterile specimens should, therefore, be interpreted cautiously, and the advice of a microbiologist or infectious diseases physician/pharmacist should be sought prior to starting treatment. Often, no treatment is needed.

5. Identification

P. aeruginosa is a Gram-negative, aerobic (and at times facultatively anaerobic), bacillus with unipolar motility. It has been identified as an opportunistic pathogen of both humans and plants. P. aeruginosa is the type species of the genus Pseudomonas. In certain conditions, P. aeruginosa can secrete a variety of pigments, including pyocyanin (blue-green), pyoverdine (yellow-green and fluorescent), and pyorubin (red-brown). These can be used to identify the organism.

P. aeruginosa is often preliminarily identified by its pearlescent appearance and grape-like or tortilla-like odor in vitro. Definitive clinical identification of P. aeruginosa often includes identifying the production of both pyocyanin and fluorescein, as well as its ability to grow at 42° C. P. aeruginosa is capable of growth in diesel and jet fuels, where it is known as a hydrocarbon-using microorganism, causing microbial corrosion. It creates dark, gellish mats sometimes improperly called "algae" because of their appearance.

6. Treatment

Many P. aeruginosa isolates are resistant to a large range of antibiotics and may demonstrate additional resistance after unsuccessful treatment. It should usually be possible to guide treatment according to laboratory sensitivities, rather than choosing an antibiotic empirically. If antibiotics are started empirically, then every effort should be made to obtain cultures (before administering first dose of antibiotic), and the choice of antibiotic used should be reviewed when the culture results are available.

Due to widespread resistance to many common first-line antibiotics, carbapenems, polymyxins, and more recently tigecycline were considered to be the drugs of choice; however, resistance to these drugs has also been reported. Despite this, they are still being used in areas where resistance has not yet been reported. Use of β-lactamase inhibitors such as sulbactam has been advised in combination with antibiotics to enhance antimicrobial action even in the presence of a certain level of resistance. Combination therapy after rigorous antimicrobial susceptibility testing has been found to be the best course of action in the treatment of multidrug-resistant P. aeruginosa. Some next-generation antibiotics that are reported as being active against P. aeruginosa include doripenem, ceftobiprole, and ceftaroline. However, these require more clinical trials for standardization. Therefore, research for the discovery of new antibiotics and drugs against P. aeruginosa is very much needed. Antibiotics that may have activity against P. aeruginosa include aminoglycosides (gentamicin, amikacin, tobramycin, but not kanamycin), quinolones (ciprofloxacin, levofloxacin, but not moxifloxacin), cephalosporins (ceftazidime, cefepime, cefoperazone, cefpirome, ceftobiprole, but not cefuroxime, cefotaxime, or ceftriaxone), antipseudomonal penicillins: carboxypenicillins (carbenicillin and ticarcillin), and ureidopenicillins (mezlocillin, azlocillin, and piperacillin). P. aeruginosa is intrinsically resistant to all other penicillins, carbapenems (meropenem, imipenem, doripenem, but not ertapenem), polymyxins (polymyxin B and colistin) and monobactams (aztreonam).

As fluoroquinolone is one of the few antibiotics widely effective against P. aeruginosa, in some hospitals, its use is severely restricted to avoid the development of resistant strains. On the rare occasions where infection is superficial and limited (for example, ear infections or nail infections), topical gentamicin or colistin may be used.

7. Antibiotic Resistance

One of the most worrisome characteristics of P. aeruginosa is its low antibiotic susceptibility, which is attributable to a concerted action of multidrug efflux pumps with chromosomally encoded antibiotic resistance genes (e.g., mexAB, mexXY, etc.) and the low permeability of the bacterial cellular envelopes. In addition to this intrinsic resistance, P. aeruginosa easily develops acquired resistance either by mutation in chromosomally encoded genes or by the horizontal gene transfer of antibiotic resistance determinants. Development of multidrug resistance by P. aeruginosa isolates requires several different genetic events, including acquisition of different mutations and/or horizontal transfer of antibiotic resistance genes. Hypermutation favours the selection of mutation-driven antibiotic resistance in *P. aeruginosa* strains producing chronic infections, whereas the clustering of several different antibiotic resistance genes in integrons favors the concerted acquisition of antibiotic resistance determinants. Some recent studies have shown phenotypic resistance associated to biofilm formation or to the emergence of small-colony variants may be important in the response of *P. aeruginosa* populations to antibiotics treatment.

Mechanisms underlying antibiotic resistance have been found to include production of antibiotic-degrading or antibiotic-inactivating enzymes, outer membrane proteins to evict the antibiotics and mutations to change antibiotic targets. Presence of antibiotic-degrading enzymes such as extended-spectrum β-lactamases like PER-1, PER-2, VEB-1, AmpC cephalosporinases, carbapenemases like serine oxacillinases, metallo-b-lactamases, OXA-type carbapenemases, aminoglycoside-modifying enzymes, among others have been reported. *P. aeruginosa* can also modify the targets of antibiotic action, for example methylation of 16S rRNA to prevent aminoglycoside binding and modification of DNA, or topoisomerase to protect it from the action of quinolones. *P. aeruginosa* has also been reported to possess multidrug efflux pumps like AdeABC and AdeDE efflux systems that confer resistance against number of antibiotic classes. An important factor found to be associated with antibiotic resistance is the decrease in the virulence capabilities of the resistant strain. Such findings have been reported in the case of rifampicin-resistant and colistin-resistant strains, in which decrease in infective ability, quorum sensing and motility have been documented.

Mutations in DNA gyrase are commonly associated with antibiotic resistance in *P. aeruginosa*. These mutations, when combined with others, confer high resistance without hindering survival. Additionally, genes involved in cyclic-di-GMP signaling may contribute to resistance. When grown in vitro conditions designed to mimic a cystic fibrosis patient's lungs, these genes mutate repeatedly.

8. Prevention

Probiotic prophylaxis may prevent colonization and delay onset of *Pseudomonas* infection in an ICU setting. Immunoprophylaxis against *Pseudomonas* is being investigated. The risk of contracting *P. aeruginosa* can be reduced by avoiding pools, hot tubs, and other bodies of standing water; regularly disinfecting and/or replacing equipment that regularly encounters moisture (such as contact lens equipment and solutions); and washing one's hands often (which is protective against many other pathogens as well). However, even the best hygiene practices cannot totally protect an individual against *P. aeruginosa*, given how common *P. aeruginosa* is in the environment.

G. Other Bacteria

1. *Acinetobacter Baumannii*

*Acinetobacter baumannii* is a Gram-negative bacterial pathogen that has rapidly emerged as a leading cause of infection world-wide. In fact, *A. baumannii* is now responsible for up to 20% of all intensive care unit infections in some regions of the world. This organism causes a range of diseases, with pneumonia being the most prevalent. As a result of its resistance to drug treatment, some estimates state the disease is killing tens of thousands of U.S. hospital patients each year.

*A. baumannii* forms opportunistic infections. There have been many reports of *A. baumannii* infections among American soldiers wounded in Iraq, earning it the nickname "Iraqibacter." Multi-drug resistant *A. baumannii* is abbreviated as MDRAB. MDRAB is not a new phenomenon; it has always been inherently resistant to multiple antibiotics.

*A. baumannii* is the most relevant human pathogen within the *Acinetobacter* genus. Most *A. baumannii* isolates are multiresistant, containing in their genome small, isolated islands of alien (meaning transmitted genetically from other organisms) DNA and other cytological and genetic material; this has led to more virulence. *Acinetobacter* have no flagellum; the name is Greek for "motionless."

*Acinetobacter* enters into the body through open wounds, catheters, and breathing tubes. It usually infects those with compromised immune systems, such as the wounded, the elderly, children or those with immune diseases. Colonization poses no threat to people who aren't already ill, but colonized health care workers and hospital visitors can carry the bacteria into neighboring wards and other medical facilities. The number of nosocomial infections (hospital-acquired infections) caused by *A. baumannii* has increased in recent years; as have most other nosocomial pathogens (MRSA, VRSA, VRE, etc.).

The first military outbreaks of severe *A. baumannii* infections occurred in April, 2003 in American soldiers returning from Iraq. Early reports attributed the infections to the Iraqi soil. Later testing demonstrated widespread contamination of field hospitals, via transportation of personnel and equipment from previously contaminated European hospitals, as the most plausible vector.

Nosocomial *A. baumannii* bacteremia may cause severe clinical disease that is associated with an elevated mortality rate. This opportunistic pathogen expresses a myriad of factors that could play a role in human pathogenesis. Among these factors are the attachment to and persistence on solid surfaces, the acquisition of essential nutrients such as iron, the adhesion to epithelial cells and their subsequent killing by apoptosis, and the production and/or secretion of enzymes and toxic products that damage host tissues. However, very little is known about the molecular nature of most of these processes and factors and almost nothing has been shown with regard to their role in bacterial virulence and the pathogenesis of serious infectious diseases. Fortunately, some of these gaps can now be filled by testing appropriate isogenic derivatives in relevant animal models that mimic the infections in humans, particularly the outcome of deadly pneumonia. Such an approach should provide new and relevant information on the virulence traits of this normally underestimated bacterial human pathogen.

Multidrug-resistant *A. baumannii* is a common problem in many hospitals in the U.S. and Europe. First line treatment is with a carbapenem antibiotic such as imipenem, but carbapenem resistance is increasingly common. Other treatment options include polymyxins, tigecycline and aminoglycosides. The institution of strict infection-control measures, such as monitored hand washing, can lower hospital infection rates. MDRAB infections are difficult and costly to treat. A study at a public teaching hospital found that the mean total hospital cost of patients who acquired MDRAB was $98,575 higher than that of control patients who had identical burn severity of illness indices.

2. *Acinetobacter* Spp.

*Acinetobacter* spp. other than *A. baumannii* include *A. calcoaceticus*, *A. lwoffii*, *A. junii*, *A. anitratus*, *A. baumannii-calcoaciticus* complex. *Acinetobacter* is a Gram-negative genus of bacteria belonging to the Gammaproteobacteria. Non-motile, *Acinetobacter* species are oxidase-negative, and occur in pairs under magnification. They are important soil organisms where they contribute to the mineralization of, for example, aromatic compounds. *Acinetobacter* are a key source of infection in debilitated patients in the hospital. Different species of bacteria in this genus can be identified using Fluorescence-Lactose-Denitrification medium (FLN) to find the amount of acid produced by metabolism of glucose.

Species of the genus *Acinetobacter* are strictly aerobic, nonfermentative, Gram-negative bacilli. They show preponderantly a coccobacillary morphology on nonselective agar. Rods predominate in fluid media, especially during early growth. The morphology of *Acinetobacter* spp. can be quite variable in Gram stained human clinical specimens, and cannot be used to differentiate *Acinetobacter* from other common causes of infection.

Most strains of *Acinetobacter*, except some of the *A. lwoffii* strains, grow well on MacConkey agar (without salt). Although officially classified as non-lactose fermenting, they are often partially lactose fermenting when grown on MacConkey agar. They are oxidase negative, nonmotile and usually nitrate negative.

*Acinetobacter* species are generally considered nonpathogenic to healthy individuals. However, several species persist in hospital environments and cause severe, life-threatening infections in compromised patients. The spectrum of antibiotic resistances of these organisms together with their survival capabilities make them a threat to hospitals as documented by recurring outbreaks both in highly developed countries and elsewhere. An important factor for their pathogenic potential is probably an efficient means of horizontal gene transfer even though such a mechanism has so far only been observed and analyzed in *A. baylyi*, a species that lives in the soil and has never been associated with infections. *Acinetobacter* is frequently isolated in nosocomial infections and is especially prevalent in intensive care units, where both sporadic cases as well as epidemic and endemic occurrence is common. *A. lwoffi* is responsible for most cases of *Acinetobacter* meningitis.

*Acinetobacter* species are innately resistant to many classes of antibiotics, including penicillin, chloramphenicol, and often aminoglycosides. Resistance to fluoroquinolones has been reported during therapy and this has also resulted in increased resistance to other drug classes mediated through active drug efflux. A dramatic increase in antibiotic resistance in *Acinetobacter* strains has been reported by the CDC and the carbapenems are recognized as the gold-standard and treatment of last resort. *Acinetobacter* species are unusual in that they are sensitive to sulbactam; sulbactam is most commonly used to inhibit bacterial beta-lactamase, but this is an example of the antibacterial property of sulbactam itself.

3. *Burkholderia* Spp.

*Burkholderia* spp. (*B. cepacia, B. cenocepacia, B. cepacia* complex) are members of a genus of proteobacteria probably best-known for its pathogenic members *B. mallei* (responsible for glanders, a disease that occurs mostly in horses and related animals), *B. pseudomallei* (causative agent of melioidosis), and *B. cepacia* (an important pathogen of pulmonary infections in people with cystic fibrosis).

The *Burkholderia* (previously part of *Pseudomonas*) genus name refers to a group of virtually ubiquitous gram-negative, motile, obligately aerobic rod-shaped bacteria including both animal/human and plant pathogens as well as some environmentally-important species. In particular, *B. xenovorans* (previously named *Pseudomonas cepacia* then *B. cepacia* and *B. fungorum*) is renowned for its ability to degrade chlororganic pesticides and polychlorinated biphenyls (PCBs). Due to their antibiotic resistance and the high mortality rate from their associated diseases, *B. mallei* and *B. pseudomallei* are considered to be potential biological warfare agents, targeting livestock and humans.

4. *Klebsiella Pneumoniae*

*Klebsiella pneumoniae* is a Gram-negative, non-motile, encapsulated, lactose fermenting, facultative anaerobic, rod shaped bacterium found in the normal flora of the mouth, skin, and intestines. It is clinically the most important member of the *Klebsiella* genus of Enterobacteriaceae; it is closely related to *K. oxytoca* from which it is distinguished by being indole-negative and by its ability to grow on both melezitose and 3-hydroxybutyrate. It naturally occurs in the soil and about 30% of strains can fix nitrogen in anaerobic conditions. As a free-living diazotroph, its nitrogen fixation system has been much studied.

Members of the *Klebsiella* genus typically express 2 types of antigens on their cell surface. The first, O antigen, is a lipopolysaccharide of which 9 varieties exist. The second is K antigen, a capsular polysaccharide with more than 80 varieties. Both contribute to pathogenicity and form the basis for subtyping.

Research has implicated molecular mimicry between HLA-B27 and two molecules in *Klebsiella* microbes as the cause of ankylosing spondylitis. As a general rule, *Klebsiella* infections tend to occur in people with a weakened immune system from improper diet (alcoholics and diabetics). Many of these infections are obtained when a person is in the hospital for some other reason (a nosocomial infection). The most common infection caused by *Klebsiella* bacteria outside the hospital is pneumonia.

New antibiotic resistant strains of *K. pneumoniae* are appearing, and it is increasingly found as a nosocomial infection. *Klebsiella* ranks second to *E. coli* for urinary tract infections in older persons. It is also an opportunistic pathogen for patients with chronic pulmonary disease, enteric pathogenicity, nasal mucosa atrophy, and rhinoscleroma. Feces are the most significant source of patient infection, followed by contact with contaminated instruments.

Multiply-resistant *K. pneumoniae* have been killed in vivo via intraperitoneal, intravenous or intranasal administration of phages in laboratory tests.

5. *Stenotrophomonas Maltophilia*

*Stenotrophomonas maltophilia* is an aerobic, nonfermentative, Gram-negative bacterium. It is an uncommon bacteria and it is difficult to treat infections in humans. Initially classified as *Pseudomonas maltophilia*, *S. maltophilia* was also grouped in the genus *Xanthomonas* before eventually becoming the type species of the genus *Stenotrophomonas* in 1993.

*S. maltophilia* are slightly smaller (0.7-1.8×0.4-0.7 micrometers) than other members of the genus. They are motile due to polar flagella and grow well on MacConkey agar producing pigmented colonies. *S. maltophilia* are catalase-positive, oxidase-negative (which distinguishes them from most other members of the genus) and have a positive reaction for extracellular DNase.

*S. maltophilia* is ubiquitous in aqueous environments, soil and plants, including water, urine, or respiratory secretions; it has also been used in biotechnology applications. In immunocompromised patients, *S. maltophilia* can lead to nosocomial infections.

*S. maltophilia* frequently colonizes breathing tubes such as endotracheal or tracheostomy tubes, the respiratory tract and indwelling urinary catheters. Infection is usually facilitated by the presence of prosthetic material (plastic or metal), and the most effective treatment is removal of the prosthetic material (usually a central venous catheter or similar device). The growth of *S. maltophilia* in microbiological cultures of respiratory or urinary specimens is therefore sometimes difficult to interpret and not a proof of infection. If, however, it is grown from sites which would be normally sterile (e.g., blood), then it usually represents true infection.

In immunocompetent individuals, S. maltophilia is a relatively unusual cause of pneumonia, urinary tract infection, or blood stream infection; in immunocompromised patients, however, S. maltophilia is a growing source of latent pulmonary infections. S. maltophilia colonization rates in individuals with cystic fibrosis have been increasing.

S. maltophilia is naturally resistant to many broad-spectrum antibiotics (including all carbapenems) and is thus often difficult to eradicate. Many strains of S. maltophilia are sensitive to co-trimoxazole and ticarcillin, though resistance has been increasing. It is not usually sensitive to piperacillin, and sensitivity to ceftazidime is variable.

6. Haemophilus Influenzae

Haemophilus influenzae, formerly called Pfeiffer's bacillus or Bacillus influenzae, is a non-motile Gram-negative rod-shaped bacterium first described in 1892 during an influenza pandemic. A member of the Pasteurellaceae family, it is generally aerobic, but can grow as a facultative anaerobe. H. influenzae was mistakenly considered to be the cause of influenza until 1933, when the viral etiology of the flu became apparent. Still, H. influenzae is responsible for a wide range of clinical diseases.

In 1930, 2 major categories of H. influenzae were defined: the unencapsulated strains and the encapsulated strains. Encapsulated strains were classified on the basis of their distinct capsular antigens. There are six generally recognized types of encapsulated H. influenzae: a, b, c, d, e, and f. Genetic diversity among unencapsulated strains is greater than within the encapsulated group. Unencapsulated strains are termed nontypable (NTHi) because they lack capsular serotypes, however they can be classified by multi-locus sequence typing. The pathogenesis of H. influenzae infections is not completely understood, although the presence of the capsule in encapsulated type b (Hib), a serotype causing conditions such as epiglottitis, is known to be a major factor in virulence. Their capsule allows them to resist phagocytosis and complement-mediated lysis in the non-immune host. The unencapsulated strains are almost always less invasive, however they can produce an inflammatory response in humans which can lead to many symptoms. Vaccination with Hib conjugate vaccine is effective in preventing Hib infection. Several vaccines are now available for routine use against Hib, however vaccines are not yet available against NTHi.

Most strains of H. influenzae are opportunistic pathogens—that is, they usually live in their host without causing disease, but cause problems only when other factors (such as a viral infection or reduced immune function) create an opportunity.

Naturally-acquired disease caused by H. influenzae seems to occur in humans only. In infants and young children, H. influenzae type b (Hib) causes bacteremia, pneumonia, and acute bacterial meningitis. Occasionally, it causes cellulitis, osteomyelitis, epiglottitis, and infectious arthritis. Due to routine use of the Hib conjugate vaccine in the U.S. since 1990, the incidence of invasive Hib disease has decreased to 1.3/100,000 in children. However, Hib remains a major cause of lower respiratory tract infections in infants and children in developing countries where vaccine is not widely used. Unencapsulated H. influenzae causes ear infections (otitis media), eye infections (conjunctivitis), and sinusitis in children and is associated with pneumonia.

Clinical diagnosis of H. influenzae is typically performed by bacterial culture or latex particle agglutination. Diagnosis is considered confirmed when the organism is isolated from a sterile body site. In this respect, H. influenzae cultured from the nasopharyngeal cavity or sputum would not indicate H. influenzae disease because these sites are colonized in disease free individuals. However, H. influenzae isolated from cerebrospinal fluid or blood would indicate a H. influenzae infection.

Bacterial culture of H. influenzae is performed on agar plates, preferably Chocolate agar, plate with added X(Hemin) & V(NAD) factors at 37° C. in an enriched $CO_2$ incubator. Blood agar growth is only achieved as a satellite phenomenon around other bacteria. Colonies of H. influenzae appear as convex, smooth, pale, grey or transparent colonies. Gram-stained and microscopic observation of a specimen of H. influenzae will show Gram-negative, coccobacilli, with no specific arrangement. The cultured organism can be further characterized using catalase and oxidase tests, both of which should be positive. Further serological is necessary to distinguish the capsular polysaccharide and differentiate between H. influenzae b and non-encapsulated species.

Although highly specific, bacterial culture of H. influenzae lacks in sensitivity. Use of antibiotics prior to sample collection greatly reduces the isolation rate by killing the bacteria before identification is possible. Beyond this, H. influenzae is a finicky bacterium to culture, and any modification of culture procedures can greatly reduce isolation rates. Poor quality of laboratories in developing countries has resulted in poor isolation rates of H. influenzae.

H. influenzae will grow in the hemolytic zone of Staphylococcus aureus on Blood Agar plates. The hemolysis of cells by S. aureus releases nutrients vital to the growth of H. influenzae. H. influenzae will not grow outside the hemolytic zone of S. aureus due to the lack of nutrients in these areas.

H. influenzae produces beta lactamases, and it is also able to modify its penicillin binding protein, so it has gained resistance to the penicillin family of antibiotics. In severe cases cefotaxime and ceftriaxone are the elected antibiotics, delivered directly into the bloodstream, and for the less severe cases an association of ampicillin and sulbactam, cephalosporins of the second and third generation, or fluoroquinolones.

7. Streptococcus Pneumoniae

Streptococcus pneumoniae is a gram-positive, alpha-hemolytic, bile soluble aerotolerant anaerobe and a member of the genus Streptococcus. A significant human pathogenic bacterium, S. pneumoniae was recognized as a major cause of pneumonia in the late 19th century and is the subject of many humoral immunity studies.

Despite the name, the organism causes many types of pneumococcal infection other than pneumonia, including acute sinusitis, otitis media, meningitis, bacteremia, sepsis, osteomyelitis, septic arthritis, endocarditis, peritonitis, pericarditis, cellulitis, and brain abscess. S. pneumoniae is the most common cause of bacterial meningitis in adults and children, and is one of the top two isolates found in ear infection, otitis media. Pneumococcal pneumonia is more common in the very young and the very old.

S. pneumoniae can be differentiated from S. viridans, some of which are also alpha hemolytic, using an optochin test, as S. pneumoniae is optochin sensitive. S. pneumoniae can also be distinguished based on its sensitivity to lysis by bile. The encapsulated, gram-positive coccoid bacteria have a distinctive morphology on gram stain, the so-called, "lancet shape." It has a polysaccharide capsule that acts as a virulence factor for the organism; more than 90 different serotypes are known, and these types differ in virulence, prevalence, and extent of drug resistance.

*S. pneumoniae* is part of the normal upper respiratory tract flora but as with many natural flora, it can become pathogenic under the right conditions (e.g., if the immune system of the host is suppressed). Invasins such as Pneumolysin, an anti-phagocytic capsule, various adhesins and immunogenic cell wall components are all major virulence factors.

Both *H. influenzae* and *S. pneumoniae* can be found in the human upper respiratory system. A study of competition in a laboratory revealed that, in a petri dish, *S. pneumoniae* always overpowered *H. influenzae* by attacking it with hydrogen peroxide. When both bacteria are placed together into a nasal cavity, within 2 weeks, only *S. pneumoniae* survives. When both are placed separately into a nasal cavity, each one survives. Upon examining the upper respiratory tissue from mice exposed to both bacteria, an extraordinarily large number of neutrophil immune cells were found. In mice exposed to only one bacteria, the cells were not present. Lab tests show that neutrophils that were exposed to already dead *H. influenzae* were more aggressive in attacking *S. pneumoniae* than unexposed neutrophils. Exposure to killed *H. influenzae* had no effect on live *H. influenzae*.

8. Vibrio Cholerae

*Vibrio cholera*, also known as *Kommabacillus*, is a gram negative comma-shaped bacterium with a polar flagellum that causes cholera in humans. There are two major biotypes of *Vibrio cholerae* identified by hemaggluttination testing, classical and El Tor, and numerous serogroups. The classical biotype is found only in Bangladesh, whereas the El Tor is found throughout the world.

*Vibrio cholerae* pathogenicity genes code for proteins directly or indirectly involved in the virulence of the bacteria. Because of their same transcriptional regulation and their implication in the same pathway, pathogenicity genes are generally organized in operons and/or gene clusters. In *Vibrio cholerae*, most of virulence genes are located in two pathogenicity plasmids, which are organized as prophages: CTX (Cholera ToXins) plasmid and TCP (Toxin-Coregulated Pilus) plasmid, also named as *Vibrio cholerae* Pathogenicity Island (VPI). Virulent and epidemic strains of *Vibrio cholerae* require these two genetic elements to cause infections.

9. Vibrio Parahaemolyticus

*Vibrio parahaemolyticus* is a curved, rod-shaped, Gram-negative bacterium found in brackish saltwater that causes gastrointestinal illness in humans, when ingested. *V. parahaemolyticus* is oxidase positive, facultatively aerobic, and does not form spores. Like other members of the genus *Vibrio*, this species is motile, with a single, polar flagellum.

While infection of *V. parahaemolyticus* can occur via the fecal-oral route, the predominant cause of the acute gastroenteritis caused by *V. parahaemolyticus* is through ingestion of bacteria in raw or undercooked seafood, usually oysters. Wound infections also occur, but are less common than seafood-borne disease. The disease mechanism of *V. parahaemolyticus* infections has not been fully elucidated.

Outbreaks tend to be concentrated along coastal regions during the summer and early fall when higher water temperatures favor higher levels of bacteria. Seafood most often implicated includes squid, mackerel, tuna, sardines, crab, shrimp, and bivalves like oysters and clams. The incubation period of ~24 hours is followed by explosive, watery diarrhea accompanied by nausea, vomiting, abdominal cramps, and sometimes fever. *V. parahaemolyticus* symptoms typically resolve with-in 72 hours, but can persist for up to 10 days in immunocompromised individuals. As the vast majority of cases of *V. parahaemolyticus* food infection are self-limiting, treatment is not typically necessary. In severe cases, fluid and electrolyte replacement is indicated.

Additionally, swimming or working in affected areas can lead to infections of the eyes or ears and open cuts and wounds. Following Hurricane Katrina, there were three wound infections caused by *V. parahaemolyticus* and two of these led to death.

10. Yersinia Pseudotuberculosis

*Yersinia pseudotuberculosis* is a Gram-negative bacterium which primarily causes *Pseudotuberculosis* (*Yersinia*) disease in animals; humans occasionally get infected zoonotically, most often through the food-borne route.

In animals, *Y. pseudotuberculosis* can cause tuberculosis-like symptoms, including localized tissue necrosis and granulomas in the spleen, liver, and lymph node.

In humans, symptoms of *Pseudotuberculosis* (*Yersinia*) include fever and right-sided abdominal pain, but the diarrheal component is often absent, which sometimes makes the resulting condition difficult to diagnose. *Y. pseudotuberculosis* infections can mimic appendicitis, especially in children and younger adults, and, in rare cases the disease may cause skin complaints (erythema nodosum), joint stiffness and pain (reactive arthritis), or spread of bacteria to the blood (bacteremia).

*Pseudotuberculosis* (*Yersinia*) usually becomes apparent 5-10 days after exposure and typically lasts 1-3 weeks without treatment. In complex cases or those involving immunocompromised patients, antibiotics may be necessary for treatment; ampicillin, aminoglycosides, tetracycline, chloramphenicol, or a cephalosporin may all be effective.

The recently described syndrome Izumi-fever has also been linked to infection with *Y. pseudotuberculosis*.

This bacterium possesses many virulence factors to facilitate attachment, invasion, and colonization of its host. Superantigens, bacterial adhesions, and the actions of Yops (which are bacterial proteins once thought to be "*Yersinia* outer membrane proteins") that are encoded on the "[plasmid] for *Yersinia* virulence"—commonly known as the pYV—cause host pathogenesis and allow the bacteria to live parasitically.

*Y. pseudotuberculosis* adheres strongly to intestinal cells via chromosomally encoded proteins so that Yop secretion may occur, to avoid being removed by peristalsis, and to invade target host cells.

Certain strains of *Y. pseudotuberculosis* express a superantigenic exotoxin, YPM, or the *Y. pseudotuberculosis*-derived mitogen, from the chromosomal ypm gene. Strains which carry the exotoxin gene are rare in Western countries where the disease, when at all apparent, manifests itself largely with minor symptoms, whereas more than 95% of strains from Far Eastern countries contain ypm and are correlated with Izumi fever and Kawasaki disease.

Although the superantigen poses the greatest threat to host health, all virulence factors contribute to *Y. pseudotuberculosis* viability in vivo and define the bacterium's pathogenic characteristics. *Y. pseudotuberculosis* can live extracellularly due to its formidable mechanisms of phagocytosis and opsonisation resistance; yet, by limited pYV action, it can populate host cells, especially macrophages, intracellularly to further evade immune responses and be disseminated throughout the body.

11. Salmonella

*Salmonella* is a genus of rod-shaped, Gram-negative, non-spore-forming, predominantly motile enterobacteria with flagella which grade in all directions (i.e. peritrichous).

They are chemoorganotrophs, obtaining their energy from oxidation and reduction reactions using organic sources, and are facultative anaerobes. Most species produce hydrogen sulfide, which can readily be detected by growing them on media containing ferrous sulfate, such as TSI. Most isolates exist in two phases: a motile phase I and a nonmotile phase II.

*Salmonella* is closely related to the *Escherichia* genus and are found worldwide in cold- and warm-blooded animals, including humans, and in the environment. They cause illnesses like typhoid fever, paratyphoid fever, and the foodborne illness. *Salmonella* infections are zoonotic and-can be transferred between humans and nonhuman animals. Many infections are due to ingestion of contaminated food. Typhoid/paratyphoid *Salmonella* is distinguished from enteritis *Salmonella* because of the possession of a special virulence factor and a capsule protein (virulence antigen), which can cause serious illness, such as *Salmonella enterica* subsp. *enterica* serovar *Typhi*. *Salmonella typhi*. is adapted to humans and does not occur in animals.

Enteritis salmonelliosis or Food Poisoning *Salmonella* is a group consisting of potentially all other serotypes (over a thousand) of the *Salmonella* bacterium, most of which have never been found in humans. These are encountered in various *Salmonella* species, most having never been linked to a specific host, and can also infect humans. The organism enters through the digestive tract and must be ingested in large numbers to cause disease in healthy adults. Gastric acidity is responsible for the destruction of the majority of ingested bacteria. The infection usually occurs as a result of massive ingestion of foods in which the bacteria are highly concentrated similarly to a culture medium. However, infants and young children are much more susceptible to infection, easily achieved by ingesting a small number of bacteria. It has been shown that, in infants, the contamination could be through inhalation of bacteria-laden dust.

After a short incubation period of a few hours to one day, the germ multiplies in the intestinal lumen causing an intestinal inflammation with diarrhea that is often mucopurulent and bloody. In infants, dehydration can cause a state of severe toxicosis. The symptoms are usually mild. There is normally no sepsis, but it can occur exceptionally as a complication in weakened elderly patients (Hodgkin's disease, for example). Extraintestinal localizations are possible, especially *Salmonella* meningitis in children, osteitis, etc. Enteritis *Salmonella*, e.g., *Salmonella enterica* subsp. *enterica* serovar *enteritidis*, can cause diarrhea, which usually does not require antibiotic treatment. However, in people at risk such as infants, small children, the elderly, *Salmonella* infections can become very serious, leading to complications. If these are not treated, HIV patients and those with suppressed immunity can become seriously ill. Children with sickle cell anaemia who are infected with *Salmonella* may develop osteomyelitis.

In Germany, *Salmonella* infections must be reported. Between 1990 and 2005, the number of officially recorded cases decreased from approximately 200,000 cases to approximately 50,000. It is estimated that every fifth person in Germany is a carrier of *Salmonella*. In the USA, there are approximately 40,000 cases of *Salmonella* infection reported each year. According to the World Health Organization, over 16 million people worldwide are infected with typhoid fever each year, with 500,000 to 600,000 fatal cases.

*Salmonella* can survive for weeks outside a living body. They have been found in dried excrement after more than 2.5 years. *Salmonella* are not destroyed by freezing. Ultraviolet radiation and heat accelerate their demise; they perish after being heated to 55° C. (131° F.) for one hour, or to 60° C. (140° F.) for half an hour. To protect against *Salmonella* infection, it is recommended that food be heated for at least ten minutes at 75° C. (167° F.) so that the center of the food reaches this temperature.

F. Antibiotics

The term "antibiotics" are drugs which may be used to treat a bacterial infection through either inhibiting the growth of bacteria or killing bacteria. Without being bound by theory, it is believed that antibiotics can be classified into two major classes: bactericidal agents that kill bacteria or bacteriostatic agents that slow down or prevent the growth of bacteria.

The first commercially available antibiotic was released in the 1930's. Since then, many different antibiotics have been developed and widely prescribed. In 2010, on average, 4 in 5 Americans are prescribed antibiotics annually. Given the prevalence of antibiotics, bacteria have started to develop resistance to specific antibiotics and antibiotic mechanisms. Without being bound by theory, the use of antibiotics in combination with another antibiotic may modulate resistance and enhance the efficacy of one or both agents.

In some embodiments, antibiotics can fall into a wide range of classes. In some embodiments, the compounds of the present disclosure may be used in conjunction with another antibiotic. In some embodiments, the compounds may be used in conjunction with a narrow spectrum antibiotic which targets a specific bacteria type. In some non-limiting examples of bactericidal antibiotics include penicillin, cephalosporin, polymyxin, rifamycin, lipiarmycin, quinolones, and sulfonamides. In some non-limiting examples of bacteriostatic antibiotics include macrolides, lincosamides, or tetracyclines. In some embodiments, the antibiotic is an aminoglycoside such as kanamycin and streptomycin, an ansamycin such as rifaximin and geldanamycin, a carbacephem such as loracarbef, a carbapenem such as ertapenem, imipenem, a cephalosporin such as cephalexin, cefixime, cefepime, and ceftobiprole, a glycopeptide such as vancomycin or teicoplanin, a lincosamide such as lincomycin and clindamycin, a lipopeptide such as daptomycin, a macrolide such as clarithromycin, spiramycin, azithromycin, and telithromycin, a monobactam such as aztreonam, a nitrofuran such as furazolidone and nitrofurantoin, an oxazolidonones such as linezolid, a penicillin such as amoxicillin, azlocillin, flucloxacillin, and penicillin G, an antibiotic polypeptide such as bacitracin, polymyxin B, and colistin, a quinolone such as ciprofloxacin, levofloxacin, and gatifloxacin, a sulfonamide such as silver sulfadiazine, mefenide, sulfadimethoxine, or sulfasalazine, or a tetracycline such as demeclocycline, doxycycline, minocycline, oxytetracycline, or tetracycline. In some embodiments, the compounds could be combined with a drug which acts against mycobacteria such as cycloserine, capreomycin, ethionamide, rifampicin, rifabutin, rifapentine, and streptomycin. Other antibiotics that are contemplated for combination therapies may include arsphenamine, chloramphenicol, fosfomycin, fusidic acid, metronidazole, mupirocin, platensimycin, quinupristin, dalfopristin, thiamphenicol, tigecycline, tinidazole, or trimethoprim.

IV. DETECTION MATERIALS AND TECHNIQUES

A. Probes and Primers

Detection of nucleic acids may involve the use of a hybridization reaction, such as between a target nucleic acid and an oligonucleotide probe or primer (e.g., a nucleic acid hybridization assay). In some embodiments, the oligonucleotide probe is immobilized on a substrate. Substrates include, but are not limited to, arrays, microarrays, wells of a multi-well plate, and beads (e.g. non-magnetic, magnetic, paramagnetic, hydrophobic, and hydrophilic beads). Examples of materials useful as substrates include but are not limited to nitrocellulose, glass, silicon, and a variety of gene arrays. A preferred hybridization assay is conducted on high-density gene chips as described in U.S. Pat. No. 5,445,934.

The terms "polynucleotide," "nucleotide," "nucleotide sequence," "nucleic acid," and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

A "nucleotide probe" or "probe" refers to a polynucleotide used for detecting or identifying its corresponding target polynucleotide in a hybridization reaction.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR, or the enzymatic cleavage of a polynucleotide by a ribozyme.

The term "hybridized" as applied to a polynucleotide refers to the ability of the polynucleotide to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. The hybridization reaction may constitute a step in a more extensive process, such as the initiation of a PCR reaction, or the enzymatic cleavage of a polynucleotide by a ribozyme.

Hybridized nucleic acids may be detected by detecting one or more labels attached to the sample nucleic acids. The labels can be incorporated by any of a number of means well known to those of skill in the art.

B. Molecular Beacons

Molecular beacons are oligonucleotide hybridization probes that can report the presence of specific nucleic acids in homogenous solutions. The term more often used is molecular beacon probes. Molecular beacons are hairpin shaped molecules with an internally quenched fluorophore whose fluorescence is restored when they bind to a target nucleic acid sequence. This is a novel non-radioactive method for detecting specific sequences of nucleic acids. They are useful in situations where it is either not possible or desirable to isolate the probe-target hybrids from an excess of the hybridization probes.

A typical molecular beacon probe is 25 nucleotides long. The middle 15 nucleotides are complementary to the target DNA or RNA and do not base pair with one another, while the five nucleotides at each terminus are complementary to each other rather than to the target DNA. A typical molecular beacon structure can be divided in 4 parts: 1) loop, an 18-30 base pair region of the molecular beacon that is complementary to the target sequence; 2) stem formed by the attachment to both termini of the loop of two short (5 to 7 nucleotide residues) oligonucleotides that are complementary to each other; 3) 5' fluorophore at the 5' end of the molecular beacon, a fluorescent dye is covalently attached; 4) 3' quencher (non-fluorescent) dye that is covalently attached to the 3' end of the molecular beacon. When the beacon is in closed loop shape, the quencher resides in proximity to the fluorophore, which results in quenching the fluorescent emission of the latter.

If the nucleic acid to be detected is complementary to the strand in the loop, the event of hybridization occurs. The duplex formed between the nucleic acid and the loop is more stable than that of the stem because the former duplex involves more base pairs. This causes the separation of the stem and hence of the fluorophore and the quencher. Once the fluorophore is distanced from the quencher, illumination of the hybrid with light results in the fluorescent emission. The presence of the emission reports that the event of hybridization has occurred and hence the target nucleic acid sequence is present in the test sample.

Molecular beacons are synthetic oligonucleotides whose preparation is well documented. In addition to the conventional set of nucleoside phosphoramidites, the synthesis also requires a solid support derivatized with a quencher and a phosphoramidite building block designed for the attachment of a protected fluorescent dye.

C. FRET

Förster resonance energy transfer (FRET), fluorescence resonance energy transfer (FRET), resonance energy transfer (RET) or electronic energy transfer (EET) is a mechanism describing energy transfer between two light-sensitive molecules (chromophores). A donor chromophore, initially in its electronic excited state, may transfer energy to an acceptor chromophore through nonradiative dipole-dipole coupling. The efficiency of this energy transfer is inversely proportional to the sixth power of the distance between donor and acceptor, making FRET extremely sensitive to small changes in distance.

Measurements of FRET efficiency can be used to determine if two fluorophores are within a certain distance of each other. Such measurements are used as a research tool in fields including biology and chemistry.

FRET is analogous to near-field communication, in that the radius of interaction is much smaller than the wavelength of light emitted. In the near-field region, the excited chromophore emits a virtual photon that is instantly absorbed by a receiving chromophore. These virtual photons are undetectable, since their existence violates the conservation of energy and momentum, and hence FRET is known as a radiationless mechanism. Quantum electrodynamical calculations have been used to determine that radiationless (FRET) and radiative energy transfer are the short- and long-range asymptotes of a single unified mechanism.

When both chromophores are fluorescent, the term "fluorescence resonance energy transfer" is often used instead, although the energy is not actually transferred by fluorescence. In order to avoid an erroneous interpretation of the phenomenon that is always a non-radiative transfer of energy (even when occurring between two fluorescent chromophores), the name "Förster resonance energy transfer" is preferred to "fluorescence resonance energy transfer"; however, the latter enjoys common usage in scientific literature. It should also be noted that FRET is not restricted to fluorescence. It can occur in connection with phosphorescence as well.

One common pair fluorophores for biological use is a cyan fluorescent protein (CFP)-yellow fluorescent protein (YFP) pair. Both are color variants of green fluorescent protein (GFP). Labeling with organic fluorescent dyes requires purification, chemical modification, and intracellular injection of a host protein. GFP variants can be attached to a host protein by genetic engineering which can be more convenient. Additionally, a fusion of CFP and YFP linked by a protease cleavage sequence can be used as a cleavage assay.

A limitation of FRET is the requirement for external illumination to initiate the fluorescence transfer, which can lead to background noise in the results from direct excitation of the acceptor or to photobleaching. To avoid this drawback, Bioluminescence Resonance Energy Transfer (or BRET) has been developed. This technique uses a bioluminescent luciferase (typically the luciferase from *Renilla reniformis*) rather than CFP to produce an initial photon emission compatible with YFP. One drawback of BRET is the requirement to generate at least one fusion protein encoding luciferase, though some applications of FRET can be implemented with antibody-conjugated fluorophores.

BRET has also been implemented using a different luciferase enzyme, engineered from a deep-sea shrimp *Oplophorus gracilirostris*. This luciferase is smaller (19 kD) and brighter than the more commonly used luciferase from *Renilla reniformis*. Promega has developed this luciferase variant under the product name NanoLuc.

In general, "FRET" refers to situations where the donor and acceptor proteins (or "fluorophores") are of two different types. In many biological situations, however, researchers might need to examine the interactions between two, or more, proteins of the same type—or indeed the same protein with itself, for example if the protein folds or forms part of a polymer chain of proteins or for other questions of quantification in biological cells.

Obviously, spectral differences will not be the tool used to detect and measure FRET, as both the acceptor and donor protein emit light with the same wavelengths. Yet researchers can detect differences in the polarisation between the light which excites the fluorophores and the light which is emitted, in a technique called FRET anisotropy imaging; the level of quantified anisotropy (difference in polarisation between the excitation and emission beams) then becomes an indicative guide to how many FRET events have happened.

FRET has been used to measure distance and detect molecular interactions in a number of systems and has applications in biology and chemistry. FRET can be used to measure distances between domains in a single protein and therefore to provide information about protein conformation. FRET can also detect interaction between proteins. Applied in vivo, FRET has been used to detect the location and interactions of genes and cellular structures including intergrins and membrane proteins.

The applications of fluorescence resonance energy transfer (FRET) have expanded tremendously in the last 25 years, and the technique has become a staple technique in many biological and biophysical fields. FRET can be used as spectroscopic ruler in various areas such as structural elucidation of biological molecules and their interactions in vitro assays, in vivo monitoring in cellular research, nucleic acid analysis, signal transduction, light harvesting and metallic nanomaterial etc. Based on the mechanism of FRET a variety of novel chemical sensors and biosensors have been developed.

D. Kits

In still further embodiments, the present disclosure concerns kits for use with the detection methods described above. The detection kits will thus comprise, in suitable container means, one or more probes or primers that hybridize to target sequences, and optionally control detection reagents.

In certain embodiments, the probes or primers may be pre-bound to a solid support, such as a filter, a column matrix and/or well of a microtiter plate. The detection reagents of the kit may take any one of a variety of forms, including those detectable labels that are associated with or linked to the probe or primer.

The kits may further comprise a suitably aliquoted composition of a target sequence, as may be used to prepare a standard for a detection assay. The kits may contain primer/probe-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the probes or primers may be placed, or preferably, suitably aliquoted. The kits of the present disclosure will also typically include a means for containing the reagent containers in close confinement for commercial sale. Such containers may include injection or blow-molded plastic containers into which the desired vials are retained.

V. EXAMPLES

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Materials and Methods for UMD Using MBs

Random DNA probe design. In the design of molecular beacons (MBs) (Tyagi & Kramer, 1996) for random DNA probes, the length and GC content (ratio of G+C to other nucleotides) of the probe loop and stem sequences were considered to strike a balance between two factors: fluorescence signal level and probe stability. Signal intensity was especially important in this detection scheme, since no DNA amplification method (such as PCR) was utilized. Similar to sloppy molecular beacons (sloppy MBs) (Chakravorty et al., 2010), the inventors selected the random probe loop sequence to be longer that traditional MBs. In addition, the inventors made the stem sequence one nucleotide shorter to introduce additional sloppiness (i.e., hybridization in presence of more base-pair mismatches).

Figure 5:
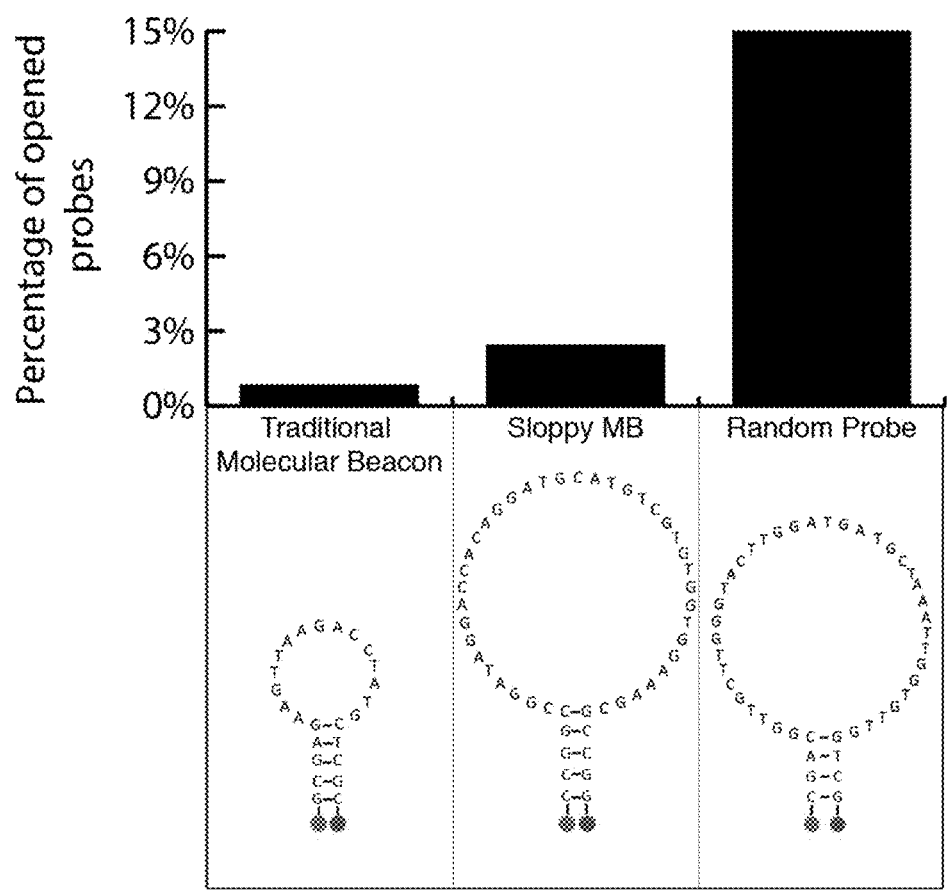
FIG. 5. Comparison of the sloppiness of random probes to other molecular beacons. The predicted number of opened probes when the *E. coli* genome is exposed to a specific (in the same thermodynamic condition as the experiment) traditional molecular beacon (MB) (SEQ ID NO: 12; Tyagi & Kramer, 1996), sloppy MB (SEQ ID NO: 13; Chakravorty et al., 2010), and an MB created according to random design rules (SEQ ID NO: 1). While the nucleotides in the loop were determined randomly, the percentage of opened beacons (hybridization affinity to *E. coli*) is substantially increased for the random probe MB, due to the choice of stem/loop length.

The challenge was to find probes that maintain the MB's signature hairpin structure over a wide range of temperatures (4-50° C.) after introducing additional sloppiness. To produce random MBs the inventors followed the following procedure: The inventors first generated one million random sequences of length 46 nucleotides with fixed stem sequences on both ends (FIG. 2A). Then, the inventors used a package in the DNA software (Visual OMP DE) to generate all the possible stable and secondary structures of the sequences in the experimental thermodynamic conditions. The inventors parsed the output of the DNA software and filtered out the probes with undesired secondary structures or melting temperatures. FIG. 5 shows the gain in hybridization affinity obtained using the random MBs in comparison with traditional MBs and sloppy MBs in binding to the E. coli genome. By no means is this the only method to generate random probes for a UMD platform; any method that produces probes with a stable hairpin structure and uniform melting temperature while providing the required signal intensity can be utilized.

Random DNA probe construction and preparation. To implement the Universal Microbial Diagnostics (UMD) platform, the inventors obtained DNA oligonucleotides for the random DNA probes and their exact complements from Integrated DNA Technologies (Coralville, Iowa). The sequences are provided below. MgCl$_2$, KCl, and sterile nuclease-free water for making the molecular beacon (MB) buffer were purchased from Fisher Scientific (Waltham, Mass.). 1M Tris-HCl solution (pH 8.3) and Tris-EDTA buffer (TE buffer; 10 mM Tris-HCl, 0.1 mM EDTA pH 8) were obtained from Teknova (Hollister, Calif.). To prevent nuclease contamination, all work surfaces and materials were routinely cleaned with RNAse OFF decontamination solution (Takara, Japan).

Random probe 1:
(SEQ ID NO: 1)
5'-/5Cy5/CGA CGG TTG CTT GGG TAC TTG GAT GAT GCT AAA TTG GTG TTG GTC G/3Cy3Sp/-3', Random probe 2:
(SEQ ID NO: 2)
5'-/5Cy5/CGA CGG TGC TTT GAA TAC TTG GTA GAG GCT GGA GGG TGG TTG GTC G/3Cy3Sp/-3', Random probe 3:
(SEQ ID NO: 3)
5'-/5Cy5/CGA CGG TGC TGG GTG AAC TAA AGG GTG GGT GCT ATG GGA AGG GTC G/3Cy3Sp/-3', Random probe 4:
(SEQ ID NO: 4)
5'/5Cy5/CGA CTT AAT GAA TGT GTG GGC GCT TGG TTG CTT AAT GAG TGG GTC G/3Cy3Sp/-3',
and Random probe 5:
(SEQ ID NO: 5)
5'-/5Cy5/CGA CGT TTC TTT TCT GGA GGA GGG AGG GTT AGT TGT TAG GCA GTC G/3Cy3Sp/-3'.

Random probe complement 1:
(SEQ ID NO: 6)
5'-CGA CCA ACA CCA ATT TAG CAT CAT CCA AGT ACC CAA GCA ACC GTC G-3', Random probe complement 2:
(SEQ ID NO: 7)
5'-CGA CCA ACC ACC CTC CAG CCT CTA CCA AGT ATT CAA AGC ACC GTC G-3', Random probe complement 3:
(SEQ ID NO: 8)
5'-CGA CCC TTC CCA TAG CAC CCA CCC TTT AGT TCA CCC AGC ACC GTC G-3', Random probe complement 4:
(SEQ ID NO: 9)
5'-CGA CCC ACT CAT TAA GCA ACC AAG CGC CCA CAC ATT CAT TAA GTC G-3',
and Random probe complement 5:
(SEQ ID NO: 10)
5'-CGA CTG CCT AAC AAC TAA CCC TCC CTC CTC CAG AAA AGA AAC GTC G-3'.

Generation of random probe characteristic curves. The experimentally measured fluorescence resonance energy transfer (FRET), defined as the ratio of Cy5 intensity over total fluorescence intensity (Cy3+Cy5), is a function of the concentration of open random probes in the solution, i.e., the probe-target hybridization affinity. To discern the hybridization affinity between a probe and target in units of molarity rather than as a FRET ratio, a characteristic curve was constructed for each probe. These curves presented the FRET ratio as a function of the concentration of open probes in molarity.

Figure 6:
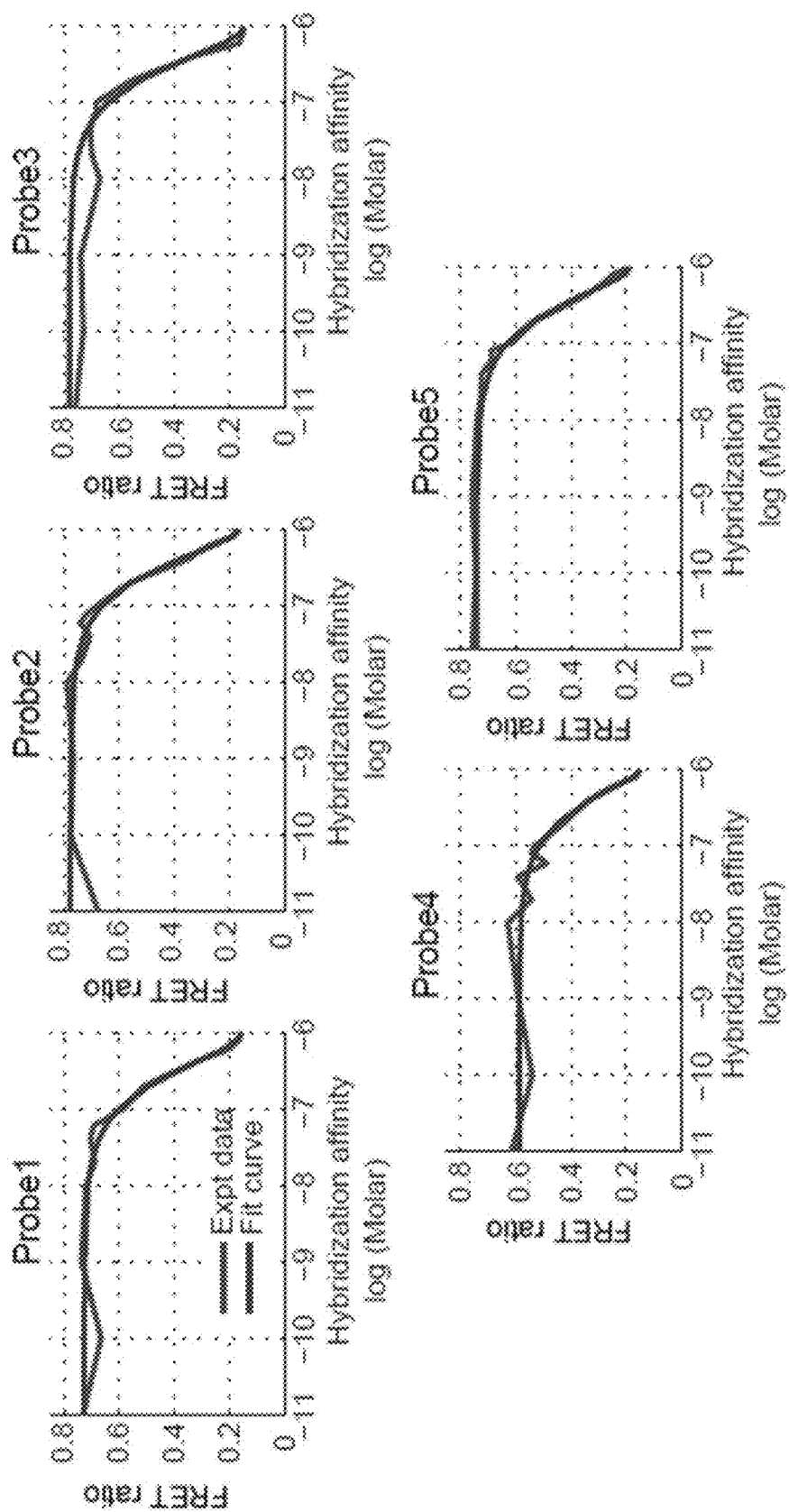
FIG. 6. Random probes' characteristic curves. Probe characteristic curves for random probes 1-5 for determining the experimental relationship between FRET ratio and open MB concentration (hybridization affinity). The characteristic curve is fitted to the measured FRET ratio as a function of the concentration of the probe's exact complement for five random probes.

To obtain the characteristic curves, random probes were diluted to 1 µM in 1× MB buffer (4 mM MgCl$_2$, 50 mM KCl, 10 mM Tris-HCl, pH=8, in sterile RNAse free water). DNA oligonucleotides perfectly complementary to the random probes were diluted using 1× TE buffer to $10^{-5}$, $10^{-6}$, $8\times10^{-7}$, $6\times10^{-7}$, $4\times10^{-7}$, $2\times10^{-7}$, $10^{-7}$, $8\times10^{-8}$, $6\times10^{-8}$, $4\times10^{-8}$, $2\times10^{-8}$, $10^{-8}$, $10^{-9}$, $10^{-10}$, or $10^{-11}$ M concentration. 25 µL of 1 µM random DNA probes (diluted in MB buffer) were added to 25 µL of perfect complement DNA of various concentrations, or to the TE buffer-only control. The DNA mixture was briefly centrifuged with a mini centrifuge (VWR) to collect all DNA to the bottom of the tube. Then the DNA was hybridized using a MyCycler Thermal Cycler (Bio-Rad) under the following conditions: 95° C. for 5 minutes, 50° C. for 2 minutes, 30° C. for 1 minute, 20° C. for 1 minute, and 4° C. for 2 minutes. 45 µL of each thermal cycled mixture was added to 155 µL 1× MB buffer in a black flat bottom 96 well plate (Corning) and kept at 4° C. overnight. A non-linear optimization algorithm (22) was utilized to fit the parameters a, b, n and $FRET_0$ to the characteristic curve: $FRET(c)=FRET_0+a/(1+b\ (10^{-6}-c)^{-n})$ (FIG. 6). The coefficient of determination ($R^2$) and root mean square error (RMSE) for the curve fits are reported in Table 1.

Bacterial DNA extraction. Overnight cultures of S. aureus USA 300 and E. coli MG1655 were used to inoculate fresh cultures grown in 50-100 mL 2× TY or Luria-Bertani (LB) broth, respectively. F. tularensis LVS was obtained from Dynport Vaccine Company LLC (derived from NDBR101 Lot 4) and grown in modified Mueller-Hinton cation-adjusted (MHII) broth (Becton Dickinson) supplemented with sterile 0.1% glucose, sterile 0.025% ferric pyrophosphate, and 2% reconstituted IsoVitaleX (Becton Dickinston). Cultures were pelleted and washed three times with sterile PBS. To release chromosomal DNA cells were resuspended in TE buffer and mixed with 10% sodium dodecyl sulfate (SDS) and Proteinase K at 65° C. overnight. DNA was isolated using phenol: chloroform and precipitated via ethanol precipitation (protocol adapted from elsewhere (Sambrook et al., 2001)). DNA pellets were resuspended in 50 μL TE buffer and stored at −20° C.

Bacterial strains, C. jejuni, P. mirabilis, C. metallidurans, M. luteus, B. dentium, E. aerogenes, B. fragilis, and P. aeruginosa were grown overnight in 30 mL Brain Heart Infusion (BHI) media (BD) at 37° C. Bacterial cells were pelleted, washed two times with sterile 1× PBS, and resuspended in TE buffer. Proteinase K (1 mg/mL) (Sigma) and 0.5% SDS were added to the bacterial cells, which were then incubated overnight at 55° C. on an orbital shaker. The samples were then mixed with phenol-chloroform (Invitrogen) and centrifuged; supernatants were transferred to a fresh tube. This aqueous phase was then mixed with an equal volume of chloroform and centrifuged (and repeated). Finally, 1/10 volume of 2 M sodium chloride and an equal volume of isopropanol was added to precipitate the DNA. This mixture was incubated at −20° C. for 30 min and centrifuged. The pellets were rinsed with 70% ethanol, air dried, and resuspended in TE buffer.

Random probe and bacterial DNA hybridization. Bacterial DNA was diluted to approximately 500 ng/μL using TE buffer and kept at −20° C. until use. The random MB probes were diluted to 1 μM in MB buffer prior to use. 25 μL of 1 μM random probes (diluted in MB buffer) was added to 25 μL of TE buffer control and E. coli, F. tularensis, S. aureus, C. jejuni, P. mirabilis, C. metallidurans, M. luteus, B. dentium, E. aerogenes, B. fragilis, or P. aeruginosa DNA. The DNA mixture was briefly centrifuged to collect DNA and then hybridized using a MyCycler Thermal Cycler (Bio-Rad) under the following conditions: 95° C. for 5 minutes, 50° C. for 2 minutes, 30° C. for 1 minute, 20° C. for 1 minute, and 4° C. for 2 minutes. 45 μL of each thermal cycled mixture was added to 155 μL 1× MB buffer in a black flat bottom 96 well plate (Corning) and kept at 4° C. overnight.

Measuring FRET ratio through fluorescence as indicator of random probe-bacteria hybridization. The FRET ratio for the genomic DNA samples following hybridization with each of the random probes was determined by reading the Cy3 and Cy5 fluorescence using a Fluorolog-3 spectrofluorometer (Jobin Yvon Horiba, Edison, N.J.) coupled with a MicroMax 384 MicroWell Plate Reader and water-cooled PMT detector. Samples were excited at 545 nm, and single point fluorescence measurements were taken with at 562 nm and 677 nm emission (optimal wavelengths determined through excitation-emission matrix analysis) to measure the Cy3 and Cy5 fluorescence, respectively. The FRET ratio was calculated as Cy5/(Cy5+Cy3).

Determining DNA hybridization affinity via SantaLucia thermodynamic models. A comprehensive thermodynamic model by SantaLucia et al. (SantaLucia & Hicks, 2004) was utilized to predict the hybridization of probes to bacterial genomes. The SantaLucia model incorporates thermodynamic parameters for mis-hybridizations between two DNA sequences. The inventors utilized two software packages: ThermoBlast DE, which performs fast alignment of sequences against large genome databases to discover thermodynamically stable hybridizations, and Visual OMP DE, which simulates hybridization experiments with detailed solution conditions and generates results for melting temperature (Tm), Gibbs free energy (ΔG), and the percentage-based concentration of each resultant species post-experiment. The secondary structure of each monomer, homodimer, and heterodimer species formed from the constituent probes and target fragments can also be visualized.

To calculate the hybridization affinity of a genome to a probe, the inventors first used the ThermoBlast package and thermodynamically aligned the sequence of the random probe to both complement strands of the target genome. The inventors extracted all the sequence fragments of the genome (100-200 nucleotides) that aligned with the probe sequence with a predicted melting temperature within approximately 35° C. of the melting temperature of the sequence genome. They then used Visual OMP DE to simulate the hybridization between the probe and the target genome, using the target fragments (FIG. 2). Every simulation contained information on the probe sequence, the target fragment sequences, and conditions for the experiment, including probe concentration (1 μM), unit target concentration (500 ng/μL for all bacteria), assay temperature (4° C.), hybridization buffer composition (4 mM Mg++, 50 mM Na+, 0 M Glycerol, 0 M DMSO, 0 M Formamide, 0 M TMAC, 0 M Betaine), and pH 8. This procedure was repeated for each probe-target genome pair. The inventors used the percentage of probe-target heterodimer structures formed, i.e., the percentage of probes that are bound to target fragments, as an estimate for the hybridization affinity of the probe to each target (FIG. 2B).

Linearity assumption considerations in UMD. In the UMD platform, the probe concentration ($1 \times 10^{-6}$ M) is in far excess of the target concentrations (~$1 \times 10^{-10}$ M); therefore, the inventors are able to linearly combine the hybridization affinity signatures that they measure for individual targets using the hybridization model. Due to the flooding of excessive number of probes, each target fragment has its choice of binding/not binding to the probes, and thus the inventors can safely sum together multiple target interactions of the same probe, assuming them to be independent.

Receiver-operator curve (ROC) analysis. Receiver-operator curve (ROC) analysis was performed by plotting a ROC curve showing the sensitivity and (1-specificity) for 1000 threshold values ranging from −1 to 1. For each threshold value, the following procedure was performed on the data matrix of normalized inner products between the experimentally obtained hybridization affinity and predicted hybridization affinities (by thermodynamic model) for the nine independent bacterial DNA samples (FIG. 3C): Each entry in the inner product data matrix was compared with the threshold value to determine the number of true positives, false positives, true negatives, and false negatives. True positives were identified when values in the diagonal entries of the inner product data matrix were greater than the threshold value since diagonal entries represent the correct classification of the bacterial sample with its corresponding genus in the database. False positives were identified as off-diagonal values that were greater than the threshold value. True negatives were identified as off diagonal values that were less than or equal to the threshold value. False negatives were identified as diagonal values that were less than or equal to the threshold value. For each threshold value, sensitivity was defined as (# true positives/(# true positives+# false negatives)) and specificity was defined as (# true negatives/(# true negatives+# false positives)).

Greedy probe selection. Given a set of P random probes, finding the set of M probes with the best detection performance in terms of sensitivity and specificity is an extremely challenging problem. A brute force search would require one to search among all $$\binom{M}{P}$$

possible combination of M probes to find the optimal probe set. This combinatorial search algorithm grows quadratic with P and thus becomes computationally intractable when the number of probes grows. The inventors thus developed a rapid probe selection method that the inventors dub Greedy Probe Selection (GPS). With a small sacrifice in sensitivity, GPS finds the best performance probe in a few seconds: exponentially faster than the naïve search method. The algorithm in each iteration finds the probe that maximizes a detection performance criterion (here the maximum pairwise correlation of bacteria) and adds it to the list of probes picked from the previous iterations. GPS stops when the maximum desired number of probes is reached.

Mathematical formulation of the compressive sensing (CS) detection and estimation algorithms. First, the inventors set up a mathematical model. Recall that there are N target bacteria of interest. Each microbial sample is characterized by a concentration vector $x=[x_1, x_2, x_3, \ldots, x_N]^T$ containing the concentration $x_i$ of bacterium i. While the total number of target species N might be large, a typical contaminated or infected sample will contain only a few target species K with significant concentration. When N»K, the inventors say that the vector x is sparse. Experimental quantification of the amount of hybridization between the DNA of the microbial sample and M random probes produces the probe-binding vector $y=[y_1, y_2, y_3, \ldots, y_M]^T$ containing the hybridization binding level $y_j$ of the sample to probe j. By predicting the hybridization binding level $\varphi_{ij}$ of probe i to bacterium j from the database of targets of interest, one can form the M×N hybridization affinity matrix $\Phi$ (FIG. 1B and FIG. 2B). The inventors refer to column i of the matrix $\Phi$ by the column vector $\varphi_{ij}$.

As described in above, the probe-binding vector y will approximately form as a linear combination of the predicted hybridization affinities of the species in the reference genome database (the columns of the matrix $\Phi$) weighted by their concentrations x, i.e.:

$$y=\Phi x+n$$

Here the vector n accounts for noise and modeling errors.

Two goals of UMD are to detect the presence and estimate the concentrations x of a potentially large number N of reference microbial genomes in a sample given only a small number M×N of probe-binding vector measurements y. Simply inverting the matrix $\Phi$ is impossible in this case, since it has many more columns than rows. Fortunately, it is reasonable to assume that only a small number K of microbial genomes will be present in a given sample, in which case the concentration vector x is sparse with K nonzero and N−K zero (or close to zero) entries; when K<M, one can hope to invert $\Phi$ to estimate the K nonzero concentrations. In order to apply the standard compressive sensing theory, the columns of $\Phi$. should satisfy the so-called Restricted Isometry Property (RIP). It has been shown that a matrix satisfies the RIP if its columns are sufficiently incoherent (Baraniuk, 2011), i.e., when the largest normalized inner product between any two columns of $\Phi$:

$$\mu = \min_{\forall i,j:i\neq j} \frac{\varphi_i^T \varphi_j}{\|\varphi_i\|_2 \|\varphi_j\|_2},$$

known as the coherence, is bounded above by a small constant. More specifically, it has been shown (Donoho & Xiaoming, 2001) that $\mu<1/(2K-1)$ is a sufficient condition to exactly recover a K-sparse signal with only $M=cK\log(N/K)$, where c is a small constant, measurements in the noise-free scenario when n=0.

In the presence of noise, the same sufficiency bound holds if the magnitudes of the non-zero elements of x are sufficiently large compared to the noise variance (Cai & Wang, 2011). When these conditions hold, the inventors can both detect the presence of bacteria and estimate their concentration using standard CS signal recovery algorithms. In the UMD platform, both the hybridization matrix $\Phi$ and the sparse concentration vector x are non-negative. A more optimistic recovery bound has been proven to hold in this regime. In particular, an alternative notion of incoherence is defined (Bruckstein et al., 2008) that improves the recovery guarantee. For an arbitrary matrix $\Phi$, the one-sided coherence is defined as:

$$\rho(\Phi) = \min_{\forall i,j:i\neq j} \frac{\varphi_i^T \varphi_j}{\|\varphi_i\|_2^2}.$$

It is shown (Bruckstein et al., 2008) that, for a non-negative matrix $\Phi$, if a nonnegative K-sparse solution exists such that $\sigma(PD)<1/(2K-1)$, then the solution is unique and CS recovery algorithms can find it. Here D is defined as the column $L_i$ (sum)-normalized matrix of $\Phi$, and P is the column mean subtraction operator (Bruckstein et al., 2008). While the one-sided coherence recovery bound is based on the better-conditioned matrix PD, it remains pessimistic, and better recovery performance is typically achieved in practice. The concentration vector x is recovered from the measurement vector y via a sparsity-penalized optimization of the form $$\min_x \|x\|_0, \text{ subject to } \|y-\Phi x\|_2 < \sigma.$$

Here $\|x\|_0$, known as the $L_0$-norm, counts the number of non-zero values in the vector x, and $\Phi$ estimates the noise standard deviation. While this optimization problem has exponential complexity, a variety of different greedy algorithms have been developed to solve it approximately. Orthogonal Matching Pursuit (OMP) (Tropp & Gilbert, 2007) is an iterative greedy algorithm that, at each step, selects the column of $\Phi$ that is most correlated with a residual vector from the previous iteration. The primary advantages of OMP are its simplicity and fast convergence. Moreover, if the sparsity level K (the number of bacteria) is known, then the algorithm can use it as the stopping criterion. The inventors can leverage the fact that both the hybridization affinity matrix $\Phi$ and the sparse concentration vector x are non-negative to improve the performance of OMP. The inventors utilize the variant of OMP (Bruckstein et al., 2008) that is adapted to recover non-negative sparse solutions from non-negative sensing matrix $\Phi$. Instead of directly working on $\Phi$, this algorithm operates on the canonical matrix PD, where D is the column $L_1$-norm normalized version of matrix $\Phi$ defined as: $D=\Phi W^{-1}$, where W is an M×M diagonal matrix containing the column sums of the hybridization matrix $\Phi$ and P is the pre-conditioner matrix and can be chosen as any invertible N×N matrix. In the case of a positive matrix D, an efficient preconditioning can be obtained by subtracting the weighted mean of each column of D: $PD=(1-(1-\varepsilon)E/N)D$, where E is N×N matrix of ones, I is the identity matrix, and $0<\varepsilon\ll1$ is a weighing constant to make the P matrix invertible. Working with the preconditioned matrix PD does not change the solution of the problem (Bruckstein et al., 2008); however, it significantly improves the OMP algorithm behavior and performance guarantees. This OMP algorithm variant is given in Alg. 1 (Bruckstein et al., 2008):

---
Algorithm 1: Non-negative OMP
---
Data: D, y
Result: $x^i$
Initialization;
The temporary solution: $x_i = 0$;
The temporary residual: $r^i = y$;
The temporary solution support: $S^i = \text{support}\{x^i\} = \phi$.
While
    $\|r\|_2^2 \leq T$
    do
      Sweep:
        $\forall j \in [1,2,\sqcap, N]$:find $\epsilon(j) = \min_{x \geq 0} \|D_j x_j - r\|_2^2$
      Update support: find $j_0$ such that $\forall j \in S^i, \epsilon(j_0) \leq \epsilon(j)$;
      update $S^i = S^{i-1} \cup \{j_0\}$;
      Update solution: compute
        $x^i : x^i = \min_{x \geq 0} \|Dx - y\|_2^2$ subject to
        support$\{x^i\} = S^i$;
      Update residual: compute $r^i = y - Dx^i$;
End
---

The inventors set the stopping criterion to $T=2\times10^{-1}$ for recovering the experimentally obtained hybridization affinity vectors in FIG. 3 and the numerically simulated hybridization affinity vector corrupted by modeling noise level in FIG. 4. $T=7\times10^{-3}$ was selected to recover the simulated hybridization affinity vector corrupted by the experimental noise level simulations in FIG. 4. In reporting the similarity of the experimentally measured hybridization affinity vectors in FIG. 3D, the inventors have reported the similarity of measured hybridization affinity vector y in each experiment to the bacteria i in the dictionary as the inner product of the normalized affinity vector $y/\|y\|_2$ and the $i_{th}$ column of the normalized preconditioned matrix PD. The inner product is a unit-less number in the range $[-1,1]$, where 1 indicates the highest similarity and $-1$ the lowest similarity.

Complete list of bacterial strains used in UMD simulations. To evaluate the UMD platform for genus level bacterial detection, the inventors selected 40 species from 40 different genera that are listed among most commonly pathogenic to humans by the Center for Disease Control and Prevention (CDC). The genome sequences of the following strains were obtained from the NCBI website:

Acinetobacter baumannii ATCC 17978,
    Aeromonas salmonicida subsp. salmonicida A449,
    Bacteroides fragilis 638R,
    Bacillus cereus ATCC 14579,
    Bartonella henselae str. Houston-1,
    Bifidobacterium dentium Bd1,
    Bordetella pertussis Tohama,
    Borrelia burgdorferi B31,
    Brucella abortus S19,
    Campylobacter jejuni subsp. jejuni 81116,
    Clostridium botulinum B1 str. Okra,
    Corynebacterium jeikeium K411,
    Coxiella burnetii RSA 331,
    Cupriavidus metallidurans CH34,
    Enterobacter aerogenes EA1509E,
    Enterococcus faecalis V583,
    Escherichia coli str. K-12 substr. MG1655,
    Francisella tularensis subsp. holarctica LVS,
    Fusobacterium nucleatum subsp. nucleatum ATCC 25586,
    Haemophilus influenzae F3047,
    Helicobacter pylori B38,
    Klebsiella pneumoniae 342,
    Legionella pneumophila str. Corby,
    Leptospira interrogans serovar Copenhageni str. Fiocruz L1-130,
    Listeria monocytogenes 08-5578,
    Micrococcus luteus NCTC 2665,
    Mycobacterium leprae TN,
    Mycoplasma pneumoniae M129,
    Neisseria meningitidis MC58,
    Prevotella melaninogenica ATCC 25845,
    Propionibacterium acnes KPA171202,
    Proteus mirabilis HI4320,
    Pseudomonas aeruginosa LESB58,
    Rickettsia rickettsii str. Iowa,
    Salmonella enterica subsp. enterica serovar Paratyphi A str. ATCC 9150,
    Serratia proteamaculans 568,
    Shigella sonnei Ss046,
    Staphylococcus aureus subsp. aureus USA300 FPR3757,
    Vibrio cholerae MJ-1236, and
    Yersinia pestis CO92.

For species-level bacterial detection, the following 24 different strains from the Staphylococcus genus were selected to perform the simulations:

Staphylococcus arlettae CVD059 SARL-c1,
    Staphylococcus aureus subsp. aureus NCTC 8325,
    Staphylococcus auricularis strain DSM 20609,
    Staphylococcus capitis subsp. capitis strain AYP1020,
    Staphylococcus carnosus subsp. carnosus TM300,
    Staphylococcus cohnii subsp. cohnii strain 532,
    Staphylococcus epidermidis ATCC 12228,
    Staphylococcus equorum strain KS1039,
    Staphylococcus gallinarum strain DSM 20610,
    Staphylococcus haemolyticus JCSC1435,
    Staphylococcus hominis subsp. hominis C80,
    Staphylococcus hyicus strain ATCC 11249,
    Staphylococcus lentus F1142 s6-trimmed-contig-1,
    Staphylococcus lugdunensis HKU09-01,
    Staphylococcus massiliensis CCUG 55927,
    Staphylococcus pettenkoferi VCU012,
    Staphylococcus pseudintermedius HKU10-03,
    Staphylococcus saprophyticus subsp. saprophyticus ATCC 15305,
    Staphylococcus schleiferi strain 2317-03,
    Staphylococcus sciuri subsp. sciuri strain DSM 20345,
    Staphylococcus simiae CCM 7213 contig00565,
    Staphylococcus simulans ACS-120-V-Sch1,
    Staphylococcus vitulinus F1028 S-vitulinus-F1028-0001, and
    Staphylococcus warneri SG1.

For species-level bacterial detection, the following 23 different strains from the Vibrio genus were selected to perform the simulations:

Vibrio anguillarum 775,
    Vibrio brasiliensis LMG 20546 VIBR0546-99,
    Vibrio cholerae O1 biovar El Tor str. N16961,
    Vibrio cyclitrophicus FF75 Ctg1,
    Vibrio diazotrophicus NBRC 103148,
    Vibrio ezurae NBRC 102218,
    Vibrio furnissii NCTC 11218,
    Vibrio genomosp. F6 str. FF-238,
    Vibrio genomosp. F10 str. ZF-129,
    Vibrio harveyi ATCC BAA-1116,

*Vibrio litoralis* DSM 17657,
*Vibrio maritimus* strain: JCM 19235,
*Vibrio metschnikovii* CIP 69.14 VIB.Contig153,
*Vibrio nigripulchritudo* str. SFn1,
*Vibrio orientalis* CIP 102891 ATCC 33934 strain CIP 102891,
*Vibrio pacinii* DSM 19139 BS19DRAFT-scaffold00001.1-C,
*Vibrio parahaemolyticus* RIMD 2210633,
*Vibrio proteolyticus* NBRC 13287,
*Vibrio rhizosphaerae* DSM 18581,
*Vibrio scophthalmi* LMG 19158 VIS19158-99,
*Vibrio splendidus* LGP32,
*Vibrio tubiashii* ATCC 19109, and
*Vibrio vulnificus* YJ016.

Example 2

Results for UMD Using MBs

Figure 7:
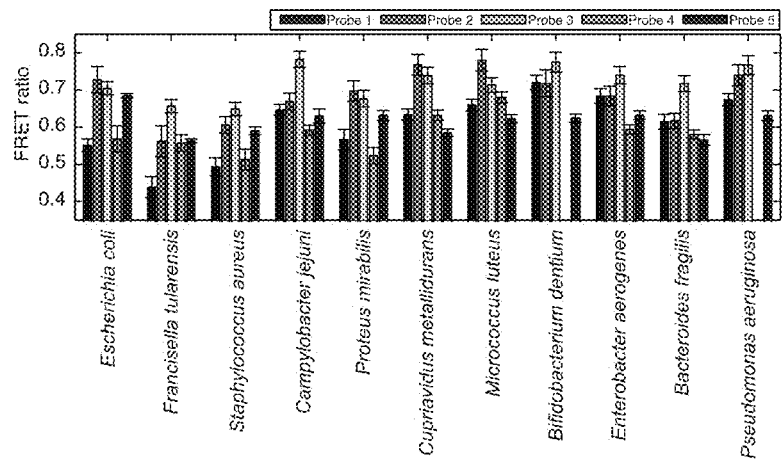
FIG. 7. Experimentally measured FRET ratios to quantify hybridization between 11 bacterial DNA samples and probes 1-5. The error bars represent the standard error of the mean (s.e.m.).
Figure 8:
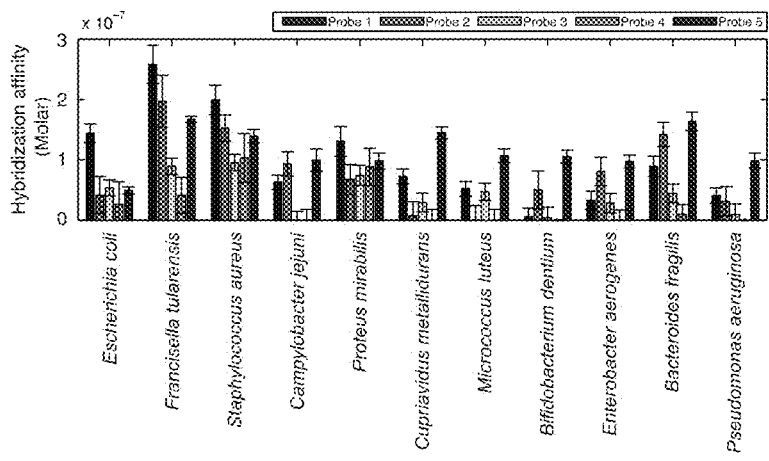
FIG. 8. Hybridization affinity between 11 bacterial DNA samples and probes 1-5. Converted from FRET ratio through the probe characteristic curve fit equations. The error bars represent the standard error of the mean (s.e.m.).

Experimental proof of concept. To prove the UMD concept, the inventors mixed five UMD MBs (as shown in FIG. 2A and characterized in FIG. 6 with GC-contents 50, 56.5, 60.8, 50, and 52.7%, identical melting temperature of 40° C., and concentration 1 μM) in separate tubes (to prevent cross hybridization of probes) with genomic DNA from each of nine human infectious bacterial strains grouped into three categories: I. Exact sequence known (*Escherichia coli, Francisella tularensis, Staphylococcus aureus, Campylobacter jejuni*, and *Proteus mirabilis*), II. Exact sequence unknown (*Cupriavidus metallidurans* and *Micrococcus luteus*), and III. Clinical isolates, whose exact sequence is unknown (*Bacteroides fragilis* and *Enterobacter aerogenes*) The identification of *Pseudomonas aeruginosa* and *Bifidobacterium dentium* strains, was tested using four random probes (see FIGS. 7-9 for detection results). For bacteria in groups II and III, the DNA sequences in the database might not exactly match the sequences present in the bacterial samples.

For each MB-bacterial species pair, equal volumes of probe and bacterial DNA were combined and subjected to a thermal cycling process of denaturing (95° C.) and binding/cooling to 4° C. overnight. To quantify probe-DNA binding, the MB probes' Cy3 and Cy5 fluorescence intensities were measured with a fluorometer, and the fluorescence resonance energy transfer (FRET) ratios (a decrease represents MB opening due to DNA binding) were calculated by computing Cy5 intensity over total fluorescence intensity (Cy3+Cy5). The FRET ratios from binding of the nine bacteria to the MBs are depicted in FIG. 3A.

In order to estimate the bacterial concentrations in physical units, the inventors translated the FRET ratio of each bacterium-MB pair into the concentration of opened MBs or hybridization affinity, represented in units of molarity. For this, they experimentally obtained and fitted FRET ratios for each of the five MBs as a function of the concentration of their exact probe complements, using an optimization method described in (Jeričević and Kušter, 2005) (FIG. 6) (see Table 1 and Example 1 for the fit curve parameters and fit method, respectively). The $R^2$ values for the fits ranged from 0.97 to 0.99, suggesting a satisfactory fit. Based on the fit equations, the hybridization affinities corresponding to the FRET ratios for all bacteria were calculated. The inventors refer to these measurements as the measured hybridization affinity vectors and show them in FIG. 3B. The challenge was to decode the experimentally measured affinities of the bacterial species samples reacting to UMD MBs using compressive sensing recovery techniques. With the predicted hybridization affinities of N=9 bacteria to M=5 random probes stored in the computationally obtained $\Phi_{5\times 9}$, the inventors used a variant of the Orthogonal Matching Pursuit (OMP) algorithm (Bruckstein et al., 2008) and successfully identified the species present in each of the samples (FIG. 3). UMD estimated the relative bacterial concentrations with an average error of 11.5% (FIG. 10).

To provide the physician or scientist with a metric quantifying how close the measured hybridization affinity vector is to that of each bacteria in the database and thus how confident the OMP detection results are, UMD can output the inner products between the normalized measured hybridization affinity vectors from the nine experiments and the columns of the centered and normalized matrix $\Phi_{5\times 9}$ (FIG. 3C). This metric measures the similarity of a pathogenic sample to bacteria in the UMD database. Using this metric, the inventors characterized the performance of UMD in identifying the nine pathogens in terms of false positives and false negatives. The inventors constructed the receiver operating characteristic (ROC) curve (FIG. 3D), where each point on the curve corresponds to a certain universal detection threshold in the range [−1,1] for all nine independent bacterial experiments. Inner product values above/below the detection threshold were considered as a positive/negative outcome, respectively. The area under the corresponding ROC curve (AUC=0.91) suggests successful screening performance. FIG. 3E additionally shows the consistency of the measured and simulated hybridization affinities of nine bacteria to five random probes (different probes are shown in different colors). The normalized root-mean-square error NRMSE=12%, suggests that the inventors' thermodynamic modeling of bacteria-probe hybridization is accurate.

Next, the inventors assessed the performance of UMD in detecting these nine test species from a list of common pathogens using the five DNA probes. The inventors expanded the reference genome database to contain 40 genera (i.e., M=5«N=40), including bacterial pathogens listed by the Centers for Disease Control and Prevention (CDC) as the most common notifiable human diseases (Centers for Disease Control and Prevention Morbidity and Mortality Weekly Report, 2013). With the most common pathogens' genomes in the database, the detection performance remained above AUC=0.84, suggesting a high recovery rate with only five random probes.

Extension by simulation. Thus far, the inventors have presented an experimental proof-of-concept that validates UMD's ability to detect eleven test species among a list of pathogens using a fixed set of five randomly selected test probes. The inventors next numerically demonstrate that, if a sufficient number of probes is used, then any group of randomly selected probes will detect the presence of one (K=1) or a mixture of several (K=2, 3, . . . ) pathogenic organisms in a sample out of a database of 40 pathogenic organisms. They introduced additive white Gaussian noise to the simulated hybridization affinity vectors to capture the variance in the hybridization affinities among the independent test trials in FIG. 3. The noise levels were extrapolated from the above eleven test bacteria experiments, with the noise variance set to $\sigma_0=2.4\times 10^{-8}$ M. In order to control for differences in the genome size of each organism, the inventors normalized numerical simulations to unit weight of bacterial DNA.

In FIG. 4A, the inventors first demonstrate the detection performance of UMD in identifying a single bacterium (K=1) among the pathogen database at different noise levels. As the ROC curves suggest, UMD's detection performance improves when the noise variance decreases. With only a five-fold decrease in the noise variance, UMD identifies all 40 bacteria in the database almost perfectly (AUC>0.95) using only five randomly selected probes.

The ability of UMD to universally detect target species can be improved by increasing the number of random probes. FIG. 4B demonstrates that UMD identifies all 40 bacteria in the CDC database almost perfectly (AUC=0.95) with any M=15 randomly selected MBs when the noise variance is similar to that measured experimentally (FIG. 3).

UMD has the unique advantage that it can recover more than a single (K>1) organism in an infectious sample. To evaluate the minimum number of probes M required for this task, the inventors used the Basis Pursuit De-Noising (BPDN) algorithm (as described in the Supplementary Materials) to identify the composition of a sample containing K={2,3} equi-concentration bacterial species (FIG. 4C). The inventors found that any set of M=15 randomly selected probes will recover all $$\binom{40}{K}$$

possible mixtures of K={2,3} pathogenic species in the CDC database. The error bars show the standard deviation over 1000 test trials with different sets of random MBs. This result confirms that the incoherence requirement for compressive sensing is empirically satisfied for the pathogenic strains in the CDC database and thus that UMD is capable of screening for pathogenic bacteria at the genus-level.

The inventors next evaluated UMD's performance for species-level bacterial detection. They focused on differentiating among 24 species of *Staphylococcus* genus and 23 species of *Vibrio* genus in silico. They identified the composition of samples containing *Staphylococcus* species using 11 random probes (FIG. 11A) and the composition of samples containing *Vibrio* species using 18 random probes (FIG. 11B) with high sensitivity and specificity (AUC>0.95). This underscores UMD's potential to differentiate pathogens at high taxonomic resolution.

Using the UMD platform, one can trade off between universality (detecting species outside of the library) and cost efficiency (number of probes). That is, it is possible to select a set of probes that achieves better detection performance in terms of specificity and sensitivity than the average performance of random probe sets at the cost of universality. For example, in FIG. 4C, some of the probe sets achieved 100% accuracy using three fewer probes than the number required for universal recovery. To capitalize on this phenomenon, the inventors developed a "greedy probe selection" (GPS) algorithm that rapidly selects these optimized probes given a very large database of genome-probe hybridization affinities.

FIGS. 4D-E, illustrate the UMD confusion matrices in detecting pathogenic bacteria using M=3 and M=10 probes selected using GPS. The false positive rate drops for all of the bacteria in the database as the number of probes increases from M=3 (AUC>0.95) to M=10 (AUC>0.99). While the performance detection is high (AUC>0.99), the confusion matrix shows few cases where the inner product values for possible species (e.g., *Coxiella*, *Aeromonas*, and *Proteus* when the actual sample contains *Coxiella*) are only slightly separated. FIG. 12 shows that greater separation between inner product values for candidate bacterial species can be achieved by using a larger number of UMD probes.

This can increase the robustness of the UMD system (ensure low false positive rate) for noisier environments.

Figure 13:
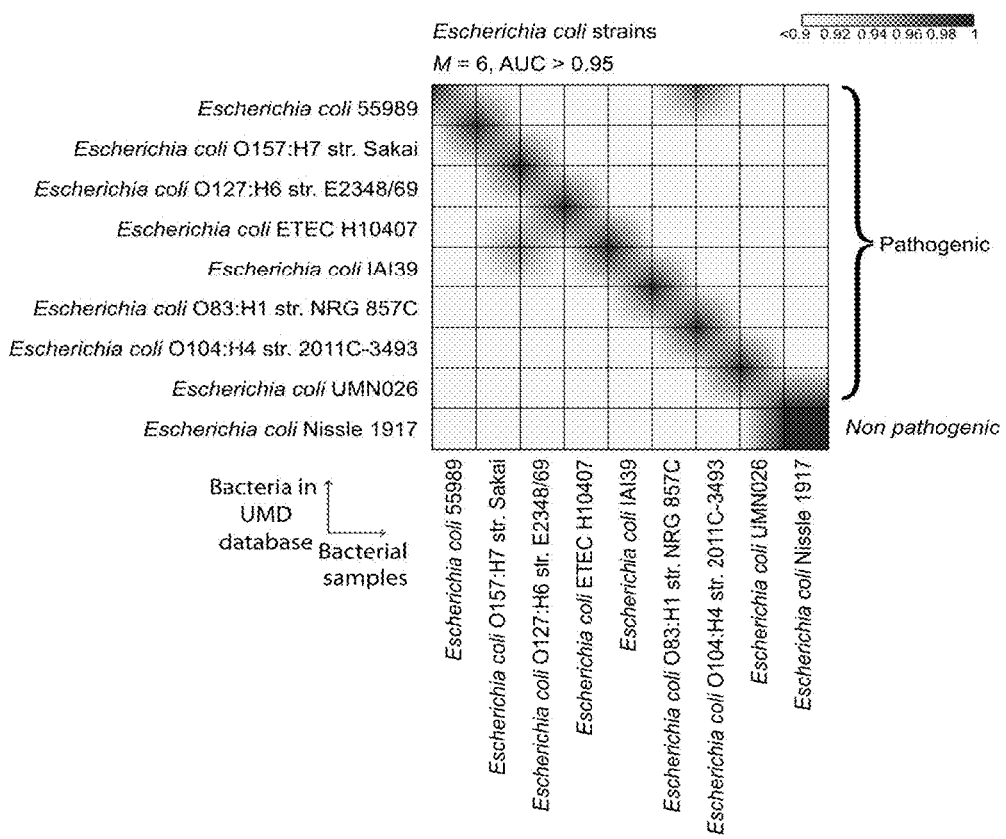
FIG. 13. Performance of UMD in identifying eight pathogenic and one nonpathogenic *E. coli* strains using GPS probes. GPS selects 6 UMD probes that differentiate between eight pathogenic and one nonpathogenic *E. coli* strains in silico.

While mainly intended to rapidly screen for pathogens at higher taxonomy levels, UMD can also provide strain-level information to the physician using additional GPS-selected probes. In FIG. 13, the inventors demonstrate that GPS selects UMD probes that differentiate among 9 strains of *E. coli* (8 pathogenic and one nonpathogenic) with high detection accuracy (AUC>0.95) in silico.

Figure 14:
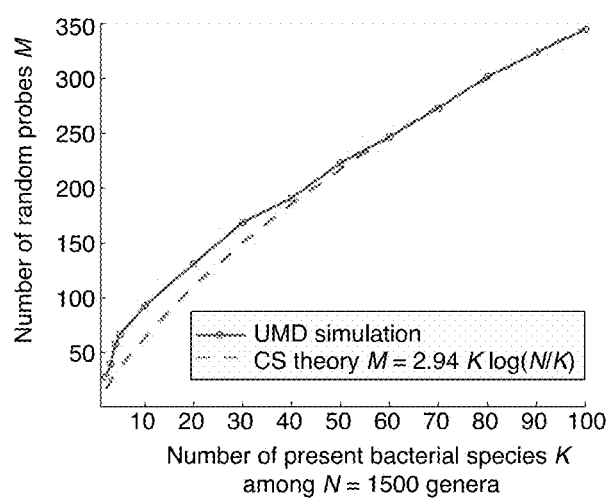
FIG. 14. Performance of UMD in identifying the composition of several complex samples. The inventors simulate the number of required random probes M to identify the composition of complex bacterial samples with 100% accuracy using UMD. The complexity of each sample is measured by the number of present bacterial species K among a total of N=1500 bacterial genera. To obtain each data point in the curve, the inventors randomly selected K bacterial genera from the database and created a sample by mixing K sample species from each genera with equal concentrations. They used UMD to recover the composition of the mixture using random probes, and repeated this same experiment for 1000 trials and reported the minimum number of probes that recovered all 1000 mixtures accurately. UMD requires orders of magnitudes less number of random probes than the size of the database N (i.e., number of probes typically required by conventional methods) to recover complex samples containing mixtures of K species (with equal concentrations) among N=1500 genera. Furthermore, number of required UMD probes closely ($R^2$=0.98) follows the number of probes predicted by the compressive sensing theory M=ck log(N/K) with c=2.94.

The theory behind the UMD can be extended to identify more complex samples using a relatively small number of random probes. The inventors verified that the UMD platform can recover complex microbial samples containing up to one hundred active species out of a large dictionary of N=1500 bacterial genera. They first computed the hybridization affinity of a set of random probes to N=1500 representative species of all sequenced bacterial genera in NCBI website. Then the inventors used the resulting hybridization affinity matrix to identify the composition of samples containing K unique species with equal concentrations (the most difficult case where the sample contains multiple species all at significant concentration). For each value of K, FIG. 14 shows the minimum number of random probes M required to identify the composition of 1000 simulated complex samples containing K species randomly selected from N=1500 genera. FIG. 14 illustrates that the number of required probes M closely ($R^2$=0.98) follows the compressive sensing theory M=cK log(N/K) with constant c=2.94. That is, UMD requires a number of probes that grows logarithmically with the number of target bacteria N and sub-linearly with the number of active bacteria K in the sample.

TABLE 1

The fitted parameters to the probes' characteristic curves.

| | Probe 1 | Probe 2 | Probe 3 | Probe 4 | Probe 5 |
|---|---|---|---|---|---|
| $\log_{10}(a)$ | 14.14 | 11.56 | 13.60 | 9.97 | 12.45 |
| b | 1.13 | 0.90 | 0.51 | 1.19 | 1.47 |
| n | 2.39 | 1.97 | 2.35 | 1.71 | 2.09 |
| $FRET_0$ | 0.161 | 0.165 | 0.152 | 0.148 | 0.183 |
| $R^2$ | 0.9877 | 0.9770 | 0.9688 | 0.9666 | 0.9899 |
| RMSE | 2.37E−2 | 3.33E−2 | 4.04E−2 | 2.90E−2 | 2.05E−2 |

Characteristic curve parameters a, b, and n for five test random probes, and the associated curve fit performance criteria, $R^2$, and root mean square error (RMSE) are tabulated. Parameters were fit to the following curve: $FRET(c) = FRET0 + a/(1 + b(10^{-6} - c)^{-n})$ (22).

Example 3

Discussion of UMD Using MBs

UMD probes are universal in the sense that a fixed set of probes captures the salient information required to distinguish between members of a large and growing database of species (Davenport et al., 2010). This gives UMD a potentially important future proof property: a fixed set of measurement probes can be used to detect and estimate the concentration of newly sequenced species not yet present in the library. To detect a new organism, the software merely has to be adjusted to take into account how the new organism will react to the existing probe set; however, new capture probes are not required. Moreover, since the number of probes grows only logarithmically in the size of the library, the UMD platform naturally contends with the data deluge (Baraniuk, 2011) from new microbial species being discovered and sequenced every day.

Several other pathogen detection schemes are currently under investigation (Chakravorty et al., 2010, Dai et al., 2009; Mohtashemi et al., 2011 and Chung et al., 2013). To the best of the inventors' knowledge, UMD is the only technique that enables a unified representation of bacterial organisms in a low-dimensional geometric space. The theory of compressive sensing provides rigorous recovery guarantees and suggests algorithms to leverage this geometry to both detect bacteria and estimate their concentrations efficiently. The inventors' successful implementation of UMD confirms that a small number of random DNA probes satisfy the incoherency requirements of compressive sensing theory and can be used for universal microbial sensing.

The UMD platform has the potential to rapidly direct physicians to use appropriate antibiotics or treatment and thus minimize the risk of antibiotic resistance. It can also be utilized in biodefense applications to classify multiple novel and mutant agents. With further optimization of the probe design and detection schemes, the inventors expect that UMD will be able to sense an even wider range of organisms (e.g., viruses, fungi) and various biomolecules of interest (genes, proteins).

Finally, the theory behind the UMD platform can be applied to DNA sensing in several other incarnations, including reads from a sequencer, e.g., one may be able to quickly identify a bacterium from a subset of reads, rather than requiring full alignment or assembly. Application of such signal acquisition principles to biological sensing systems will shape the future of microbial diagnostics.

Example 4

Use of the Insense Algorithm for Probe Selection

The Insense algorithm (Alg. 1; FIG. 16) was experimentally validated using a range of synthetic and real-world datasets. In all experiments, the following were set: $\in_1 = 10^{-9}$ and $\in_2 = 10^{-10}$ (anything in the range $\in_2 < \in_1 \ll 1$ can be utilized). Insense was terminated when the relative change of the cost function $\mu_{avg}^2(\Phi_\Omega)$ dropped below $10^{-7}$.

Baselines and performance metrics. Insense was compared with several leading sensor selection algorithms, including Convex Sensor Selection (Joshi & Boyd, 2009), Greedy Sensor Selection (Shamaiah et al., 2010), EigenMaps (Ranieri et al., 2012), and FrameSense (Ranieri et al., 2014). It was also compared with four greedy sensor selection algorithms that were featured in (Ranieri et al., 2014). The first three minimize different information theoretic measures of the selected sensing matrix as a proxy to the MSE: the determinant in Determinant-G (Steinberg & Hunger, 1984), mutual information (MI) in MI-G (Krause et al., 2008), and entropy in Entropy-G (Wang et al., 2004). The final greedy algorithm, MSE-G (Das & Kempe, 2008; Golovin et al., 2010; Das & Kempe, 2011), directly minimizes the MSE of the LS reconstruction error. The codes for these baseline greedy algorithms were obtained on the world wide web at github.com/jranieri/OptimalSensorPlacement. A comparison was also made with Random, a simple baseline that selects sensors at random.

The sensor selection algorithms were compared using the following six metrics:

Average coherence $\mu_{avg}(\Phi_\Omega)$.
Maximum coherence $\mu_{max}(\Phi_\Omega)$.
Frame potential FP($\Phi_\Omega$) (see (3))
Condition number CN($\Phi_\Omega$).
BP recovery accuracy.
Running time.

Depending on the task, in some experiments only a subset of the metrics are reported. To compute BP recovery accuracy, the performance of the BP algorithm (Chen et al., 1998) was averaged over multiple trials. In each trial, a K-sparse vector x whose non-zero entries are equal to one was first generated. Then, BP was used to recover x from linear, nonadaptive (noiseless) measurements $y = \Phi_\Omega x$.

The same experiment was repeated for all $$\binom{N}{K}$$

sparse vectors x with different support sets and the percentage of trials that x has been exactly recovered was reported. When $$\binom{N}{K}$$

is too large (here, greater than 10,000), the BP algorithm was run on a smaller random subset or all $$\binom{N}{K}$$

sparse vectors x.

Unstructured synthetic datasets. The sensor section algorithms were first tested by applying them to random matrices. It is easy to show that asymptotically (i.e., when $N \to \infty$) random matrices do not favor certain rows (sensors) over others. In the non-asymptotic regime (i.e., when N is finite) the choice of sensors for sparse recovery might be critical, since the probability that certain sets of sensors significantly outperform others increases. In this case, the sensor selection algorithm aims to identify these high-performing sensors. Three types of random sensing matrices $\Phi$ whose entries are drawn from Gaussian, Uniform, and Bernoulli distributions were generated and the performance of Insense was compared against the other baselines.

1) Random Gaussian matrix: This experiment was conducted for 20 random trials and 100×100 matrices $\Phi$ whose entries are independently drawn from a standard normal distribution were generated. Insense and other baseline algorithms were used to select $M \in \{5, 6, 7, \ldots, 30\}$ sensors. In FIGS. 17A&B, $\mu_{avg}$ and $\mu_{max}$ of the selected sub-matrices $\Phi_\Omega$ are reported, with $|\Omega|=M$. All of the sensor selection algorithms have comparable performance to the random sensor selection strategy (Random), illustrating that only small improvements to the maximum and average coherence can be achieved using these algorithms.

2) Random Uniform matrix: The previous experiment was repeated with a sensing matrix $\Phi$ whose entries were drawn uniformly at random from [0, 1]. FIG. 17C shows that Insense outperforms most of the baseline algorithms, including Random and Convex SS, in terms of $\mu_{avg}$. Despite selecting completely different sensors, FrameSense and EigenMaps have comparable performance to Insense in minimizing $\mu_{avg}$. FIG. 17D makes apparent the gap in maximum coherence $\mu_{max}$ between that achieved by Insense and the other baselines.

3) Random Bernoulli matrix: The previous experiment was repeated with a sensing matrix Φ whose entries are 0 or 1 with equal probability. In these experiments, the coherence minimization performance of all of the sensor selection algorithms was similar for Bernoulli (1/−1) matrices and Gaussian matrices. FIG. 17E shows that FrameSense, Eigen-Maps, and Insense have similar performance and outperform the other algorithms by a large margin in terms of average coherence $\mu_{avg}$. When a selected matrices $\Phi_\Omega$ contains one column with all zero entries, the average coherence $\mu_{avg}$ is not defined. The missing values in some curves correspond to these instances. FIG. 17F shows a clear gap between Insense and the other baselines in terms of the maximum coherence $\mu_{max}$.

In summary, Insense selects reliable sensors that are consistently better than or comparable to the other baseline algorithms on random sensing matrices. This suggests that Insense could find application in designing sensing matrices that outperform random matrices for CS recovery tasks.

Highly structured synthetic datasets. In contrast to random matrices, the sensing matrices in real-world applications often have imposed structures or redundancies. In such cases, careful sensor selection can mean the difference between low and high performance. Sensor selection was explored with structured over-complete matrices by constructing two synthetic datasets that resembled the redundancies and structures in real-world datasets. Similar over-complete basis has been explored in Chen et al. (1998).

1) Identity/Gaussian matrix: The first highly structured dataset was constructed by concatenating two 50×50 matrices: An identity matrix and a random matrix with i.i.d. Gaussian entries. Such matrices feature prominently in certain real-world CS problems.

For instance, in the universal DNA-based microbial diagnostics platform studied in Aghazadeh et al. (2016), the identity and Gaussian matrices symbolize two different types of sensors: the identity matrix corresponds to a set of sensors that are designed to be specific to a single microbial target (column) in the dictionary Φ, while the Gaussian matrix corresponds to a set of sensors that are universal for microbial targets in the dictionary. As in Aghazadeh et al. (2016), consider a bacterial detection scenario where the solution to the sparse recovery problem both detects and identifies the bacterial targets in a sample (through the support of the sparse vector x); here the goal is to maximize the average sparse recovery (detection) performance. On the one hand, if all of the sensors are selected from the identity submatrix, then nearly all of the selected sensors will lie dormant when detecting a particular bacterial target. On the other hand, if the sensors are selected from the Gaussian submatrix, then the selected sensors will work jointly to detect all bacterial targets, which provides both universality and better average sparse recovery performance (Aghazadeh et al., 2016). To achieve a better sparse recovery performance, the sensor selection algorithm should select rows (sensors) from the Gaussian submatrix rather than the identity submatrix.

Table 2 compares the performance of Insense to the baseline algorithms for the problem of selecting M=10 rows from the structured Identity/Gaussian Φ. The same experiment was repeated 10 times with different random Gaussian matrices. (Dashes correspond to instances where the selected matrices $\Phi_\Omega$ contain columns with all zero entries; here the average coherence $\mu_{avg}$ is undefined.) In particular, Insense, Convex SS, and MSE-G are the only algorithms that select rows of the Gaussian sub-matrix. While achieving the minimum FP($\Phi_\Omega$) (=0), the other algorithms perform poorly on BP recovery. The greedy algorithms select rows from the identity matrix that result in columns with allzero entries and thus fail to recover most of the entries in x. Digging deeper, Insense selects rows with smaller column coherence than Convex SS and MSE-G. As a result, Insense achieves the best BP recovery performance (Table 2) among these three algorithms.

In summary, this example demonstrates that minimizing a similarity metric imposed on the rows of the sensing matrix (such as frame potential, etc.) will not maximize the recovery performance of sparse signals. These results also provide reassurance that the coherence among the columns of the sensing matrix is a useful performance objective.

TABLE 2

Comparison of Insense against the baseline algorithms on selecting M = 10 rows from a structured identity/Gaussian Φ. Insense selected the set of sensors with the smallest $\mu_{avg}$ and achieved the best BP recovery performance.

|  | $\mu_{avg}(\Phi_\Omega)$ | FP($\Phi_\Omega$) | CN($\Phi_\Omega$) | BP accuracy % |
| --- | --- | --- | --- | --- |
| Insease | 0.3061 ± 0.0047 | 1019 ± 313 | 1.93 ± 0.19 | 92.27 ± 1.42 |
| FrameSense | — | 0.00 ± 0.00 | 1.00 ± 0.00 | 4.00 ± 0.00 |
| EigenMaps | — | 0.00 ± 0.00 | 1.00 ± 0.00 | 4.00 ± 0.00 |
| MSE-G | 0.3872 ± 0.0305 | 1155 ± 374 | 11.51 ± 0.93 | 57.91 ± 1.09 |
| MI-G | — | 0.00 ± 0.00 | 1.00 ± 0.00 | 4.00 ± 0.00 |
| Entropy-G | — | 0.00 ± 0.00 | 1.00 ± 0.00 | 4.00 ± 0.00 |
| Determinant-G | — | 0.00 ± 0.00 | 1.00 ± 0.00 | 4.00 ± 0.00 |
| Greedy SS | — | 0.00 ± 0.00 | 1.00 ± 0.00 | 4.00 ± 0.00 |
| Convex SS | 0.3137 ± 0.0075 | 2279 ± 470 | 2.22 ± 0.25 | 88.64 ± 3.64 |

2) Uniform/Gaussian matrix: To study the quality of the box constraint relaxation in (6), Insense was compared against the baseline algorithms for a matrix Φ where the globally optimal index set of rows (sensors) Ω is known. (For arbitrary Φ, global combinatorial optimization is computationally intractable when D, N>200 or so.)

Figure 18:
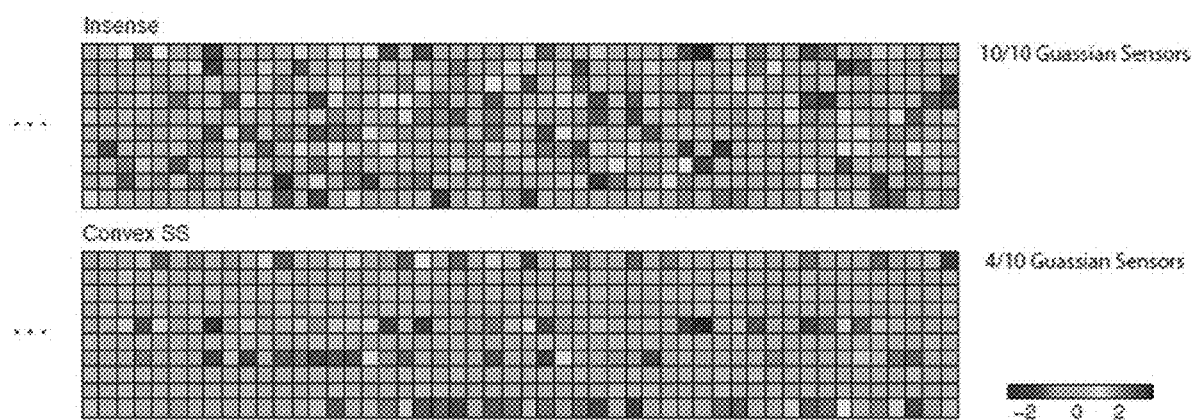
FIG. 18. Visualizations of the M=10 sensing matrices $\Phi_\Omega$ selected by Insense and Convex SS from a structured Uniform/Gaussian matrix. Insense selects 10/10 Gaussian rows (sensors), while Convex SS selects only 4/10 Gaussian rows.

A 10×200 matrix was concatenated with i.i.d. Gaussian entries and a 190×200 matrix with i.i.d. [0, 1] uniform distribution entries. In this case, one would expect that the Gaussian submatrix has the lowest $\mu_{avg}$ when M=10. FIG. 18 visualizes the results of running Insense and the Convex SS baseline algorithm on such a Φ. In all 10 random trials, Insense successfully selected all Gaussian rows and hence found the globally optimal set of sensors. FrameSense and EigenMaps miss, on average, 10-20% of the Gaussian sensors. The other baselines algorithms, including Convex SS, select only a small portion (<20%) of the Gaussian rows (sensors). Table 3 also indicates that Insense achieves better BP recovery performance, since it selects exclusively Gaussian rows, resulting in the minimum average coherence $\mu_{avg}$ of the resulting sensing matrix.

TABLE 3

Comparison of Insense against the baseline algorithms on selecting M = 10 rows from a structured uniform/Gaussian $\Phi$. Insense selected the set of sensors with the smallest $\mu_{avg}$ and achieved the best BP recovery performance.

|  | $\mu_{avg}(\Phi_\Omega)$ | $FP(\Phi_\Omega)$ | $CN(\Phi_\Omega)$ | Gaussian sensor ratio % | BP accuracy % |
|---|---|---|---|---|---|
| Insense | 0.3165 ± 0.0023 | 9320 ± 3292 | 1.46 ± 0.07 | 100 ± 0 | 58.55 ± 2.64 |
| FrameSense | 0.3273 ± 0.0059 | 6095 ± 1708 | 3.19 ± 0.92 | 84 ± 5 | 58.15 ± 2.26 |
| EigenMaps | 0.3215 ± 0.0021 | 7230 ± 2319 | 2.07 ± 0.12 | 90 ± 0 | 57.60 ± 3.72 |
| MSE-G | 0.5805 ± 0.0440 | 78530 ± 12450 | 5.99 ± 0.31 | 17 ± 4 | 49.90 ± 3.54 |
| MI-G | 0.6814 ± 0.0556 | 93260 ± 109250 | 6.26 ± 0.77 | 7 ± 4 | 51.60 ± 5.21 |
| Entropy-G | 0.7007 ± 0.0804 | 98950 ± 16216 | 6.61 ± 0.48 | 5 ± 7 | 53.70 ± 5.21 |
| Determinant-G | 0.7303 ± 0.0545 | 105700 ± 11228 | 6.57 ± 0.31 | 3 ± 4 | 55.50 ± 4.50 |
| Greedy SS | 0.7303 ± 0.0545 | 105700 ± 11228 | 5.57 ± 0.31 | 3 ± 4 | 55.50 ± 4.50 |
| Convex SS | 0.5788 ± 0.1140 | 75270 ± 27383 | 5.97 ± 0.77 | 20 ± 15 | 54.40 ± 4.20 |

Microbial diagnostics. The performance of Insense was assessed on a real-world dataset from microbial diagnostics. Microbial diagnostics seek to detect and identify microbial organisms in a sample. Next generation systems detect and classify organisms using DNA probes that bind (hybridize) to the target sequence and emit some kind of signal (e.g., fluorescence). Designing DNA probes for microbial diagnostics is an important application of sensor selection in the underdetermined sensing regime. For example, in the universal microbial sensing (UMD) framework (Aghazadeh et al., 2016), DNA probes acquire linear measurements from a microbial sample (e.g., bacterial, viral, etc.) in the form of a fluorescence resonance energy transfer (FRET) signal that indicates the hybridization affinity of a particular DNA probe to the organisms present in the sample. Given a matrix $\Phi$ that relates the hybridization affinities of DNA probes to microbial species, the objective is to recover a sparse vector x comprising the concentrations of the organisms in the sample from as few linear measurements as possible.

Insense and the baseline sensor selection algorithms were run on a large sensing matrix comprising the hybridization affinity of D=100 random DNA probes to N=42 bacterial species (as described in Aghazadeh et al., 2016). For each algorithm, after selecting M probes and constructing a sensing matrix $\Phi_\Omega$ with $|\Omega|=M$, BP recovery was performed for multiple sparse vectors x with random support (corresponding to the presence of a random subset of bacterial organisms). The same experiment was repeated for all $\binom{N}{K}$ sparse vectors x with K={2, 3, 5} non-zero elements (i.e., bacteria present), and the average BP recovery performance on identifying the composition of the samples is reported in Table 4. (To report the BP recovery for K=5 organisms, the inventors randomly generate 1000 realizations of the sparse vector x with 5 active elements and average the BP recovery performance on selected samples.)

The DNA probes selected by Insense outperform all of the baseline algorithms in identifying the bacterial organisms present. Specifically, Insense requires a smaller number of DNA probes than the other algorithm to achieve almost perfect detection performance (BP accuracy>99%), suggesting that Insense is the most cost-efficient algorithm to select DNA probes for this application. Moreover, the performance gap between Insense and the other algorithms grows as the number of bacterial species present in the sample K increases, indicating that Insense has better recovery performance in complex biological samples.

TABLE 4

Comparison of Insense against the baseline algorithms on selecting M DNA probes to identify pathogenic samples containing K bacterial organisms. Insense selected the sets of DNA probes that achieved the best pathogen identification performance.

BP accuracy in detecting organisms %

| | Number of organisms | | | | | | | | | | | |
|---|---|---|---|---|---|---|---|---|---|---|---|---|
| | K = 2 | | | | K = 3 | | | | K = 5 | | | |
| | Number of probes (M) | | | | | | | | | | | |
| | 5 | 8 | 12 | 15 | 8 | 12 | 15 | 20 | 12 | 15 | 20 | 25 |
| Insense | 25.52 | 68.33 | 94.78 | 99.65 | 26.46 | 71.74 | 93.95 | 99.53 | 16.78 | 51.95 | 92.71 | 99.10 |
| FrameSense | 27.73 | 61.83 | 88.40 | 95.71 | 22.70 | 62.32 | 82.29 | 98.36 | 10.79 | 35.16 | 81.92 | 96.50 |
| EigenMaps | 14.97 | 49.65 | 84.69 | 94.66 | 13.17 | 54.68 | 78.09 | 96.25 | 6.69 | 27.47 | 72.13 | 95.30 |
| MSE-G | 27.26 | 60.79 | 91.53 | 97.91 | 22.01 | 67.16 | 89.15 | 98.40 | 14.69 | 43.26 | 83.52 | 97.40 |
| MI-G | 26.22 | 59.98 | 89.68 | 96.40 | 20.96 | 65.69 | 84.10 | 97.39 | 13.48 | 37.96 | 79.72 | 96.00 |
| Entropy-G | 27.96 | 61.25 | 91.53 | 98.61 | 21.51 | 66.35 | 88.96 | 99.19 | 14.19 | 42.86 | 89.61 | 97.50 |
| Determinant-G | 14.85 | 46.75 | 82.13 | 94.55 | 12.49 | 48.97 | 76.13 | 96.03 | 6.29 | 24.48 | 72.73 | 92.81 |
| Greedy SS | 25.52 | 57.54 | 87.70 | 96.87 | 19.72 | 59.65 | 84.64 | 97.34 | 10.99 | 36.16 | 80.22 | 94.11 |
| Convex SS | 15.89 | 53.36 | 87.94 | 98.94 | 14.29 | 57.58 | 87.59 | 98.89 | 7.69 | 38.46 | 83.52 | 98.40 |
| Random | 25.57 | 61.53 | 88.79 | 96.66 | 22.37 | 62.29 | 86.15 | 97.72 | 12.79 | 38.88 | 82.94 | 86.44 |

Example 4

Use of Toehold Probes in UMD

While the theory of universal probes itself may allow for lower limits of detection than what were experimentally observed, the UMD system is largely limited by the low specificity of the MB probes. In order to increase the sensitivity and/or limit of detection, toehold probes were used in place of the MBs.

Toehold-probes were first developed to increase the specificity of hybridization between a probe and a target (Zhang et al., 2012). When a single-stranded probe is added to a target, hybridization can occur with a varying degree of energies, based upon the degree of mismatches or nucleotide content present in the hybridized strands. Toehold-probes utilize probes that are pre-hybridized to a semi-complementary "protector" strand, such that hybridization of a probe to a given target strand only occurs following displacement of the protector from the probe. In this way, probe hybridization will only occur to target strands that are more complementary (or more energetically favorable) to the probe than the protector strand. By using protected-probes, noise can be significantly reduced, allowing for higher resolution detection.

An additional advantage of using toehold-probes is that they are immune to changes in genomic GC content. One issue encountered with the UMD MB probes was that bacterial genomes containing a higher degree of guanine and cytosine motifs tended to hybridize more readily to the MB probes than genomes containing a lower percent of these nucleotides (due to the stronger chemical interactions observed between GC bases). This is problematic because it confounds the accuracy of predicted hybridization affinity values, and minimizes the range over which species containing a high percent of GC bases can bind to the MB probes. Toehold-probes bypass this issue, as they ensure that probe hybridizations are not dependent solely on the binding energy to the target, but on the relative binding energy of the target strand compared to the binding energy of the protector strand, thus eliminating a dependence on GC.

Figure 19:
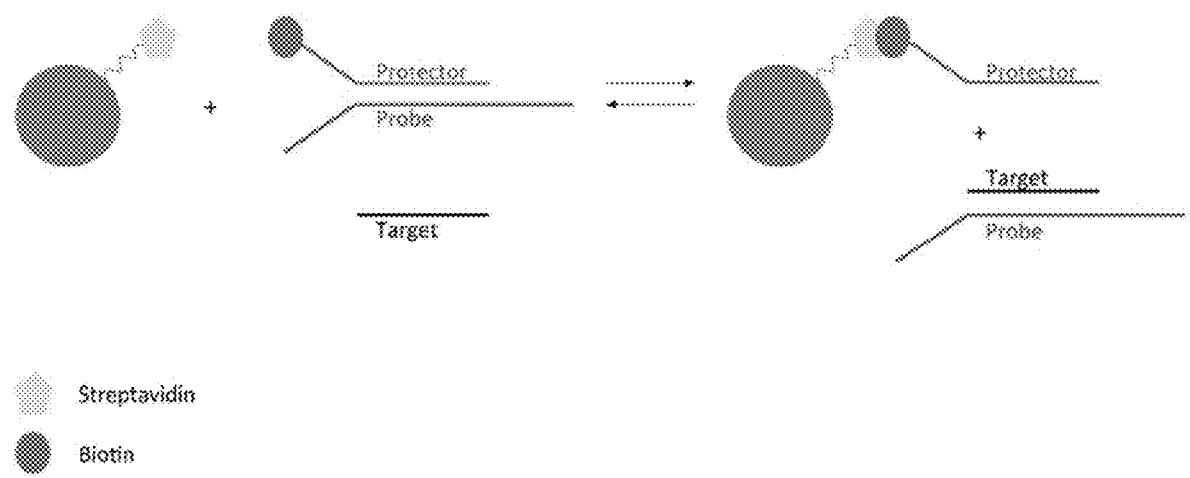
FIG. 19. Schematic of magnetic bead functionalization.

Magnetic bead functionalization. The first application of the toehold probes utilized streptavidin coated magnetic beads. Biotinylated protector strands were first complexed to complementary probe strands, then conjugated to streptavidin coated magnetic beads. Each probe strand was flanked by primer-specific regions on either end to allow for binding of primers to and subsequent amplification of the probe via quantitative PCR (qPCR) (FIG. 19). Target DNA was next introduced into solution and allowed to displace the protector strands. After probe-target hybridization, a magnet was used to pull protector strands out of solution, leaving only probe-target complexes in the supernatant. Following extraction and analysis of this supernatant, concentration of probe-target complexes was quantified via qPCR using primers specific for the probe strands. For initial studies, target strands were designed to be 50 base pairs long and perfectly complementary to the probe.

While the magnetic beads scheme offered improvements in LOD (from 1 µM to 10 pM) compared to the previous molecular beacon scheme, the resolution conferred by the bead capture method was limited, in that the observed probe concentration only spanned 2 orders of magnitude for the six orders of magnitude dynamic range observed in target concentrations. Further, the experimental LOD was higher than theoretical estimates, likely due to non-specific probe interactions, and lower than expected experimental capture efficiencies (the percent of biotinylated protectors bound to streptavidin-coated beads). To minimize the preponderance of non-specific interactions between the probe strands, the tube surface, and the beads, various blocking reagents (PolyT, Tween, and BSA) were tested. Of the three reagents examined, only the addition of PolyT conferred significant improvements in probe background.

To improve capture efficiencies, various experimental controls—including bead concentration, protector to probe ratios, hybridization time, buffer composition, and mixing method—were optimized; despite implementation of such modifications, however, experimental capture efficiency failed to exceed 97%. While seemingly high, a capture efficiency of 97% is non-ideal because it results in the production of a significant amount (3%) of background probe signal from the residual free-floating probe-protector complexes that have not been captured. This ultimately limits the achievable dynamic range to two orders of magnitude or less.

To address the issue of capture efficiency, three additional methods were explored to reduce background: 1) beads recapture, 2) pre-functionalization, and 3) double biotinylation. The beads recapture scheme involved running the probe, protector, and target solution through a second bead conjugation protocol to capture any residual protector/probe complexes that were not captured the first time. This method produced ~0.5% improvements in capture efficiency. The prefunctionalization method, on the other hand, required removal of the supernatant following initial conjugation of probe-protector complexes to the streptavidin-coated beads, but prior to addition of target DNA. In this way, the residual free-floating probe-protector complexes that had not been captured were manually removed from the background. Similar to beads recapture, this method also produced minor improvements in capture efficiency.

Figure 20:
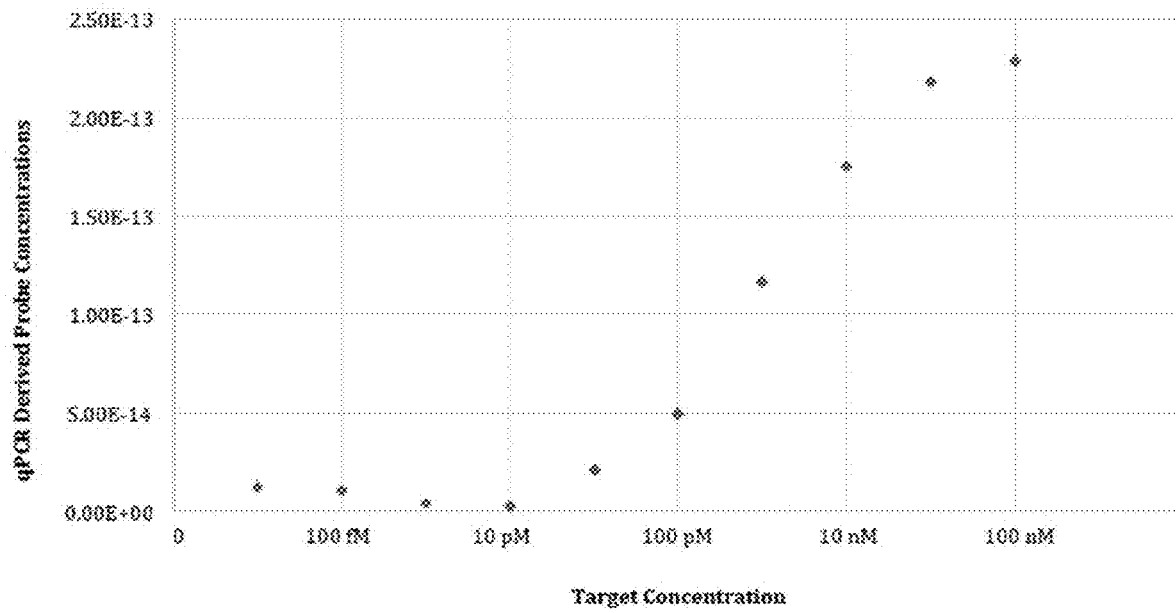
FIG. 20. Performance of magnetic bead functionalization. 0.1 nM of probe/protector-bead complexes were incubated with 10 fM to 100 nM of target for 2 hours in a PolyT buffer, and subsequently analyzed via qPCR. Dynamic range: 10 pM to 100 nM; Limit of Detection: 10 pM.

In the last scheme, protectors that had been complexed to two biotin molecules on their 3' were utilized, as opposed to the protectors that had been previously used that had been conjugated to only one biotin molecule on their 3' terminus. Application of these double-biotinylated protectors failed to produce any marked improvements in capture efficiency, however. Ultimately, future experimentation appeared to suggest streptavidin leaching from the magnetic beads surface as the main factor responsible for the 97-98% capture efficiency observed with the beads scheme. Overall performance of the magnetic beads system is presented in FIG. 20.

Figure 21:
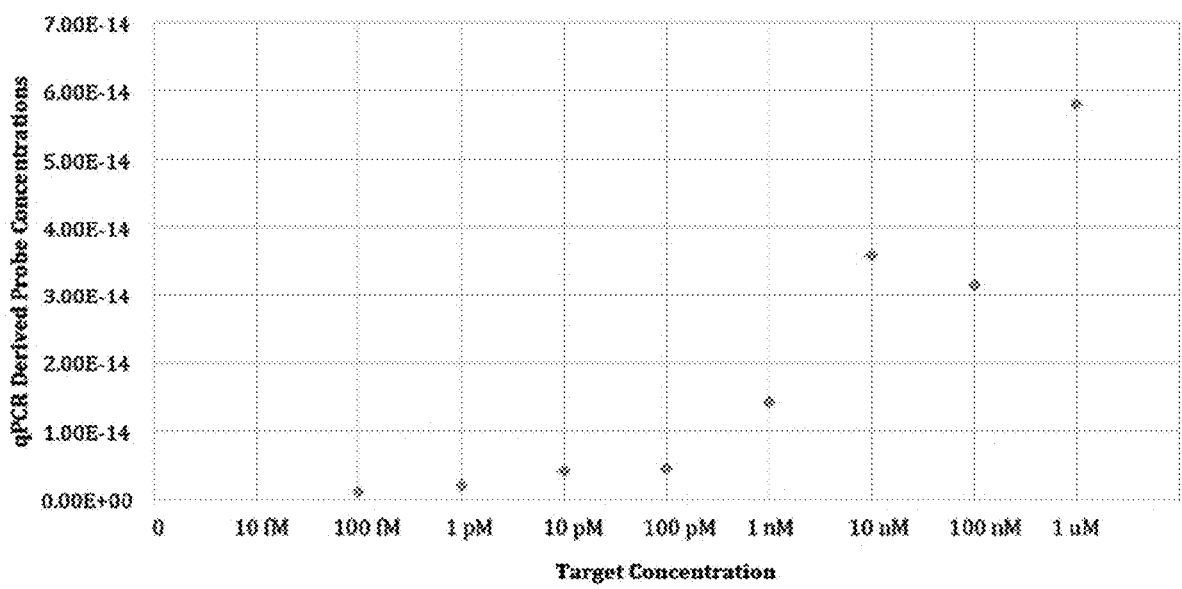
FIG. 21. Performance of neutravidin surface functionalization. 0.1 nM of probe/protector complexes were conjugated to the plate surface, and incubated with 100 fM to 1 uM of target for 2 hours in a buffer containing polyT and 1% SDS. Supernatant was subsequently analyzed via qPCR to determine final probe concentrations. Observed dynamic range spanned 5 orders of magnitude (100 pM to 1 uM), while the Limit of Detection was 100 pM.

Neutravidin surface functionalization. In addition to the magnetic beads method, the inventors also attempted to utilize neutravidin coated 96-well plates as a capture platform for biotinylated protector/protector-probe complexes. Neutravidin is a synthetically modified version of streptavidin that is known to exhibit decreased off-target binding to biotin. Similar to the streptavidin-coated beads, the neutravidin plate serves as an anchor that pulls down probe-protector complexes out of solution, while allowing probe-target complexes to float freely in the supernatant. As with the magnetic bead functionalization scheme, the dynamic range and sensitivity of the neutravidin capture platform was elucidated via construction of a series of log curves using either 0.1 nM, 1 nM, or 10 nM of probe DNA, and 100 fM to 1 uM of target DNA (with each order of magnitude in between tested). Initial examination of the system's performance exhibited a dynamic range spanning 5 orders of magnitude—from 100 pM to 1 uM—and a sensitivity of 100 pM. The resolution of the neutravidin plate system also appeared to be slightly worse than that of the magnetic beads system, given the 1.5 orders of magnitude range observed in probe concentration corresponding to the 5 orders of magnitude dynamic range exhibited in target concentration (FIG. 21).

Closer analysis of the dynamic range revealed a much lower than expected maximum probe concentration, however. This, coupled with other experimental data, led us hypothesize that the probe and target DNA molecules were nonspecifically interacting with the surface of the well. To mitigate the occurrence of such unfavorable interactions, the inventors attempted to block the neutravidin surface using both poly-T and BSA. Coating of the surface with poly-T strands, in combination with a brief detergent treatment using 1% SDS, resulted in reduction in non-specific interactions between the probe-target complexes and the neutravidin surface.

Overall, comparison of the LOD and dynamic range achieved via neutravidin surface functionalization revealed reductions in both sensitivity and dynamic range relative to magnetic bead functionalization.

Various optimizations for hybridization time and volume were pursued in an attempt to improve the neutravidin plate system's performance (either via improvements in sensitivity, resolution, or dynamic range); however such optimization efforts introduced no significant changes to the system's overall performance. While an increased hybridization time should theoretically improve sensitivity and resolution, especially given the slower kinetics observed with surfaces relative to homogenous solutions, non-favorable reactions—such as the non-specific interactions between the target/probe strands and the neutravidin surface—appeared to become more predominant with increased time. Of even greater concern, the neutravidin plates exhibited substantial leaching from the plate surface over the longest incubation period (6 hours), resulting in an ~20% loss in capture efficiency.

Figure 22:
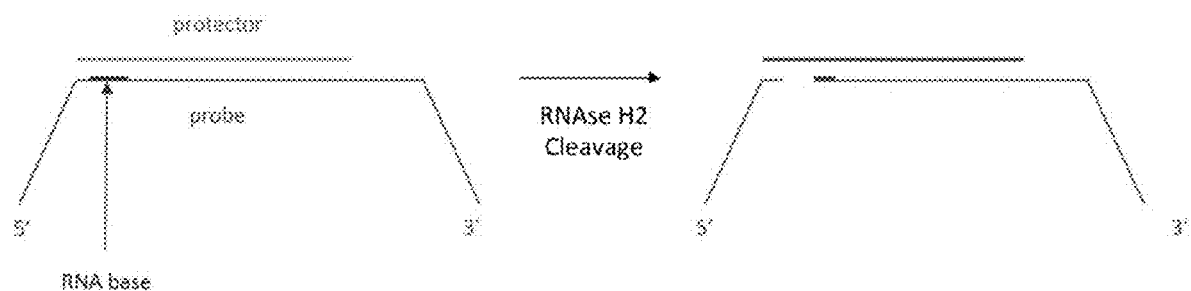
FIG. 22. Schematic for RNAse H induced cleavage of probe/protector complexes.

RNAse H induced cleavage of probe-protector complexes. Rather than using a capture-based scheme to isolate probe-protector complexes from probe-target complexes, restriction endonucleases were used to directly cleave probe-protector complexes. RNA bases were introduced into the non-homologous region of the probe, in order to produce probeprotector complexes containing regions of DNA bound to both RNA and DNA, and probe-target complexes containing regions of DNA only bound to DNA (FIG. 22). Aside from the introduction of these RNA bases, the probe size and sequence remained the same as that of the probes used in the magnetic bead functionalization and neutravidin surface functionalization schemes.

Figure 23:
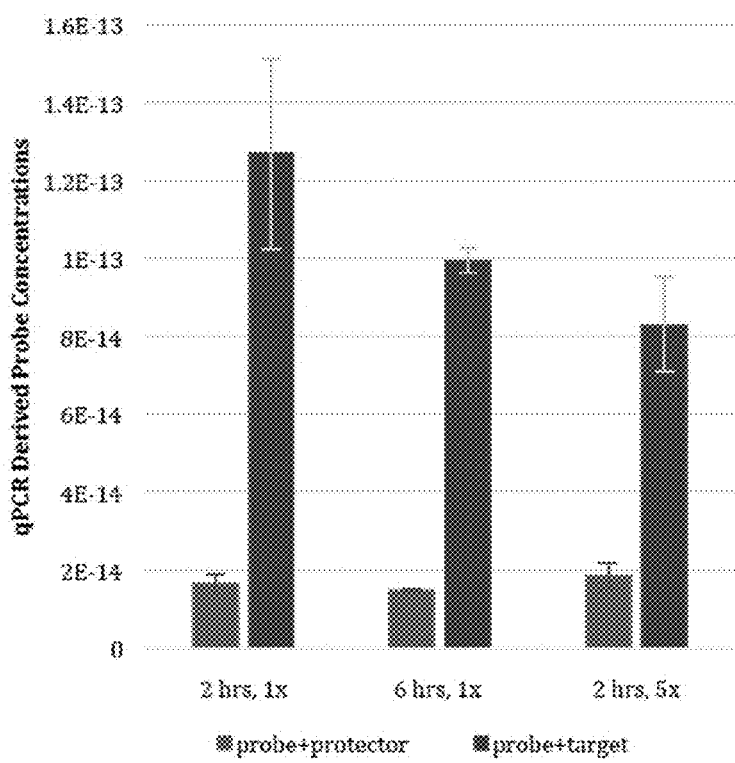
FIG. 23. Optimization of RNAse H Cleavage. Two incubation times (2 h and 6 h) and enzyme concentrations (1× and 5×) were tested to determine conditions for optimal cleavage of probe/protector complexes. A 2 h incubation with 1× enzyme was found to be most ideal. Conditions were performed in triplicate.

As with the magnetic bead functionalization and neutravidin surface functionalization schemes probe-protector complexes were first pre-annealed in solution. Varying concentrations of target strand (ranging from 10 fM to 1 uM) were then added to the solution, and allowed to displace the protector and hybridize to the probe. RNAse H2, a recombinant endo-ribonuclease that binds to RNA-DNA duplexes and cleaves 5' to the RNA base was then added into the mix and allowed to incubate for 1 hour. Following heat inactivation of the RNAse, the total solution was extracted and analyzed via qPCR, using primers specific for the probe. It should be mentioned that cleavage of the probe by RNAse H2 removes only one of the probe-flanking regions that is complimentary to the primer (i.e. the region specific for the forward primer); thus, cleavage products undergo slower, arithmetic amplification as opposed to the faster, geometric amplification experienced by probes containing regions specific for both primers. Various incubation times and enzyme concentrations were tested to determine optimal conditions for maximum probe/protector cleavage (FIG. 23). Analysis of the results of the RNAse H induced cleavage of probe-protector complexes scheme revealed a sensitivity of 10 pM and a dynamic range spanning six orders of magnitude (10 pM to 1 uM).

Figure 24:
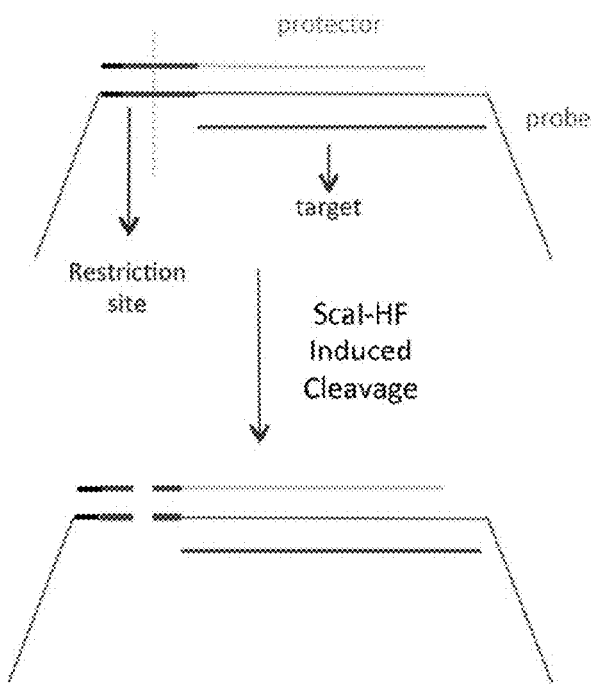
FIG. 24. Schematic for ScaI-HF induced cleavage of probe/protector complexes.
Figure 25:
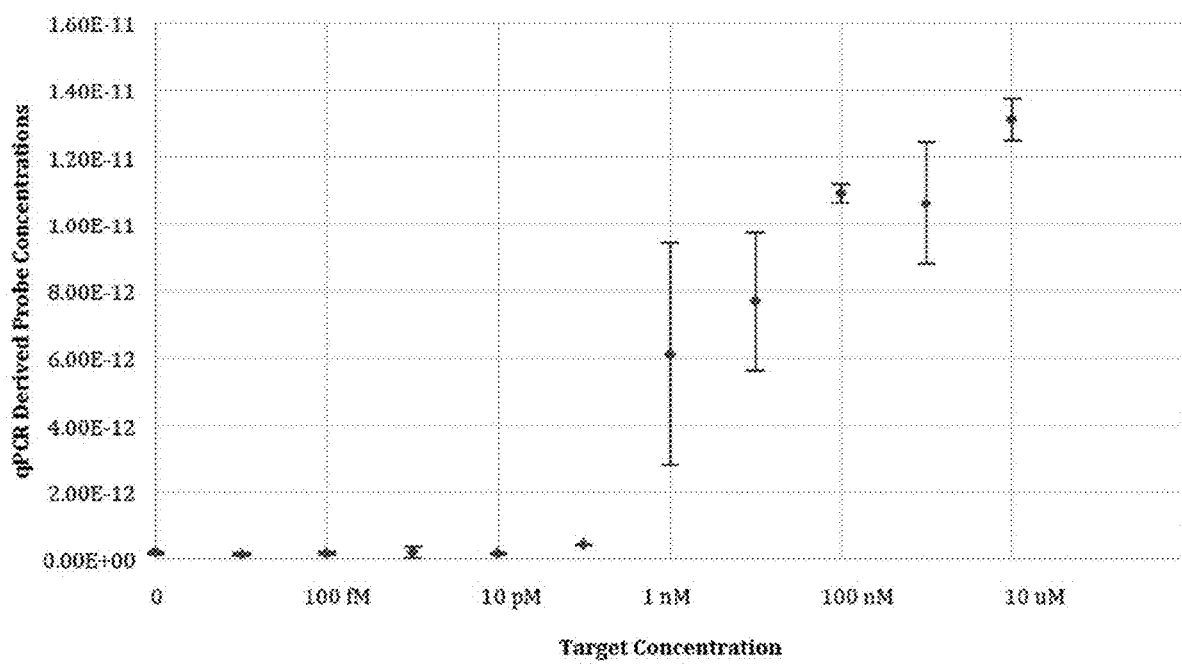
FIG. 25. Performance of ScaI-HF Induced Cleavage of Probe/Protector Complexes. 0.1 nM of probe/protector and varying target concentrations (10 fM to 10 uM) were incubated with ScaIHF for six hours. Solutions were subsequently analyzed via qPCR to determine final probe concentrations. Observed dynamic range spanned 5 orders of magnitude (100 pM to 10 uM), while with an approximate LOD of 100 pM. Conditions were performed in triplicate.

ScaI-HF induced cleavage of probe-protector complexes. Here again, restriction endonucleases were used for the purposes of cleaving probe-protector complexes in solution. In this scheme, a ScaI-HF restriction site was introduced into the non-homologous region of the both the probe and protector in order to induce cleavage of probe-protector complexes, while leaving probe-target complexes intact (FIG. 24). The protocol applied in this scheme followed exactly from the RNAse H induced cleavage of probe-protector complexes scheme. The dynamic range achieved with the Sca1-HF method spanned approximately 5 orders of magnitude; the LOD of the system was approximately 100 pM. The resolution for ScaI-HF induced cleavage of probe-protector complexes appeared to be greater than the resolutions seen in the magnetic bead functionalization, neutravidin surface functionalization, and RNAse H induced cleavage of probe-protector complexes schemes, given the 2 orders of magnitude range in probe concentrations observed for the 5 orders of magnitude dynamic range in target concentration (FIG. 25).

Figure 26:
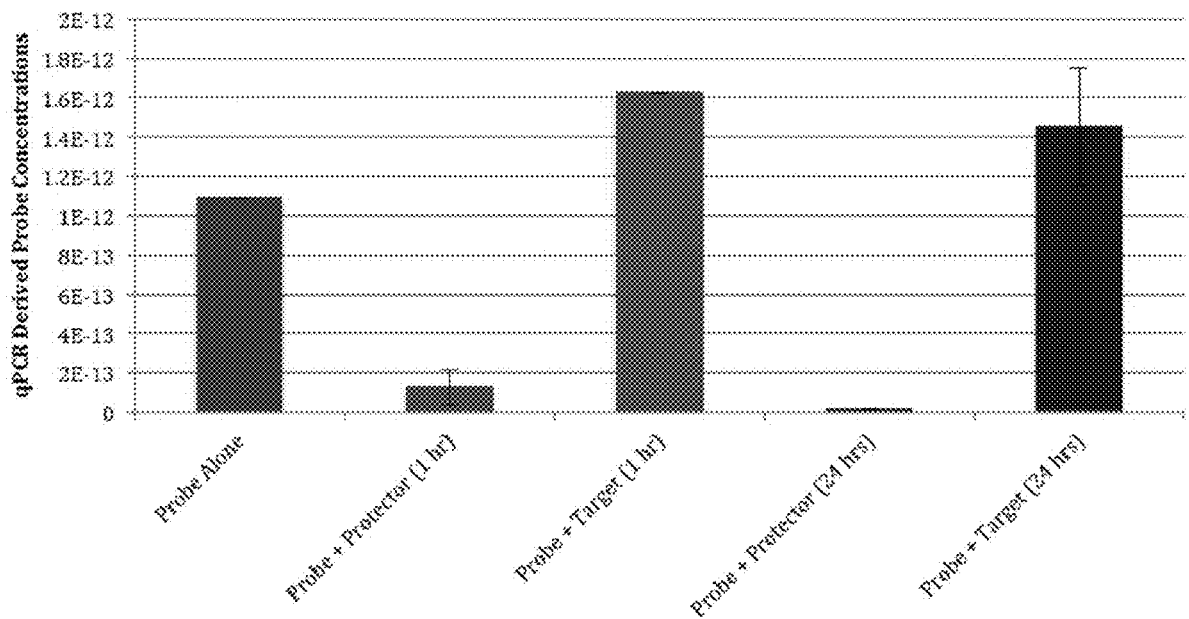
FIG. 26. Effect of Incubation Time on ScaI-HF Cleavage Efficiency. 0.1 nM of Probe-protector and probe-target complexes were incubated with 1× ScaI-HF for 1 hour (green) and 24 hours (blue). A probe alone control is shown in purple. The 24 h condition demonstrated 98% cleavage of probe-protector complexes relative to the 88% cleavage observed in the 1 h condition. Slight cleavage of probe-target complexes was also observed at 24 hours. All conditions were performed in triplicate.

As with the RNAse H induced cleavage of probe-protector complexes, various incubation times were tested to determine optimal conditions for cleavage using ScaI-HF (FIG. 26). While 88% cleavage was achieved with 1-hour incubation with the enzyme, 98% cleavage was observed with a 24-hour incubation period. However, slight probe/target cleavage was also detected in the latter condition. These results suggest that improvements in the ScaI-HF induced cleavage of probe-protector complexes scheme's performance may be achieved with increased incubation times, and perhaps optimization of other incubation parameters (such as enzyme concentration).

Figure 27:
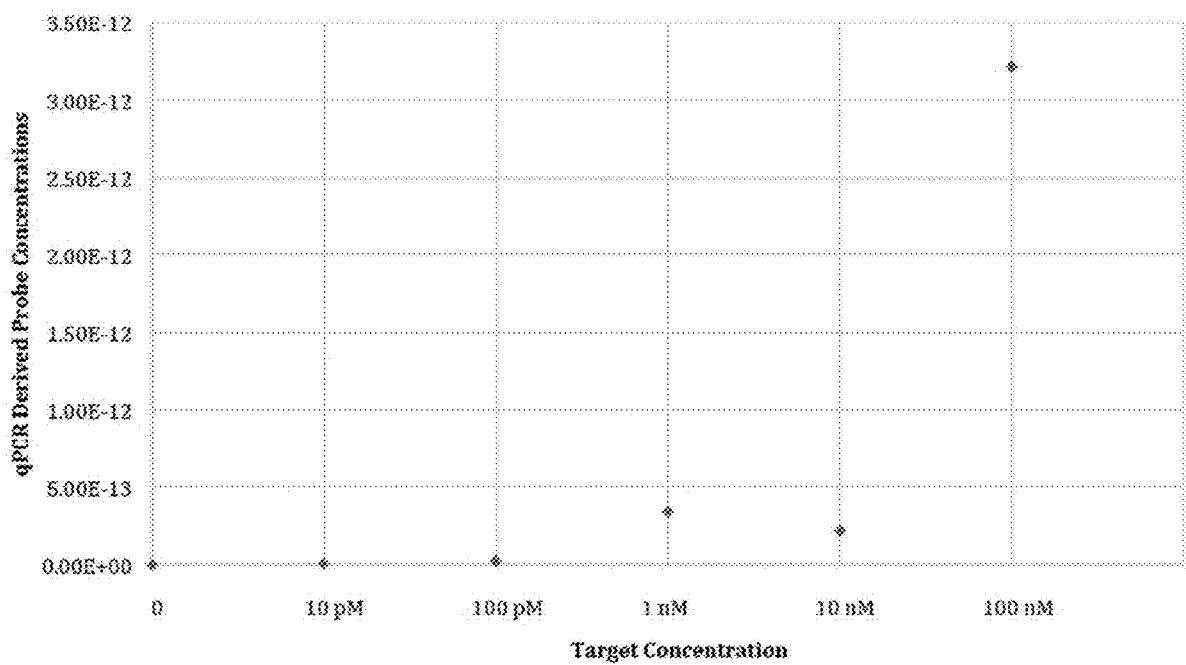
FIG. 27. Performance of Size Exclusion Via Column Chromotography. 0.1 nM of probe were incubated with varying concentrations (10 pM to 100 nM) of MRSA bacterial genome, and allowed to incubate for 2 h. Solutions were then run through a column filtration. Retained solution was analyzed via qPCR. Size Exclusion Via Column Chromotography exhibited poor sensitivity (approximately 10 nM), as a result of incomplete probe clearance, and clogging of the column filter.

Size exclusion via column chromatography. The last scheme involved using size exclusion chromatography to preferentially capture bacteria and bound probes, while allowing unbound probes to become discarded (via column filtration). Given the relative sizes of the bacterial genomes and probes used, 100 kDA columns were specifically chosen for this application. Unlike the previous schemes, this scheme utilized actual bacterial genomes (from clinical isolates of MRSA) as the target DNA. First, varying concentrations of probe—10 nM, 1 nM, and 0.1 nM—were mixed with varying concentrations of bacterial DNA. Following a 2-hour incubation, the bacterial DNA-probe mixture was pipetted into the top of the size filtration column. An additional 30-minute incubation period was observed to allow unbound probe to flow through the column filter. After three rounds of centrifugation and washing, the bacterial genome and bound probes were extracted, diluted, and analyzed via qPCR. Examination of the size exclusion via column chromatography scheme's results demonstrated poor sensitivity, a limited dynamic range, and a lower resolution compared to the previous schemes (FIG. 27). Additionally the column filtration method appeared to produce extreme inconsistencies in probe concentrations, and facilitate poor clearance of unbound probe. Based on subsequent experimentation, it appeared that the columns were becoming clogged—either by the excess probe-protector complexes or the bacterial genomes—thereby preventing filtration of unbound probe.

Example 5 smFISH for Detection of Probe Binding to Bacterial Genomes

Single molecule fluorescent in situ hybridization (smFISH) is another method of detecting the differential binding of probes to bacterial genomes that has the potential to improve the resolution and processing speeds for the identification of bacterial species. The inventors propose utilizing single molecule Fluorescence in situ Hybridization (smFISH) in combination with universal probes as a method of clinical microbial identification. FISH is a well-established system for detecting DNA or RNA in situ using fluorescent probes and (in most modern applications) digital imaging. Previous studies have validated the ability of FISH to resolve binding of just a single probe to its complementary target with high accuracy via methods that are cumulatively known as single molecule FISH (smFISH) (Femino et al., 1998; Raj et al., 2008). Using these techniques, the extent of universal probe hybridization to the bacterial genome can be accurately quantified via measurement of fluorescence intensity.

SmFISH bears numerous advantages over the previously described methods for a number of reasons. First, given that the technique is fundamentally an in situ method, probes can be delivered directly into cells, eliminating the need for DNA extraction and amplification. Further, as an imaging platform, this method precludes the need for physical separation of bacterial cells from human cells, as the two can easily be distinguished through visual discrimination. Second, smFISH obviates the necessity for the complicated de-convolution post-analyses carried out with the UMD and other preliminary schemes. This is primarily because the bacterial concentration is known (based on the number of cells imaged), therefore reducing the number of unknown variables to one—bacterial identity. Third, smFISH maintains significantly higher resolution and sensitivity compared to the previous technologies explored; as stated previously, some studies have even reported the ability to image single mRNA molecules using smFISH (Femino et al., 1998). Thus, this method should theoretically be able to resolve clinically relevant concentrations of bacteria.

One difficulty often encountered when working with smFISH strategies is the limited number of optically unique probes that can be delivered simultaneously. As shown with the previous UMD data, using a greater number of universal probes can often to lead to improvements in both specificity and sensitivity. Thus, a limitation on the number of probes that can be delivered simultaneously may be potentially cumbersome to the proposed strategy, as it imposes an upper limit on the diagnostic performance of the system. One way to circumvent this issue is by delivering probes iteratively, rather than simultaneously. However, this strategy would be too timeintensive, and ultimately in conflict with the goal of expediting microbial identification.

An alternative strategy that can be employed is spectral barcoding. Spectral barcoding is a method that identifies oligonucleotide sequences based on the distinctive combination of fluorescent signals that arise from the hybridization of differentially labeled fluorescent probes to that sequence (Itzkovitz & van Oudenaarden, 2011). Rather than conjugating a single spectrally unique fluorophore to each probe in the system, each probe can be multiplexed with a combination of n such fluorophores to produce $2^n-1$ probes with unique fluorescent/color combinations, therefore providing us with greater flexibility in probe design (Itzkovitz & van Oudenaarden, 2011). Using spectral barcoding techniques, the library of available unique probes can be vastly expanded. Thus, this strategy allows for the fulfillment of rapidity, while simultaneously expanding the achievable diagnostic performance of the smFISH system.

To use smFISH for detection, candidate probe sequences are selected, and the chosen probes are synthesized as Molecular Beacons (containing a 38 bp long loop region and 4 bp long stem regions) and conjugated to a Cy3 and Cy5 fluorophore on either end. The constructed MB probes will then be delivered into individual aliquots of cultured and fixed B. subtilis cells—each with varying concentration—using the smFISH protocol described below, and imaged under fluorescence. The concentration of cells used will vary between 1 uM (the cell concentration utilized in all previous UMD experiments), and 10 pM, with each bacterial cell aliquot differing in concentration by one order of magnitude. The concentration of probes delivered per condition will always be 10× the concentration of bacterial cells in that aliquot, to ensure that probes are in excess of the bacterial genome. For future applications, in which the starting bacterial concentration is not known, probes will be added in decreasing log dilutions to individual aliquots of the bacterial sample, such that the ratio of probe to bacterial genomic DNA remains >1, but not so high as to produce significant background.

To perform smFISH, bacteria are cultured overnight and then 1 mL of bacteria is pipetted into eppendorf tubes, to each of which 0.5 mL 1× PBS is added. The tubes are centrifuged at 3000 g for 5 minutes. While centrifuging, the probe/protector duplexes are prepared as follows. For a 100 uL, 10 uM solution, 10 uL of 100 uM biotinylated probe and 25 uL of 100 uM protector (2.5× excess) are combined with 65 uL sterile water and allowed to incubate at room temperature for ~3 hrs. Alternatively, annealing can be performed using a thermocycler annealing protocol. Once the bacterial tubes complete centrifugation, the supernatant is discarded and the pellet is resuspended in 0.5 mL 1× PBS. Then the tubes are centrifuged at 3000 g for 3 minutes. Supernatant is again discarded and 1.0 mL of ice cold BD cytofix is added to each tube. The tubes are incubated on a nutator at room temperature for 30 minutes. After incubating, centrifuge for 3.5 minutes at 3000 g, and wash twice with 1× PBS by discarding the supernatant, adding 1.0 mL 1× PBS, centrifuging at 6000 g for 3.5 minutes, and repeating. Then, 350 uL Lysis buffer (10 mM Tris HCL, pH 8.0/8.3, 0.1 M NaCl, 1 mM EDTA, 55 and 5% w/v Triton X-100; for a 10 mL solution, this involves 100 uL Tris-HCL, pH 8.3+0.058 g NaCl+20 uL 0.5 M EDTA, pH 8.0+500 uL Triton X-100) is added to each tube following by 100 uL lysozyme solution. Incubate at 32 degrees in semi-sterile incubator, on nutator, for 30 minutes, and then wash twice with 1× PBS. Add 100 uL RNAse A solution to each tube, and incubate at 60 degrees C. (in shake rack incubator) for 1.5 hrs at 250 rpm. Wash twice with 1× PBS; resuspend pellet in 1 mL 60% formamide (w/v in 2×SSC) and incubate at 65 degrees C. for 5 minutes. Centrifuge samples for 3-5 minutes at 3000×g. Add 45 uL hybridization buffer (1× PBS+60 mg/mL BSA (6%)) and 5 uL 40 nM probe to each tube and resuspend pellet. Incubate tubes in semi-sterile incubator for 4-16 hours. Collect supernatant from bacterial/probe tubes and store in separate Eppendorf tubes. Resuspend pellets in 0.5 mL 1× PBS and wash once. Stain using Hoechst Blue—5 min. Wash with 1× PBS twice—place on slide and image.

Based on the average total fluorescent intensity outputs of each condition, a calibration curve shall be constructed to ascertain the correlation between experimentally observed and theoretically obtained hybridization profiles. Any disagreement (error>10%) observed in experimental binding profiles will necessitate modification and optimization of the simulation parameters used. These parameters may involve varying the GC content of the generated probes, optimizing nearest-neighbor algorithms, or altering dangle energy contributions, for example.

In regards to the smFISH platform described here, sensitivity can be defined in two of the following ways: either 1) the minimum number of probes that can be detected, or 2) the minimum number of bacterial cells that can be successfully identified. For the purposes of clarity, the former shall be referred to as the detection limit, or LOD, while the latter shall be addressed as diagnostic sensitivity.

As stated previously, based on data from previous smFISH studies, the proposed system should be theoretically capable of detecting at least a minimum of 48 probe bindings with high accuracy (Raj et al., 2008). However, probes that exhibit low bindings to *B. subtilis* (1, 5, 10, 25, and 50 bindings respectively) shall also be separately tested to elucidate the detection limit of the smFISH protocol. Various wash buffers and blocking agents (such as BSA or Poly-Lysine) will be tested to minimize non-specific probe binding. Lastly, the baseline concentration of cells needed to resolve at the limit of detection (LOD) shall be probed via calculation of the mean fluorescent intensities and % error using a varying range of cell concentrations (10 pM to 1 uM), in order to gage the diagnostic sensitivity of the platform.

Having established the LOD and diagnostic sensitivity of the MB probes, use of sloppy toe-hold probes will be attempted to further improve sensitivity. As stated previously, toe-hold probes were initially developed by Dr. Dave Zhang as a method to improve the specificity of hybridization to targets containing SNPs (Zhang et al., 2012). However, the efficacy of these probes in the presence of mismatch heavy ("sloppy") protectors has never been validated. "Sloppy protectors" are desirable for the specific application, in that they allow for more customizable fine-tuning of probe hybridization profiles. As stated previously, the application of a protector serves to restrict the allowable range of delta G's that can be observed in binding. In the case of sloppy protectors, the aforementioned range can be modulated depending on the delta G of binding between the probe and protector, which can in turn be controlled by varying the number of mismatches in the protector. Thus, the inventors shall seek to validate the efficacy of sloppily protected probes against various energy targets.

Utilizing the X-probe design parameters described in (Wang & Zhang, 2015), five sets of Xprobes shall be created using protectors that exhibit 1-5 mismatches in their sequence, relative to the complement probe strand. Each of these X-probes will be tested against targets containing 0-4 mismatches. Displacement of each of the Xprobes in the presence of each target will be determined both in silico (via NuPACK) and experimentally (Zadeh et al., 2011). If the sloppy X-probes function in agreement with theoretical predictions, thereby confirming the efficacy of "mismatch" heavy protectors, the inventors shall utilize the same sequence tested above to create a toehold probe that binds at the detection limit to the *B. subtilis* genome, and re-examine the error profiles (in terms of total fluorescent intensity) for the same concentrations of cells to evaluate potential improvements in noise.

The "low-binding" toe-hold probe shall also be delivered into individual aliquots of *B. subtilis* cells that exhibit concentrations ranging between 1 uM and 10 pM, with each aliquot differing in concentration by one order of magnitude, to evaluate improvements in diagnostic sensitivity. As with the previous experiments described in Example 5, the toe-hold probes will be delivered at a 10-fold concentration relative to bacterial cells.

Using the sloppy toehold probes, the inventors expect to see improvements in probe-binding specificity when compared to unprotected probes or MB probes. If no such agreement is observed however, the utilization of unprotected probes or MB probes in combination with smFISH should still achieve a higher LOD than the probes used in the initial UMD design, given smFISH's ability to glean quantitative fluorescence data from individual cells rather than whole cell populations. This capability should ultimately serve to improve sensitivity beyond what was achieved using the previous UMD system.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. REFERENCES

The following references, to the extent that they provide exemplary procedural or other details supplementary to those set forth herein, are specifically incorporated herein by reference.

Aghazadeh, Universal Microbial Diagnostics using Random DNA Probes, (Rice University, 2014).
Aghazadeh et al., Universal microbial diagnostics using random DNA probes, *Sci. Adv.*, 2:e1600025 (2016).
Aghazadeh et al., Insense: Incoherent Sensor Selection for Sparse Signals, arXiv preprint arXiv:1702.07670 (2017).
Amini & Marvasti, Deterministic construction of binary, bipolar, and ternary compressed sensing matrices, *IEEE Trans. Inf. Theory*, 57:2360-70 (2011).
Attouch et al., Convergence of descent methods for semi-algebraic and tame problems: Proximal algorithms, forward-backward splitting, and regularized Gauss-Seidel methods, *Math. Program.*, 137:91-129 (2013).
Balageas et al., Structural Health Monitoring. Wiley Online Library, Vol. 493 (20060.
Baraniuk, Compressive sensing. *IEEE Signal Proc. Mag.*, 24:118-21 (2007).
Baraniuk, More is less: Signal processing and the data deluge. *Science*, 331:717-19 (2011).
Bauer & Reinhart, Molecular diagnostics of sepsis—Where are we today? *Int. J. Med. Microbiol.*, 300:411-13 (2010).
Bruckstein et al., On the uniqueness of nonnegative sparse solutions to underdetermined systems of equations. *IEEE T. Inform. Theory*, 54:4813-20 (2008).
Candès, Compressive sampling, *Proc. Intl. Cong. Math*, 3:1433-52 (2006).

Candes et al., Stable signal recovery from incomplete and inaccurate measurements, *Commun. Pur. Appl. Math.*, 59:1207-23 (2006).

Candès & Wakin, An introduction to compressive sampling, *IEEE Signal Process. Mag.*, 25:21-30 (2008).

Cai & Wang, Orthogonal matching pursuit for sparse signal recovery with noise. *IEEE T. Inform. Theory*, 57:4680-88 (2011).

Centers for Disease Control and Prevention Antibiotic Resistance threats in the United States, available on the world wide web at cdc.gov/drugresistance/[accessed November 2013].

Centers for Disease Control and Prevention Morbidity and Mortality Weekly Report, available on the world wide web at cdc.gov/mmwr/[accessed November 2013].

Chakravorty et al., Rapid universal identification of bacterial pathogens from clinical cultures by using a novel sloppy molecular beacon melting temperature signature technique. *J. Clin. Microbiol.*, 48:258-67 (2010).

Chen et al., Atomic decomposition by basis pursuit, *SIAM J. Sci. Comput.*, 20:33-61 (1998).

Chen & Ye, Projection onto a simplex, arXiv preprint arXiv:1101.6081 (2011).

Chepuri & Leus, Sparsity-promoting sensor selection for non-linear measurement models, *IEEE Trans. Signal Process.*, 63:684-98 (2015).

Condat, Fast projection onto the simplex and the '1-ball (2014), available on the world wide web at hal.archives-ouvertes Sr/hal-01056171.

Chung et al., A magneto-DNA nanoparticle system for rapid detection and phenotyping of bacteria. *Nat. Nanotechnol.*, 8:369-75 (2013).

Dai et al., Compressive sensing DNA microarrays. *EURASIP J. Bioinform. Syst. Biol.*, 162824 (2009).

Dark et al., Bench-to-bedside review: The promise of rapid infection diagnosis during sepsis using polymerase chain reaction-based pathogen detection. *Crit. Care*, 13:217 (2009).

Das & Kempe, Algorithms for subset selection in linear regression, *Proc. Ann. ACM Theory Comput. (STOC'08)*, pp. 45-54 (2008).

Das & Kempe, Submodular meets spectral: Greedy algorithms for subset selection, sparse approximation and dictionary selection, arXiv preprint arXiv:1102.3975 (2011).

Davenport et al., Signal processing with compressive measurements. *IEEE J. Sel. Top. Signa.*, 4:445-60 (2010).

Donoho & Tanner, Sparse nonnegative solution of underdetermined linear equations by linear programming. *Proc. Natl. Acad. Sci. U.S.A.*, 102:9446-51 (2005).

Donoho & Huo, Uncertainty principles and ideal atomic decomposition. *IEEE T. Inform. Theory*, 47:2845-62 (2001).

Donoho, Compressed sensing. *IEEE T. Inform. Theory*, 52:1289-1306 (2006).

Donoho et al., Stable recovery of sparse overcomplete representations in the presence of noise, *IEEE Trans. Inf. Theory*, 52:6-18 (2006).

Donoho et al., Message-passing algorithms for compressed sensing, *Proc. Natl. Acad. Sci. U.S.A.*, 106:18914-19 (2009).

Duarte-Carvajalino & Sapiro, Learning to sense sparse signals: Simultaneous sensing matrix and sparsifying dictionary optimization, *IEEE Trans. Image Process.*, 18:1395-1408 (2009).

Elad, Optimized projections for compressed sensing, *IEEE Trans. Signal Process.*, 55:5695-702 (2007).

Femino et al., Visualization of single RNA transcripts in situ. *Science*, 280:585-90 (1998).

Ford et al., Recent advances in nonlinear experimental design, *Technometrics*, 31:49-60x (1989).

Golovin et al., Online distributed sensor selection, *Proc. ACM Intl. Conf. Inf. Process. Sens. Net.*, pp. 220-231 (2010).

Gribonval & Vandergheynst, On the exponential convergence of matching pursuits in quasi-incoherent dictionaries, *IEEE Trans. Info. Theory*, 52:255-61 (2006).

Herzet et al., Exact recovery conditions for sparse representations with partial support information, *IEEE Trans. Inf. Theory*, 59:7509-24 (2013).

Hoyert & Xu, Deaths: Preliminary data for 2011. *Natl. Vital Stat. Rep.*, 61:1-51 (2012).

Itzkovitz & van Oudenaarden, Validating transcripts with probes and imaging technology. *Nat Methods*, 8:S12-S19 (2011).

Jeričević & Kušter, Non-linear optimization of parameters in Michaelis-Menten kinetics. *Croat. Chem. Acta*, 78:519-23 (2005).

Joshi & Boyd, Sensor selection via convex optimization, *IEEE Trans. Signal Process.*, 57:451-62 (2009).

Klompas et al., Automated surveillance of health care-associated infections. *Clin. Infect. Dis.*, 48:1268-75 (2009).

Krause et al., Near-optimal sensor placements in Gaussian processes: Theory, efficient algorithms and empirical studies, *J. Mach. Learn. Res.*, 9:235-284 (2008).

Martin et al., The epidemiology of sepsis in the United States from 1979 through 2000. *N. Engl. J. Med.*, 348: 1546-54 (2003).

Mohtashemi et al., Open-target sparse sensing of biological agents using DNA microarray. *BMC Bioinformatics*, 12:314 (2011).

Mylotte & Tayara, Blood cultures: Clinical aspects and controversies. *Eur. J. Clin. Microbiol. Infect. Dis.*, 19:157-63 (2000).

Needell & Vershynin, Uniform uncertainty principle and signal recovery via regularized orthogonal matching pursuit, *Found. Comput. Math.*, 9:317-334 (2009).

Needell & Vershynin, Signal recovery from incomplete and inaccurate measurements via regularized orthogonal matching pursuit, *IEEE J. Sel. Top. Signal Process.*, 4:310-16 (2010).

Nesterov, Gradient methods for minimizing composite objective function (2007).

Paolucci et al., Conventional and molecular techniques for the early diagnosis of bacteraemia. *Int. J. Antimicrob. Agents*, 36:S6-S16 (2010).

Pechorsky et al., Identification of pathogenic bacteria in blood cultures: Comparison between conventional and PCR methods. *J. Microbiol. Methods*, 78:325-30 (2009).

Peters et al., New developments in the diagnosis of bloodstream infections. *Lancet Infect. Dis.*, 4:751-60 (2004).

Petersen & Pedersen, The matrix cookbook, Technical University of Denmark, Tech. Rep. (2008).

Pinto, Bioterrorism: Health sector alertness. *J. Nat. Sci. Biol. Med.*, 4:24-28 (2013).

Raj et al., Imaging individual mRNA molecules using multiple singly labeled probes. *Nat Methods*, 5:877-79 (2008).

Ranieri et al., EigenMaps: Algorithms for optimal thermal maps extraction and sensor placement on multicore processors, in Proc. ACM/EDAC/IEEE Des. Auto. Conf. (DAC'12), June 2012, pp. 636-641.

Ranieri et al., Near-optimal sensor placement for linear inverse problems, *IEEE Trans. Signal Process.*, 62:1135-46 (2014).

Riedel & Carroll, Blood cultures: Key elements for best practices and future directions. *J. Infect. Chemother.*, 16:301-16 (2010).

Sambrook et al., Molecular Cloning (Cold Spring Harbor Lab. Press, ed. 3, 2001).

Sambrook et al., Molecular Cloning, app 8 (Cold Spring Harbor Lab. Press, ed. 3, 2001).

SantaLucia Jr. & Hicks, The thermodynamics of DNA structural motifs. *Annu. Rev. Biophys. Biomol. Struct.*, 33:415-40 (2004).

Sen et al., Sparsity-based data-driven approaches for damage detection in plates, *Mech. Syst. Signal Process.*, Under Review.

Shamaiah et al., Greedy sensor selection:Leveraging submodularity, in Proc. IEEE. Conf. Dec. Ctrl. (CDC'10), February 2010, pp. 2572-2577.

Sheikh, thesis, Rice University, 2010.

Sibley et al., Molecular methods for pathogen and microbial community detection and characterization: Current and potential application in diagnostic microbiology. *Infect. Genet. Evol.*, 12:505-21 (2012).

Sontakke et al., Use of broad range 16S rDNA PCR in clinical microbiology. *J. Microbiol. Methods*, 76:217-25 (2009).

Steinberg & Hunter, Experimental design: Review and comment, *Technometrics*, 26:71-97 (1984).

Strohmer & Heath, Grassmannian frames with applications to coding and communication, *Appl. Comput. Harmon. Anal.*, 14:257-75 (2003).

Tibshirani, Regression shrinkage and selection via the Lasso, *J. Roy. Stat. Soc. B Met.*, 58:267-88 (1996).

Tropp, Greed is good: Algorithmic results for sparse approximation. *IEEE T. Inform. Theory*, 50:2231-42 (2004).

Tropp et al., Designing structured tight frames via an alternating projection method, *IEEE Trans. Inf. Theory*, 51:188-209 (2005).

Tropp & Gilbert, Signal recovery from random measurements via orthogonal matching pursuit. *IEEE T. Inform. Theory*, 53:4655-66 (2007).

Tyagi & Kramer, Molecular beacons: Probes that fluoresce upon hybridization. *Nat. Biotechnol.*, 14:303-08 (1996).

Van Dorst et al., Recent advances in recognition elements of food and environmental biosensors: A review. *Biosens. Bioelectron.*, 26:1178-94 (2010).

Wang et al., Entropy-based sensor selection heuristic for target localization, in Proc. Intl. ACM Conf. Inf. Process. Sens. Net., March 2004, pp. 36-45.

Wang & Carreira-Perpinán, Projection onto the probability simplex: An efficient algorithm with a simple proof, and an application, arXiv preprint arXiv:1309.1541 (2013).

Wang & Zhang, Simulation-guided DNA probe design for consistently ultraspecific hybridization. *Nat. Chem.*, 7:545-53 (2015).

Zadeh et al., NUPACK: Analysis and design of nucleic acid systems. *J. Comput. Chem.*, 32:170-73 (2011).

Zhang et al., Optimizing the specificity of nucleic acid hybridization. *Nat. Chem.*, 4:208-14 (2012).

Zhou et al., L1 regularization approach to structural damage detection using frequency data, *Struct. Health Monit.*, 14:571-82 (2015).

---

What is claimed is:

1. A method of detecting a bacterial infection in a subject comprising:
    (a) providing a set of probes, wherein each probe in the set has a sequence comprising one of SEQ ID NOS: 1, 2, 3, 4 or 5, wherein the set of probes comprises at least one probe comprising each of SEQ ID NOS: 1, 2, 3, 4 and 5, and wherein the probes are optionally double stranded;
    (b) providing a first sample from said subject;
    (c) obtaining hybridization information for probes comprising each of SEQ ID NOS: 1, 2, 3, 4 and 5 with said sample; and
    (d) detecting the presence of one or more bacterial genomes in said sample if the hybridization information corresponds to a predetermined hybridization pattern for said set of probes with a known bacterial genome or a known combination of bacterial genomes.

2. The method of claim 1, wherein said first sample is a body fluid.

3. The method of claim 1, wherein step (d) comprises detecting the presence of more than one bacterial genome.

4. The method of claim 3, wherein the more than one bacterial genomes are from the same species.

5. The method of claim 3, wherein the more than one bacterial genomes are from different species.

6. The method of claim 1, wherein each of said probes is a molecular beacon.

7. The method of claim 1, wherein each of said probes further comprises a label.

8. The method of claim 1, wherein said one or more bacterial genomes are from pathogenic bacteria.

9. The method of claim 1, wherein step (c) comprises obtaining quantitative hybridization information.

10. The method of claim 9, further comprising quantitating the number of bacterial genomes in said sample.

11. The method of claim 10, further comprising performing steps (a)-(d) on a second sample from said subject.

12. The method of claim 11, wherein said second sample was obtained at a second point in time as compared to said first sample, and the number of bacterial genomes in said first and second samples is compared.

13. The method of claim 12, wherein an anti-bacterial therapy was administered between obtaining of said first and second samples, and said method assesses therapeutic efficacy.

14. The method of claim 1, further comprising treating said subject for the bacterial infection.

15. The method of claim 1, wherein said subject is a human or non-human mammal.

16. The method of claim 1, further comprising classifying the bacterial infection.

17. The method of claim 1, further comprising treating said subject based on the identification of one or more bacterial genomes in step (d).

18. A kit comprising a set of probes comprising SEQ ID NOS: 1, 2, 3, 4 and 5, and optionally having SEQ ID NOS: 6, 7, 8, 9 and 10, respectively, hybridized thereto.

* * * * *

SEQUENCE LISTING

```
<160> NUMBER OF SEQ ID NOS: 13

<210> SEQ ID NO 1
<211> LENGTH: 46
<212> TYPE: DNA
<213> ORGANISM: Artificial sequence
<220> FEATURE:
<223> OTHER INFORMATION: Synthetic probe

<400> SEQUENCE: 1
cgacggttgc ttgggtactt ggatgatgct aaattggtgt tggtcg          46

<210> SEQ ID NO 2
<211> LENGTH: 46
<212> TYPE: DNA
<213> ORGANISM: Artificial sequence
<220> FEATURE:
<223> OTHER INFORMATION: Synthetic probe

<400> SEQUENCE: 2
cgacggtgct ttgaatactt ggtagaggct ggagggtggt tggtcg          46

<210> SEQ ID NO 3
<211> LENGTH: 46
<212> TYPE: DNA
<213> ORGANISM: Artificial sequence
<220> FEATURE:
<223> OTHER INFORMATION: Synthetic probe

<400> SEQUENCE: 3
cgacggtgct gggtgaacta aagggtgggt gctatgggaa gggtcg          46
```

<210> SEQ ID NO 4
<211> LENGTH: 46
<212> TYPE: DNA
<213> ORGANISM: Artificial sequence
<220> FEATURE:
<223> OTHER INFORMATION: Synthetic probe

<400> SEQUENCE: 4
cgacttaatg aatgtgtggg cgcttggttg cttaatgagt gggtcg            46

<210> SEQ ID NO 5
<211> LENGTH: 46
<212> TYPE: DNA
<213> ORGANISM: Artificial sequence
<220> FEATURE:
<223> OTHER INFORMATION: Synthetic probe

<400> SEQUENCE: 5
cgacgtttct tttctggagg agggagggtt agttgttagg cagtcg            46

<210> SEQ ID NO 6
<211> LENGTH: 46
<212> TYPE: DNA
<213> ORGANISM: Artificial sequence
<220> FEATURE:
<223> OTHER INFORMATION: Synthetic probe

<400> SEQUENCE: 6
cgaccaacac caatttagca tcatccaagt acccaagcaa ccgtcg            46

<210> SEQ ID NO 7
<211> LENGTH: 46
<212> TYPE: DNA
<213> ORGANISM: Artificial sequence
<220> FEATURE:
<223> OTHER INFORMATION: Synthetic probe

<400> SEQUENCE: 7
cgaccaacca ccctccagcc tctaccaagt attcaaagca ccgtcg            46

<210> SEQ ID NO 8
<211> LENGTH: 46
<212> TYPE: DNA
<213> ORGANISM: Artificial sequence
<220> FEATURE:
<223> OTHER INFORMATION: Synthetic probe

<400> SEQUENCE: 8
cgacccttcc catagcaccc accctttagt tcacccagca ccgtcg            46

<210> SEQ ID NO 9
<211> LENGTH: 46
<212> TYPE: DNA
<213> ORGANISM: Artificial sequence
<220> FEATURE:
<223> OTHER INFORMATION: Synthetic probe

<400> SEQUENCE: 9
cgacccactc attaagcaac caagcgccca cacattcatt aagtcg            46

<210> SEQ ID NO 10
<211> LENGTH: 46
<212> TYPE: DNA
<213> ORGANISM: Artificial sequence
<220> FEATURE:
<223> OTHER INFORMATION: Synthetic probe

```
<400> SEQUENCE: 10
cgactgccta acaactaacc ctccctcctc cagaaaagaa acgtcg                    46

<210> SEQ ID NO 11
<211> LENGTH: 43
<212> TYPE: DNA
<213> ORGANISM: Artificial sequence
<220> FEATURE:
<223> OTHER INFORMATION: Synthetic nucleic acid

<400> SEQUENCE: 11
cgcgaccacc gaacaggcac tggagcctaa gccgaaccga tcg                       43

<210> SEQ ID NO 12
<211> LENGTH: 25
<212> TYPE: DNA
<213> ORGANISM: Artificial sequence
<220> FEATURE:
<223> OTHER INFORMATION: Synthetic probe

<400> SEQUENCE: 12
gcgagaagtt aagacctatg ctcgc                                           25

<210> SEQ ID NO 13
<211> LENGTH: 49
<212> TYPE: DNA
<213> ORGANISM: Artificial sequence
<220> FEATURE:
<223> OTHER INFORMATION: Synthetic probe

<400> SEQUENCE: 13
ccggccggat aggaccacag gatgcatgtc gtgtggtgga aagcgccgg                 49
```